US010059925B2

United States Patent
Kawaoka et al.

(10) Patent No.: US 10,059,925 B2
(45) Date of Patent: *Aug. 28, 2018

(54) HIGH TITER RECOMBINANT INFLUENZA VIRUSES WITH ENHANCED REPLICATION IN VERO CELLS

(71) Applicant: Wisconsin Alumni Research Foundation (WARF), Madison, WI (US)

(72) Inventors: Yoshihiro Kawaoka, Middleton, WI (US); Taisuke Horimoto, Bankyotan (JP); Shin Murakami, Shinagawa-ku (JP)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/816,807

(22) Filed: Aug. 3, 2015

(65) Prior Publication Data

US 2016/0024479 A1   Jan. 28, 2016

Related U.S. Application Data

(63) Continuation of application No. 12/912,411, filed on Oct. 26, 2010, now Pat. No. 9,109,013.

(60) Provisional application No. 61/254,795, filed on Oct. 26, 2009.

(51) Int. Cl.
| | |
|---|---|
| *C12N 7/00* | (2006.01) |
| *C07K 14/005* | (2006.01) |
| *A61K 39/00* | (2006.01) |

(52) U.S. Cl.
CPC .............. *C12N 7/00* (2013.01); *C07K 14/005* (2013.01); *A61K 2039/525* (2013.01); *C12N 2760/16052* (2013.01); *C12N 2760/16122* (2013.01); *C12N 2760/16133* (2013.01); *C12N 2760/16152* (2013.01)

(58) Field of Classification Search
None
See application file for complete search history.

(56) References Cited

U.S. PATENT DOCUMENTS

| 6,037,348 A | 3/2000 | Colacino et al. |
|---|---|---|
| 9,109,013 B2 | 8/2015 | Kawaoka et al. |
| 2007/0231348 A1 | 10/2007 | Kawaoka et al. |
| 2011/0110978 A1 | 5/2011 | Kawaoka et al. |

FOREIGN PATENT DOCUMENTS

| JP | 2009532352 A | 9/2009 |
|---|---|---|
| JP | 2016144463 A | 8/2016 |
| WO | WO-2004112831 A2 | 12/2004 |
| WO | WO-2007126810 A2 | 11/2007 |
| WO | WO-2011056591 A1 | 5/2011 |

OTHER PUBLICATIONS

"European Application Serial No. 10777154.5, Office Action dated May 2, 2016", 6 pgs.
"Japanese Application Serial No. 2012-536963, Amendment and Argument filed Jun. 26, 2015 to Office Action dated Jan. 6, 2015", 12 pgs.
"Japanese Application Serial No. 2012-536963, Examiners Decision of Final Refusal dated Nov. 17, 2015", (w/ English Translation), 8 pgs.
Chan, Winnie, et al., "The cold adapted and temperature sensitive influenza A/Ann Arbor/6/60 virus, the master donor virus for live attenuated influenza vaccines, has multiple defects in replication at the restrictive temperature", *Virology*, 380(2), (2008), 304-311.
Hickman, Danielle, et al., "An avian live attenuated master backbone for potential use in epidemic and pandemic influenza vaccines", *Journal of General Virology*, 89(Part 11), (2008), 2682-2690.
Kiseleva, Irina V, et al., "PB2 and PA genes control the expression of the temperature-sensitive phenotype of cold-adapted B/USSR/60/69 influenza master donor virus", *Journal of General Virology*, 91(4), (2010), 931-937.
Lee, Jong-Soo, et al., "The highly conserved HA2 protein of the influenza A virus induces a cross protective immune response", *Journal of Virological Methods*, 194(1-2), (2013), 280-288.
GenBank ABL77178.1, (2006).
GenBank AAO15329.1, (2003).
GenBank ABL7718 6 .1, (2006).
GenBank AAT69443.1, (2006).
"U.S. Appl. No. 14/745,236, Non Final Office Action dated Feb. 2, 2017", 14 pgs.
"U.S. Appl. No. 14/745,236, Response filed Dec. 23, 2016 to Restriction Requirement dated Sep. 23, 2016", 8 pgs.
"European Application Serial No. 10777154.5, Response filed Sep. 8, 2016 to Office Action dated May 2, 2016", 69 pgs.
"GenBank ABL77187", (2006).
"Polymerase PB2 [Influenza B virus (B/Hong Kong/330/2001)] GenBank ABL77188.1", (2006), 1 pg.
Li, et al., "Genesis of a highly pathogenic and potentially pandemic H5N1 influenza virus in eastern Asia", (2004), 209-213 pgs.
Lugovtsev, V. Y., et al., "Genetic Composition and Mutational Pattern of Influenza B Viruses Adapted to Replication in Embryonated Eggs", GenBank: AAT69446.1, (2005), 1 pg.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.

(Continued)

*Primary Examiner* — Benjamin P Blumel
(74) *Attorney, Agent, or Firm* — Schwegman Lundberg & Woessner, P.A.

(57) ABSTRACT

The invention provides a composition useful to prepare high titer influenza viruses, e.g., in the absence of helper virus, which includes internal genes from an influenza virus vaccine strain or isolate, e.g., one that is safe in humans, for instance, one that does not result in significant disease, and genes from vaccine seed virus isolates which include a HA gene segment with a HA2 sequence encoding a HA2 that confers enhanced growth in cells in culture, such as Vero cells.

20 Claims, 20 Drawing Sheets

Specification includes a Sequence Listing.

(56) References Cited

OTHER PUBLICATIONS

"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non Final Office Action dated Jun. 7, 2013", 9 pgs.
"U.S. Appl. No. 12/912,411, Non Final Office Action dated Sep. 24, 2014", 12 pgs.
"U.S. Appl. No. 12/912,411, Notice of Allowability dated May 20, 2015", 7 pgs.
"U.S. Appl. No. 12/912,411, Notice of Allowance dated Apr. 8, 2015", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 25, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response filed Mar. 16, 2015 to Final Office Action dated Jan. 14, 2015", 9 pgs.
"U.S. Appl. No. 12/912,411, Response filed Oct. 7, 2013 to Non Final Office Action dated Jun. 7, 2013", 10 pgs.
"U.S. Appl. No. 12/912,411, Response filed Dec. 31, 2014 to Non Final Office Action dated Sep. 24, 2014", 12 pgs.
"U.S. Appl. No. 12/912,411, Restriction Requirement dated Oct. 17, 2012", 9 pgs.
"European Application Serial No. 10777154.5, Examination Notification Art. 94(3) dated Oct. 6, 2014", 7 pgs.
"European Application Serial No. 10777154.5, Office Action dated Jul. 4, 2012", 2 pgs.
"European Application Serial No. 10777154.5, Response filed Jan. 14, 2013 to Office Action dated Jul. 4, 2012", 12 pgs.
"Hemagglutinin [Influenza A virus (A/swine/France/WVL13/1995(H1N1))]", GenBank Accession# AC025026, (May 22, 2009), 1 pg.
"International Application Serial No. PCT/US2010/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054128, Written Opinion dated Feb. 23, 2011", 8 pgs.
"Japanese Application Serial No. 2012-536963, Office Action dated Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Neuraminidase, partial [Influenza A virus (A/swine/France/WVL13/1995(H1N1))]", GenBank Accession# AC025028, (May 22, 2009), 2 pgs.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Jang, S.-W., et al., "Deoxygedunin, a Natural Product with Potent Neurotrophic Activity in Mice", PLoS ONE 5(7): e11528, (2010), 1-15.
Kistner, et al., "Cell culture (Vero) derived whole virus (H5N1) vaccine based on wild-type virus strain induces cross-protective immune responses", Vaccine, vol. 25, No. 32, (2007), 6028-6036.
Kovacova, A., et al., "Sequence similarities and evolutionary relationships of influenza virus A hemagglutinins.", Virus Genes, 24(1), (2002), 57-63.
Lee, M. S, et al., "Genetic and pathogenic characterization of H6NI avian influenza viruses isolated in Taiwan between 1972 and 2005", Avian Diseases, 50(4), (Dec. 2006), 561-571.
Li, K. S, et al., "Genesis of a highly pathogenic and potentially pandemic H5NI influenza virus in eastern Asia", Nature, 430(6996), (Jul. 8, 2004), 209-213.

Lin, Y P, et al., "Adaptation of egg-grown and transfectant influenza viruses for growth in mammalian cells: selection of hemagglutinin mutants with elevated pH of membrane fusion", Virology, vol. 233, No. 2, (1997), 402-410.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Neumann, G., et al., "An Improved Reverse Genetics System for Influenza A Virus Generation and Its Implications for Vaccine Production", Proc. Natl. Acad. Sci. USA, 102(46), (2005), 16825-16829.
Neumann, G., et al., "Emergence and pandemic potential of swine-origin HIN1 influenza virus", Nature (London), 459(7249), (Jun. 2009), 931-939.
Neumann, G., et al., "Reverse Genetics of Influenza Viruses— Applications in Research and Vaccine Design", Monographs in Virology, 27, (2008), 118-133.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Romanova, J., et al., "Live cold-adapted influenza A vaccine produced in Vero cell line", Virus Research, 103, (2004), 187-193.
Xu, X., et al., "Reassortment and evolution of current human influenza A and B viruses", Virus Research, 103, (2004), 55-60.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
PNAS, vol. 102, No. 46, (2005), 16825-16829.
"Adaptation of Egg-Grown and Transfectant Influenza Viruses for Growth in Mammalian Cells: Selection of Hemagglutinin Mutants with Elevated pH of Membrane Fusion", Virology, vol. 233, Issue. 2, [Online] retrieved from the internet: <http://www.sciencedirect.com/science/article/pii/S0042682297986268>, (1997), 402-410.
"U.S. Appl. No. 14/745,236, Advisory Action dated Nov. 15, 2017", 2 pgs.
"U.S. Appl. No. 14/745,236, Final Office Action dated Aug. 25, 2017", 16 pgs.
"U.S. Appl. No. 14/745,236, Response filed May 2, 2017 to Non Final Office Action dated Feb. 2, 2017", 10 pgs.
"U.S. Appl. No. 14/745,236, Response filed Nov. 7, 2017 to Final Office Action dated Aug. 25, 2017", 12 pgs.
"U.S. Appl. No. 14/745,236, Response filed Dec. 14, 2017 to Final Office Action dated Aug. 25, 2017", 12 pgs.
"European Application Serial No. 10777154.5, Communication Pursuant to Article 94(3) EPC dated Oct. 12, 2017", 7 pgs.
"Japanese Application Serial No. 2016-053990, Office Action dated Jun. 6, 2017", (w/ English Translation), 4 pgs.
"Japanese Application Serial No. 2016-053990, Response filed Dec. 6, 2017 to Office Action dated Jun. 6, 2017", W/English Claims, 23 pgs.
Horimoto, "Designing Vaccines for Pandemic Influenza", Current Topics Microbiol Immunol 333, (2009), 165-176.
Murakami, "Enhanced Growth of Influenza Vaccine Seed Viruses in Vero Cells Mediated by Broadening the Optimal pH Range for Virus Membrane Fusion", J Virol 86(3), (2012), 1405-1410.
Ozaki, "Generation of High-Yielding Influenza A Viruses in African Green Monkey Kidney (Vero) Cells by Reverse Genetics", J Virol 78(4), (2004), 1851-1857.
U.S. Appl. No. 12/912,411, filed Oct. 26, 2010, High Titer Recombinant Influenza Viruses With Enhanced Replication in Vero Cells, now U.S. Pat. No. 9,109,013.
"European Application Serial No. 10777154.5, Communication Pursuant to Article 94 (3) EPC dated Apr. 4, 2018", 7 pgs.
Fodor, E., et al., "Rescue of Influenza A Virus from Recombinant Virology DNA", *Journal of Virology*, 73(11), (Nov. 1999), 9679-9682.
Hoffman, Lucas R, et al., "Structure-Based Identification of an Inducer of the Low-pH Conformational Change in the Influenza Virus Hemagglutinin: Irreversible Inhibition of Infectivity", *Journal of Virology*, 71(11), (Nov. 1997), 8808-8820.

PR8(Cambridge)

PB2

AGCGAAAGCAGGTCAATTATATTCAATATGGAAAGAATAAAAGAACTAAGAAATCTAATGTCGCAGTCTCGCACCCGCGAGATA
CTCACAAAAACCACCGTGGACCATATGGCCATAATCAAGAAGTACACATCAGGAAGACAGGAGAAGAACCCAGCACTTAGGATG
AAATGGATGATGGCAATGAAATATCCAATTACAGCAGACAAGAGGATAACGGAAATGATTCCTGAGAGAAATGAGCAAGGACAA
ACTTTATGGAGTAAAATGAATGATGCCGGATCAGACCGAGTGATGGTATCACCTCTGGCTGTGACATGGTGGAATAGGAATGGA
CCAATGACAAATACAGTTCATTATCCAAAAATCTACAAAACTTATTTTGAAAGAGTCGAAAGGCTAAAGCATGGAACCTTTGGC
CCTGTCCATTTTAGAAACCAAGTCAAAATACGTCGGAGAGTTGACATAAATCCTGGTCATGCAGATCTCAGTGCCAAGGAGGCA
CAGGATGTAATCATGGAAGTTGTTTTCCCTAACGAAGTGGGAGCCAGGATACTAACATCGGAATCGCAACTAACGATAACCAAA
GAGAAGAAAGAAGAACTCCAGGATTGCAAAATTTCTCCTTTGATGGTTGCATACATGTTGGAGAGAGAACTGGTCCGCAAAACG
AGATTCCTCCCAGTGGCTGGTGGAACAAGCAGTGTGTACATTGAAGTGTTGCATTTGACTCAAGGAACATGCTGGGAACAGATG
TATACTCCAGGAGGGGAAGTGAAGAATGATGATGTTGATCAAAGCTTGATTATTGCTGCTAGGAACATAGTGAGAAGAGCTGCA
GTATCAGCAGACCCACTAGCATCTTTATTGGAGATGTGCCACAGCACACAGATTGGTGGAATTAGGATGGTAGACATCCTTAAG
CAGAACCCAACAGAAGAGCAAGCCGTGGATATATGCAAGGCTGCAATGGGACTGAAGAATTAGCTCATCCTTCAGTTTTGGTGGA
TTCACATTTAAGAGAACAAGCGGATCATCAGTCAAGAGAGGAAGAGGTGCTTACGGGCAATCTTCAAACATTGAAGATAAGA
GTGCATGAGGGATCTGAAGAGTTCACAATGGTTGGGAGAAGAGCAACAGCCATACTCAGAAAAGCAACCAGGAGATTGATTCAG
CTGATAGTGAGTGGGAGAGACGAACAGTCGATTGCCGAAGCAATAATTGTGGCCATGGTATTTTCACAAGAGGATTGTATGATA
AAAGCAGTTAGAGGTGATCTGAATTTCGTCAATAGGGCGAATCAGCGACTGAATCCTATGCATCAACTTTTAAGACATTTTCAG
AAGGATGCGAAAGTGCTTTTTCAAAATTGGGGAGTTGAACCTATCGACAATGTGATGGGAATGATTGGGATATTGCCCGACATG
ACTCCAAGCATCGAGATGTCAATGAGAGGAGTGAGAATCAGCAAAATGGGTGTAGATGAGTACTCCAGCACGGAGAGGGTAGTG
GTGAGCATTGACCGGTTCTTGAGAGTCAGGGACCAACAGGAAATGTACTACTGTCTCCCGAGGAGGTCAGTGAAACACAGGGA
ACAGAGAAACTGACAATAACTTACTCATCGTCAATGATGTGGGAGATTAATGGTCCTGAATCAGTGTTGGTCAATACCTATCAA
TGGATCATCAGAAACTGGGAAACTGTTAAAATTCAGTGGTCCCAGAACCCTACAATGCTATACAATAAAATGAATTTGAACCA
TTTCAGTCTTTAGTACCTAAGGCCATTAGAGGCCAATACAGTGGGTTTGTAAGAACTCTGTTCCAACAAATGAGGGATGTGCTT
GGGACATTTGATACCGCACAGATAATAAAACTTCTTCCCTTCCGACGCCTCCACCAAAGCAAAGTAGAATGCAGTTCTCCTCA
TTTACTGTGAATGTGAGGGGATCAGGAATGAGAATACTTGTAAGGGGCAATTCTCCTGTATTCAACTACAACAAGGCCACGAAG
AGACTCACAGTTCTCGGAAAGGATGCTGGCACTTTAACCGAAGACCCAGATGAAGGCACAGCTGGAGTGGAGTCCGCTGTTCTG
AGGGGATTCCTCATTCTGGGCAAAGAAGACAGGAGATATGGGCCAGCATTAAGCATCAATGAACTGAGCAACCTTGCGAAAGGA
GAGAAGGCTAATGTGCTAATTGGGCAAGGAGACGTGGTGTTGGTAATGAAACGAAAACGGGACTCTAGCATACTTACTGACAGC
CAGACAGCGACCAAAAGAATTCGGATGGCCATCAATTAGTGTCGAATAGTTTAAAAACGACCTTGTTTCTACT

SEQ ID NO:11

PB1

AGCGAAAGCAGGCAAACCATTTGAATGGATGTCAATCCGACCTTACTTTTCTTAAAAGTGCCAGCACAAAATGCTATAAGCACA
ACTTTCCCTTATACCGGAGACCCTCCTTACAGCCATGGGACAGGAACAGGATACACCATGGATACTGTCAACAGGACACATCAG
TACTCAGAAAAGGGAAGATGGACAACAAACACCGAAACTGGAGCACCGCAACTCAACCCGATTGATGGGCCACTGCCAGAAGAC
AATGAACCAAGTGGTTATGCCCAAACAGATTGTGTATTGGAAGCAATGGCTTTCCTTGAGGAATCCCATCCTGGTATTTTTGAA
AACTCGTGTATTGAAACGATGGAGGTTGTTCAGCAAACACGAGTAGACAAGCTGACACAAGGCCGACAGACCTATGACTGGACT
TTAAATAGAAACCAGCCTGCTGCAACAGCATTGGCCAACACAATAGAAGTGTTCAGATCAAATGGCCTCACGGCCAATGAGTCA
GGAAGGCTCATAGACTTCCTTAAGGATGTAATGGAGTCAATGAAAAAGAAGAAATGGGGATCACAACTCATTTTCAGAGAAAG
AGACGGGTGAGAGACAATATGACTAAGAAAATGATAACACAGAGAACAATAGGTAAAAGGAAACAGAGATTGAACAAAAGGGGT
TATCTAATTAGAGCATTGACCCTGAACACAATGACCAAAGATGCTGAGAGAGGGAAGCTAAAACGGAGAGCAATTGCAACCCCA
GGGATGCAAATAAGGGGGTTTGTATACTTTGTTGAGACAATGGCTAGCACTCAAAATGCTAGCCTCCGCATTGATTTGAAAACTTCA
ACAAGAAGAAGATTGAAAAAATCCGACCGCTCTTAATAGAGGGGACTGCATCATTGAGCCCTGGAATGATGATGGGCATGTTC
AATATGTTAAGCACTGTATTAGGCGTCTCCATCCTGAATCTTGGACAAAAGAGATACACCAAGACTACTTACTGGTGGGATGGT
CTTCAATCCTCTGACGATTTTGCTCTGATTGTGAATGCACCAAATCATGAAGGGATTCAAGCTGGAGTCGACAGGTTTTATCGA
ACCTGTAAGCTACTTGGAATCAATATGAGCAAGAAAAAGTCTTACATAAACAGAATCAGGTACATTTGAATTCACAAGTTTTTC
TATCGTTATGGGTTTGTTGCCAATTTCAGCATGGAGCTTCCCAGTTTTGGGGTGTCTGGGATCAACGAGTCAGCGGACATGAGT
ATTGGAGTTACTGTCATCAAAAACAATATGATAAACAATGATCTTGGTCCAGCAACAGCTCAAATGGCCCTTCAGTTGTTCATC
AAAGATTACAGGTACACCGTACCGATGCCATAGAGGTGACACACAAATACAAACCCGAAGATCATTTGAAATAAAGAAACTGTGG
GAGCAAACCCGTTCCAAAGCTGGACTGCTGGTCTCCGACGGAGGCCCAAATTTATACAACATTAGAAATCTCCACATTCCTGAA
GTCTGCCTAAAATGGGAATTGATGGATGAGGATTACCAGGGGCGTTTATGCAACCCACTGAACCCATTTGTCAGCCATAAAGAA
ATTGAATCAATGAACAATGCAGTGATGATGCCAGCACATGGTCCAGCCAAAAACATGGAGTATGATGCTGTTGCAACAACACAC
TCCTGGATCCCAAAAGAAATCGATCCATCTTGAATACAAGTCAAAGAGGAGTACTTGAAGATGAACAAAATGTACCAAAGGTGC
TGCAATTTATTTGAAAAATTCTTCCCAGCAGTTCATCAGAAGAACAGTCGGGATATCCAGTATGGTGGAGGCTATGGTTTCC
AGAGCCCGAATTGATGCACGGATTGATTTCGAATCTGAAGGATAAAGAAGAGTTCACTGAGATCATGAAGATCTGTTCC
ACCATTGAAGAGCTCAGACGGCAAAAATAGTGAATTTAGCTTGTCCTTCATGAAAAAATGCCTTGTTTCTACT

SEQ ID NO:10

Fig. 1A

PR8(Cambridge)

PA

AGCGAAAGCAGGTACTGATTCAAAATGGAAGATTTTGTGCGACAATGCTTCAATCCGATGATTGTCGAGCTTGCGGAAAAAACA
ATGAAAGAGTATGGGGAGGACCTGAAAATCGAAACAAACAAATTTGCAGCAATATGCACTCACTTGGAAGTATGCTTCATGTAT
TCAGATTTTCCACTTCATCAATGAGCAAGGCGAGTCAATAATCGTAGAACTTGGTGATCCTAATGCACTTTTTGAAGCACAGATTTT
GAAATAATCGAGGGAAGAGATCGCACAATGGCCTGGACAGTAGTAAACAGTATTTGCAACACTACAGGGGCTGAGAAACCAAAG
TTTCTACCAGATTTGTATGATTACAAGGAAAATAGATTTCATCGAAATTGGAGTAACAAGGAGGAAGTTCACATATACTATCTG
GAAAAGGCCAATAAAATTAAATCTGAGAAAACACACATCCACATTTTCTCGTTCACTGGGGAAGAAATGGCCACAAGGGCCGAC
TACACTCTCGATGAAGAAAGCAGGGCTAGGATCAAAACCAGGCTATTCACCATAAGACAAGAAATGGCCAGCAGAGGCCTCTGG
GATTCCTTTCGTCAGTCCGAGAGAGGAGAAGAGCAATTGAAGAAAGGTTTGAAATCACAGGAACAATGCGCAAGCTTGCCGAC
CAAAGTCTCCCGCCGAACTTCTCCAGCCTTGAAAATTTTAGAGCCTATGTGGATGGATTCGAACCGAACGGCTACATTGAGGGC
AAGCTGTCTCAAATGTCCAAAGAAGTAAATGCTAGAATTGAACCTTTTTTGAAAACAACACCACGACCACTTAGACTTCCGAAT
GGGCCTCCCTGTTCTCAGCGGTCCAAATTCCTGCTGATGGATGCCTTAAAATTAAGCATTGAGGACCCAAGTCATGAAGGAGAG
GGAATACCGCTATATGATGCAATCAAATGCATGAGAACATTCTTTGGATGGAAGGAACCCAATGTTGTTAAACCACACGAAAAG
GGAATAAATCCAAATTATCTTCTGTCATGGAAGCAAGTACTGGCAGAACTGCAGGACATTGAGAATGAGGAGAAAATTCCAAAG
ACTAAAAATATGAAAAAAACAAGTCAGCTAAAGTGGGCACTTGGTGAGAACATGGCACCAGAAAAGGTAGACTTTGACGACTGT
AAAGATGTAGGTGATTTGAAGCAATATGATAGTGATGAACCAGAATTGAGGTCGCTTGCAAGTTGGATTCAGAATGAGTTCAAC
AAGGCATGCGAACTGACAGATTCAAGCTGGATAGAGCTTGATGAGATTGGAGAAGATGTGGCTCCAATTGAACACATTGCAAGC
ATGAGAAGGAATTATTTCACATCAGAGGTGTCTCACTGCAGAGCCACAGAATACATAATGAAGGGGGTGTACATCAATACTGCC
TTACTTAATGCATCTTGTGCAGCAATGGATGATTTCCAATTAATTCCAATGATAAGCAAGTGTAGAACTAAGGAGGGAAGGCGA
AAGACCAACTTGTATGGTTTCATCATAAAAGGAAGATCCCACTTAAGGAATGACACCGACGTGGTAAACTTTGTGAGCATGGAG
TTTTCTCTCACTGACCCAAGACTTGAACCACACAAATGGGAGAAGTACTGTGTTCTTGAGATAGGAGATATGCTTCTAAGAAGT
GCCATAGGCCAGGTTTCAAGGCCCATGTTCTTGTATGTGAGGACAAATGGAACCTCAAAAATTAAAATGAAATGGGGAATGGAG
ATGAGGCGTTGTCTCCTCCAGTCACTTCAACAAATTGAGAGTATGATTGAAGCTGAGTCCTCTGTCAAAGAGAAAGACATGACC
AAAGAGTTCTTTGAGAACAAATCAGAAACATGGCCCATTGACCAAAGGAGTGGAGAAAGTTCCATTGGGAAGGTC
TGCAGGACTTTATTAGCAAAGTCGGTATTTAACAGCTTGTATGCATCTCCACAACTAGAAGGATTTTCAGCTGAATCAAGAAAA
CTGCTTCTTATCGTTCAGGCTCTTAGGGACAATCTGGAACCTGGGACCTTTGATCTTGGGGGGCTATATGAAGCAATTGAGGAG
TGCCTAATTAATGATCCCTGGGTTTTGCTTAATGCTTCTTGGTTCAACTCCTTCCTTACACATGCATTGAGTTAGTTGTGGCAG
TGCTACTATTTGCTATCCATACTGTCCAAAAAAGTACCTTGTTTCTACT

SEQ ID NO:12

NP

AGCAAAAGCAGGGTAGATAATCACTCACTGAGTGACATCAAAATCATGGCGTCCCAAGGCACCAAACGGTCTTACGAACAGATG
GAGACTGATGGAGAACGCCAGAATGCCACTGAAATCAGAGCATCCGTCGGAAAAATGATTGGTGGAATTGGACGATTCTACATC
CAAATGTGCACAGAACTTAAACTCAGTGATTATGAGGGACGGTTGATCCAAAACAGCTTAACAATAGAGAGAATGGTGCTCTCT
GCTTTTGACGAAAGGAGAAATAAATACCTGGAAGAACATCCCAGTGCGGGGAAAGATCCTAAGAAAACTGGAGGACCTATATAC
AGAAGAGTAAACGGAAAGTGGATGAGAGAACTCATCCTTTATGACAAAGAAGAAATAAGGCGAATCTGGCGCCAAGCTAATAAT
GGTGACGGCAACGGTCTGTCTGACTCACATGATGATCTGGCATTCCAATTTGAATGATGCAACTTATCAGAGGGACAAGGGCT
CTTGTTCGCACCGGAATGGATCCCAGGATGTGCTCTCTGATGCAAGGTTCAACTCTCCCTAGGAGTCGGAGCCGCAGGTGCT
GCAGTCAAAGGAGTTGGAACAATGGTGATGGAATTGGTCAGGATGATCAAACGTGGGATCAATGATCGGAACTTCTGGAGGGGT
GAGAATGGACGAAAAACAAGAATTGCTTATGAAAGAATGTGCAACATTCTCAAAGGGAAATTTCAAACTGCTGCACAAAAAGCA
ATGATGGATCAAGTGAGAGAGAGCCGGAACCCAGGGAATGCTGAGTTCGAAGATCTCACTTTTTCTAGCACGGTCTGCACTCATA
TTGAGAGGGTCGGTTGCTCACAAGTCCTGCTCGCTGCCTGTGTGTATGGACCTGCCGTAGCCAGTGGGTACGACTTTGAAAGA
GAGGGATACTCTCTAGTCGGAATAGACCCTTTCAGACTGCTTCAAAACAGCCAAGTGTACAGCCTAATCAGACCAAATGAGAAT
CCAGCACACAAGAGTCAACTGGTGTGGATGGCATGCCATTCTGCCGCATTTGAAGATCTAAGAGTATTGAGCTTCATCAAAGGG
ACGAAGGTGGTCCCAAGAGGGAAGCTTTCCAAGTAGAGGAGTTCAAATTGCTTCCAAGTGAAATATGGAGACTATGGAATCAAGT
ACACTTGAACTGAGAAGCAGGTACTGGGCCATAAGGACCAGAAGTGGAGGGAAACACCAATCAACAGAGGGCATCTGCGGGCCAA
ATCAGCATACAACCTACGTTCTCAGTACAGAGAAATCTCCCTTTTTGACAGAACAACCGTTATGGCAGCATTCACTGGGAATACA
GAGGGGAGAACATCTGACATGAGGACCGAAATCATAAGGATGATGGAAAGTGCAAGACCAGAAGATGTGTCTTTCCAGGGGCGG
GGAGTCTTCGAGCTCTCGGACGAAAAGGCAGCGAGCCCGATCGTGCCTTCCTTTGACATGAGTAATGAAGGATCTTTATTTCTTC
GGAGACAATGCAGAGGAGTACGACAATTAAAGAAAAATACCCTTGTTTCTACT

SEQ ID NO:13

M

AGCAAAAGCAGGTAGATATTGAAAGATGAGTCTTCTAACCGAGGTCGAAACGTACGTTCTCTCTATCATCCCGTCAGGCCCCCT
CAAAGCCGAGATCGCACAGAGACTTGAAGATGTCTTTGCAGGGAAGAACACCGATCTTGAGGTTCTCATGGAATGGCTAAAGAC
AAGACCAATCCTGTCACCTCTGACTAAGGGGATTTTAGGATTTGTGTTCACGCTCACCGTGCCCAGTGAGCGAGGACTGCAGCG
TAGACGCTTTGTCCAAAATGCCCTTAATGGGAACGGGGATCCAAATAACATGGACAAAGCAGTTAAACTGTATAGGAAGCTCAA
GAGGGAGATAACATTCCATGGGGCCAAAGAAATCTCACTCAGTTATTCTGCTGGTGCACTTGCCAGTTGTATGGGCCTCATATA
CAACAGGATGGGGGCTGTGACCACTGAAGTGGCATTTGGCCTGGTATGTGCAACCTGTGAACAGATTGCTGACTCCCAGCATCG

Fig. 1B

PR8 (Cambridge)
GTCTCATAGGCAAATGGTGACAACAACCAACCCACTAATCAGACATGAGAACAGAATGGTTTTAGCCAGCACTACAGCTAAGGC
TATGGAGCAAATGGCTGGATCGAGTGAGCAAGCAGCAGAGGCCATGGAGGTTGCTAGTCAGGCTAGGCAAATGGTGCAAGCGAT
GAGAACCATTGGGACTCATCCTAGCTCCAGTGCTGGTCTGAAAAATGATCTTCTTGAAAAATTTGCAGGCCTATCAGAAACGAAT
GGGGGTGCAGATGCAACGGTTCAAGTGATCCTCTCGCTATTGCCGCAAATATCATTGGGATCTTGCACTTGATATTGTGGATTC
TTGATCGTCTTTTTTTTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCATAGAGCTGGAGTAAA
AAACTACCTTGTTTCTACT

SEQ ID NO:14

NS

AGCAAAAGCAGGGTGACAAAGACATAATGGATCCAAACACTGTGTCAAGCTTTCAGGTAGATTGCTTTCTTTGGCATGTCCGCA
AACGAGTTGCAGACCAAGAACTAGGTGATGCCCCATTCCTTGATCGGCTTCGCCGAGATCAGAAATCCCTAAGAGGAAGGGGCA
GCACTCTTGGTCTGGACATCGAGACAGCCACACGTGCTGGAAAGCAGATAGTGGAGCGGATTCTGAAAGAAGAATCCGATGAGG
CACTTAAAATGACCATGGCCTCTGTACCTGCGTCGCGTTACCTAACCGACATGACTCTTGAGGAAATGTCAAGGGAATGGTCCA
TGCTCATACCCAAGCAGAAAGTGGCAGGCCCTCTTTGTATCAGAATGGACCAGGCGATCATGGATAAAAACATCATACTGAAAG
CGAACTTCAGTGTGATTTTTGACCGGCTGGAGACTCTAATATTGCTAAGGGCTTTCACCGAAGAGGGAGCAATTGTTGGCGAAA
TTTCACCATTGCCTTCTCTTCCAGGACATACTGCTGAGGATGTCAAAAATGCAGTTGGAGTCCTCATCGGAGGACTTGAATGGA
ATGATAACACAGTTCGAGTCTCTGAAACTCTACAGAGATTCGCTTGGAGAAGCAGTAATGAGAATGGGAGACCTCCACTCACTC
CAAAACAGAAACGAGAAATGGCGGGAACAATTAGGTCAGAAGTTTGAAGAAATAAGATGGTTGATTGAAGAAGTGAGACACAAA
CTGAAGGTAACAGAGAATAGTTTTTGAGCAAATAACATTTATGCAAGCCTTACATCTATTGCTTGAAGTGGAGCAAGAGATAAGA
ACTTTCTCATTTCAGCTTATTTAATAATAAAAAACACCCTTGTTTCTACT

SEQ ID NO:15

*Fig. 1C*

COMPARISON OF AMINO ACID SEQUENCES BETWEEN WT AND PR8-VERO

|     | POSITION | WT | PR8-VERO |
| --- | --- | --- | --- |
| HA2 | 117 | N | D |
| NA  | 255 | N | Y |
| PB2 | 740 | D | N(2/4) |

Fig. 3

GROWTH PROPERTIES OF THE HA2 N117D MUTANT IN MDCK CELLS

TIME POST-INFECTION (h)

INFECTIVITY TITERS ($LOG_{10}$ PFU/ml)

REPLICATION EFFICIENCY WAS COMPARABLE BETWEEN THE WT AND THE MUTANT.

POSITION OF HA2 117 IN THE 3D STRUCTURE OF HA

TRIMER    MONOMER    HA2

1934 HUMAN H1 HEMAGGLUTININ (MMDB ID: 26941, PDB ID: 1RU7)

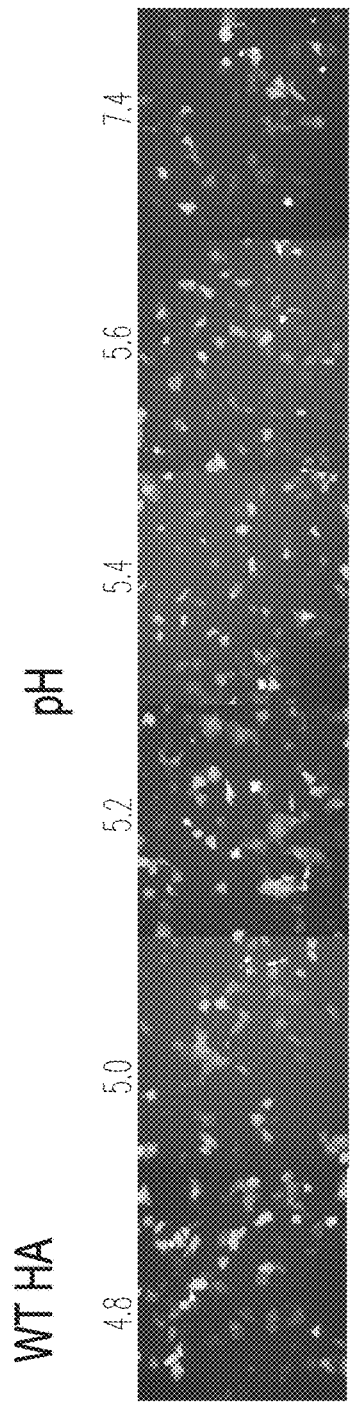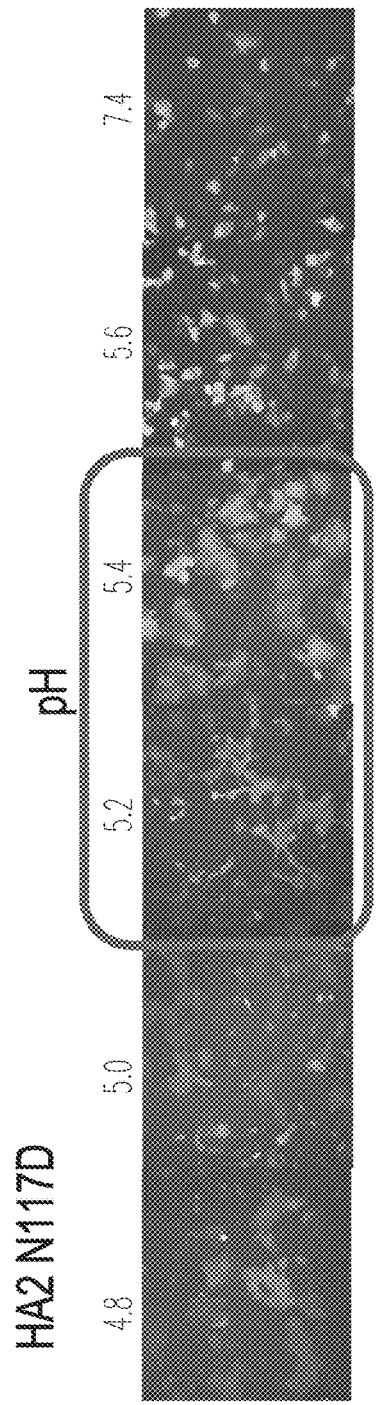
Fig. 8
THE HA2 N117D MUTANT FUSED CELLS AT A HIGHER pH THAN DID WT.

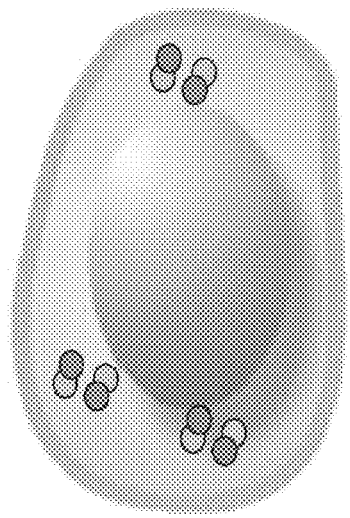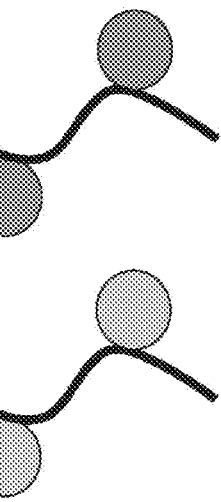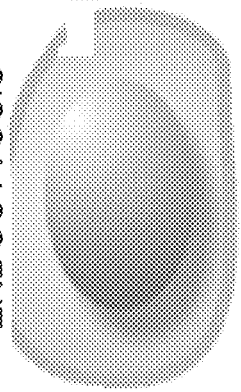
Fig. 9B

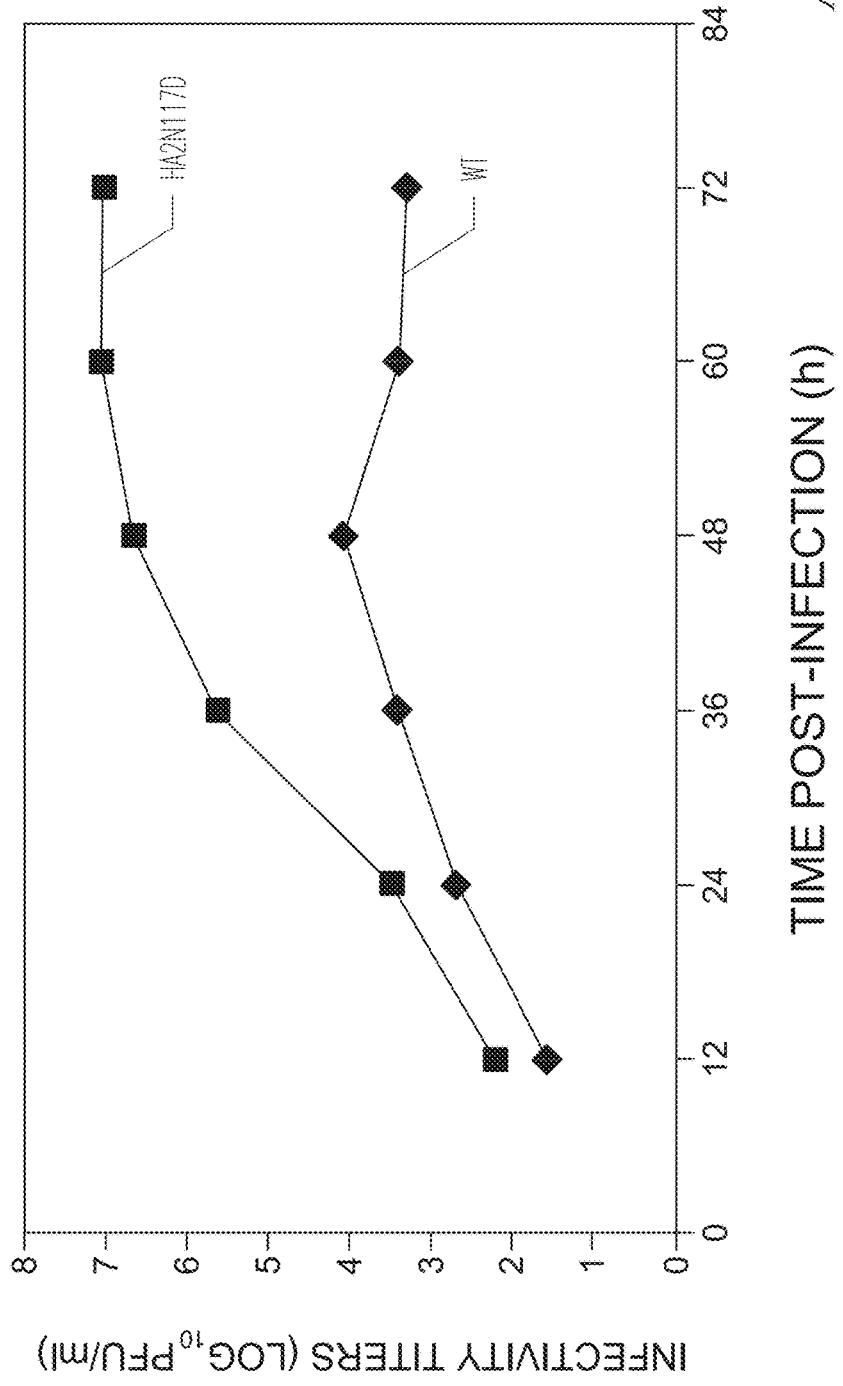

Fig. 11C THE HA2 N117D MUTATION ENHANCES THE REPLICATION EFFICIENCY OF THE A/YOKOHAMA/2017/2003 (H3N2) 6:2 REASSORTANT WITH A PR8 DONOR IN VERO CELLS.

HA1

```
      11                                                                                                  107
H3HU  ATLCLGHHAVPNGTLVKTITDDQIEVTNATELVQSSSTGKICN.NPHRILDGIDCTLIDALLGDPHCDVFQN.ETWDLFVERSKAFS.NCYPYDVPDYAS
H5AV  DQI I Y  NNSTEQ D  MEKN T  H QDILEKTHN  L DL GVKP ILR  SVAGW   N M  E L VPE SYI  KDNPVNGL   ENFN  EE
H5HU  DQI I Y  NNSTEQ D  MEKN T  H QDILERTHN  L DL GVKP ILR  SVAGW   N M  E I VPE SYI  KASPANDL   GNFN  EE
H9SW  DKI I YQSTNSTET D L ETN P  H K  LHTEHN ML AT LGHP ILDT  IEGLIY N S  LLLGGRE SYI   PS VNGM   GN ENLEE
H9HU  DKI I  QSTNSTET D L ETN P  H K  LHTEHN ML ATSLGHP ILDT  IEGLVY N S  LLLGGRE SYI    S VNGT   GN ENLEE 108                                                                                                 203
H3HU  LRSLVASSGTLEFITEGF...TWTGVTQN.GGSNACKRGPGSGFFSRLNWLTKSGSTYPVLNVTMPNNDNFDKLYIWGIHHPSTNQEQTSLYVQASGRVT
H5AV   KH LS TNHF K RI.IPRSS SNHDASS V S  PYNGR S  RNVV  I KNNA  TIKRSYN TNQE L IL      NDAA   K  QNPTTY S
H5HU   KH LSRINHF K QI.IPKSS SNHDASS V S  PYLGR S  RNVV  I KN A  TIKRSYN TNQE L VL      NDAA   K  QNPTTY S
H9SW      FS ASSYQR QI. PDTI .N SYS. T K  S....DS  RSMR   QKNNA   QDAQYT  RGKSI  M   N  P DTV   N  TRTDTTTS
H9HU     T FS ASSYQR QI. PDT  .N  YT. T R  S....GS  RSMR   QKSGF   QDAQYT  RGKSI          P YT   N   RNDTTTS 204                                                                                                 302
H3HU  VSTRRSQQTIIPNIGSRPWVRGLSSRISIYWTIVKPGDVLVINSNGNLIAPR.GYFKMRTGKSSIMRSDAPIDTCISECITPNGSIPNDKPFQNVNKITY
H5AV   G STLN RS   E AT   K N Q G MEF    L  N AINFE    F   EYA KIVKK G A  K GLEYGN NTK Q   M A NSSM  H  HPL I
H5HU   G STLN RL   E AT   K N Q G MEF    L  N AINFE    F   EYA KIVKK D T  K ELEYGN NTK Q   M A NSSM  H  HPL I
H9SW   T EDINR FK V  P  L N  HG  DY  S L   QT R R        WY HILSGESHGR LKT LNSGN  VQ Q ER GLNTTL  H  S YA
H9HU   T EDLNR FK V  P  L N  QG  DY  S L   QT R R        WY HVLSGGSHGR LKT LKGGN  VQ Q EK GLNSTL  H  S YA 303                    328   *
H3HU  GACPKYVKQNTLKLATGMRNVPEKQT....R   SEQ ID NO:16
H5AV   E      SGR V    L    QRE ....    SEQ ID NO:17
H5HU   E       S R V    L  T QRERRRKK   SEQ ID NO:18
H9SW   N     GVKS     V L    ARSS....   SEQ ID NO:19
H9HU   T     RV S     V L    ARSS....   SEQ ID NO:20
```

Fig. 12A

```
HA2
      1                                                                                                  100
H3HU  GLFGAIAGFIENGWEGMIDGWYGFRHQNSEGTGQAADLKSTQAAIDQINGKLNRVIEKTNEKFHQIEKEFSEVEGRIQDLEKYVEDTKIDLWSYNAELLV
H5AV             G  Q            H S EQ S Y    KE   K   GTTN V S  D M TQ EA G   NNL R  EN N KM  GFL V T
H5HU             G  Q            H S EQ S Y    KE   K   G TN V S  N M TQ EA GR  NNL R  EN N KM  GFL V T
H9SW             G  P L A        Q S DQ V M    RD   K   K TS V N  D M KQ GI DH      T LNMINNK D QIQ I T
H9HU             G  P L A        Q S DQ V M    RD   K   K TS V N  D M KQ EI DH      T LNMINNK D QIQ V A 101                                                                                                199
H3HU  ALENQHTIDLTDSEMNKLFEKTRRQLRENAEEMGNGCFKIYHKCDNACIESIRNGTYDHDVYRDEALNNRFQIKGVELKSGYKDWILWI.SFAISCFLLC
H5AV  LM  ER L FH  NVKN  D V L   D  K L     EF      E M    K     YPQ SE  RL  EE S  K E MGIYQ  S Y TVA SLA A
H5HU  LM  ER L FH  NVKN  D V L   D  K L     EF      E M    K     YPQ SE  RL  EE S  K E MGTYQ  S Y TVA SLA A
H9SW  L     K L EH ANV N  N VK A GS  M D K   EL     DQ M T      NRRK KE SKLE QK E  K E EGTYK  T Y TVA SLVIA
H9HU  L     K L EH ANV N  N VK A GS  M D K   EL     DQ M T      NRRK  E SRLE QK E -------------------------

200                  221
H3HU  VVLLGFIMWACQRGNIRCNICI   SEQ ID NO:23
H5AV   MIA LSL M SN SLQ R     SEQ ID NO:24
H5HU   MVA LSL M SN SLQ R     SEQ ID NO:25
H9SW  MGFAA LF  MS----------   SEQ ID NO:26
H9HU  ----------------------   SEQ ID NO:27
```

Fig. 12A CONT'D

```
  1 MKAILVLLLY TFATANADTL CIGYHANNST DTVDTVLEKN VTVTHSVNLL EDKHNGKLCK
 61 LRGVAPLHLG KCNIAGWILG NPECESLSTA SSWSYIVETP SSDNGTCYPG DFIDYEELRE
121 QLSSVSFER  FEIFPKTSSW PNHDSNKGVT AACPHAGAKS FYKNLIWLVK KGNSYPKLSK
181 SYINDKGKEV LVLWGIHHPS TSADQQSLYQ NADAYVFVGS SRYSKKFKPE IAIRPKVRDQ
241 EGRMNYWTL  VEPGDKITFE ATGNLVVPRY AFAMERNAGS GIIISDTPVH DCNTTCQTPK
301 GAINTSLPFQ NIHPITIGKC PKYVKSTKLR LATGLRNIPS IQSRGLFGAI AGFIEGGWTG
361 MVDGWYGYHH QNEQGSGYAA DLKSTQNAID EITNKVNSVI EKMNTQFTAV GKEFNHLEKR
421 IENLNKKVDD GFLDIWTYNA ELLVLLENER TLDYHDSNVK NLYEKVRSQL KNNAKEIGNG
481 CFEFYHKCDN TCMESVKNGT YDYPKYSEEA KLNREEIDGV KLESTRIYQI LAIYSTVASS
541 LVLVVSLGAI SFWMCSNGSL QCRICI  SEQ ID NO:21
```

Fig. 12B

A/Kawasaki/173/2001 (H1N1)
GLFGAIAGFIEGGWTGMVDGWYGYHHQNEQGSGYAADQKSTQNAINGITNKVNSVIEKMNTQFTAVG
KEFNKLERRMENLNKKVDDGFLDIWTYNAELLVLLENERTLDFHDSNVKDLYEKVKSQLKNNAKEIGNGCF
EFYHKCNNECMESVKNGTYDYPKYSEESKLNREKIDGVKLESMGVYQILAIYSTVASSLVLLVSLGAISFWM
CSNGSLQCRICI
SEQ ID NO:28

A/Kawasaki/UTK-4/2009 (H1N1)
GLFGAIAGFIEGGWTGMVDGWYGYHHQNEQGSGYAADQKSTQNAINGITNKVNSVIEKMNTQFTAVG
KEFNKLERRMENLNKKVDDGFIDIWTYNAELLVLLENERTLDFHDSNVKDLYEKVKSQLKNNAKEIGNGCFE
FYHKCNDECMESVKNGTYDYPKYSEESKLNREKIDGVKLESMGVYQILAIYSTVASSLVLLVSLGAISFWMC
SNGSLQCRICI
SEQ ID NO:29

A/Yokohama/2017/2003 (H3N2)
GIFGAIAGFIENGWEGMVDGWYGFRHQNSEGTGQAADLKSTQAAINQINGKLNRLIGKTNEKFHQIEKEF
SEVEGRIQDLEKYVEDTKIDLWSYNAELLVALENQHTIDLTDSEMDKLFERTKKQLRENAEDMGNGCFKIYH
KCDNACIESIRNGTYDHDVYRDEALNNRFQIKGVELKSGYKDWILWISFAISCFLLCVALLGFIMWACQKGN
IRCNICI
SEQ ID NO:30

Fig. 13

SEQUENCE LISTING

```
<160> NUMBER OF SEQ ID NOS: 30

<210> SEQ ID NO 1
<211> LENGTH: 2233
<212> TYPE: DNA
<213> ORGANISM: Influenza virus

<400> SEQUENCE: 1
agcgaaagca ggtactgatc caaaatggaa gattttgtgc gacaatgctt caatccgatg      60
attgtcgagc ttgcggaaaa aacaatgaaa gagtatgggg aggacctgaa aatcgaaaca     120
aacaaatttg cagcaatatg cactcacttg gaagtatgct tcatgtattc agattttcac     180
ttcatcaatg agcaaggcga gtcaataatc gtagaacttg gtgatccaaa tgcacttttg     240
aagcacagat ttgaaataat cgagggaaga gatcgcacaa tggcctggac agtagtaaac     300
agtatttgca acactacagg ggctgagaaa ccaaagtttc taccagattt gtatgattac     360
```

```
aaggagaata gattcatcga aattggagta acaaggagag aagttcacat atactatctg      420
gaaaaggcca ataaaattaa atctgagaaa acacacatcc acattttctc gttcactggg      480
gaagaaatgg ccacaaaggc agactacact ctcgatgaag aaagcagggc taggatcaaa      540
accagactat tcaccataag acaagaaatg gccagcagag gcctctggga ttcctttcgt      600
cagtccgaga gaggagaaga gacaattgaa gaaaggtttg aaatcacagg aacaatgcgc      660
aagcttgccg accaaagtct cccgccgaac ttctccagcc ttgaaaattt tagagcctat      720
gtggatggat tcgaaccgaa cggctacatt gagggcaagc tgtctcaaat gtccaaagaa      780
gtaaatgcta gaattgaacc ttttttgaaa acaacaccac gaccacttag acttccgaat      840
gggcctccct gttctcagcg gtccaaattc ctgctgatgg atgccttaaa attaagcatt      900
gaggacccaa gtcatgaagg agagggaata ccgctatatg atgcaatcaa atgcatgaga      960
acattctttg gatggaagga acccaatgtt gttaaaccac acgaaagggg aataaatcca     1020
aattatcttc tgtcatggaa gcaagtactg cagaactgc aggacattga gaatgaggag      1080
aaaattccaa agactaaaaa tatgaagaaa acaagtcagc taaagtgggc acttggtgag     1140
aacatggcac cagaaaaggt agactttgac gactgtaaag atgtaggtga tttgaagcaa     1200
tatgatagtg atgaaccaga attgaggtcg cttgcaagtt ggattcagaa tgagtttaac     1260
aaggcatgcg aactgacaga ttcaagctgg atagagctcg atgagattgg agaagatgtg     1320
gctccaattg aacacattgc aagcatgaga aggaattatt tcacatcaga ggtgtctcac     1380
tgcagagcca cagaatacat aatgaaggga gtgtacatca atactgcctt gcttaatgca     1440
tcttgtgcag caatggatga tttccaatta attccaatga taagcaagtg tagaactaag     1500
gagggaaggc gaaagaccaa cttgtatggt ttcatcataa aaggaagatc ccacttaagg     1560
aatgacaccg acgtggtaaa ctttgtgagc atggagtttt ctctcactga cccaagactt     1620
gaaccacata atgggagaa gtactgtgtt cttgagatag agatatgct tataagaagt      1680 gccataggcc aggtttcaag gcccatgttc ttgtatgtga gaacaaatgg aacctcaaaa     1740
attaaaatga aatggggaat ggagatgagg cgttgcctcc tccagtcact tcaacaaatt     1800
gagagtatga ttgaagctga gtcctctgtc aaagagaaag acatgaccaa agagttcttt     1860
gagaacaaat cagaaacatg gcccattgga gagtccccca aaggagtgga ggaaagttcc     1920
attgggaagg tctgcaggac tttattagca aagtcggtat tcaacagctt gtatgcatct     1980
ccacaactag aaggattttc agctgaatca agaaaactgc ttcttatcgt tcaggctctt     2040
agggacaacc tggaacctgg gacctttgat cttgggggc tatatgaagc aattgaggag     2100
tgcctgatta tgatccctg ggttttgctt aatgcttctt ggttcaactc cttccttaca      2160
catgcattga gttagttgtg gcagtgctac tatttgctat ccatactgtc caaaaagta      2220 ccttgtttct act                                                         2233
```

<210> SEQ ID NO 2
<211> LENGTH: 2341
<212> TYPE: DNA
<213> ORGANISM: Influenza virus

<400> SEQUENCE: 2

```
agcgaaagca ggcaaaccat ttgaatggat gtcaatccga ccttactttt cttaaaagtg       60
ccagcacaaa atgctataag cacaactttc ccttatactg gagaccctcc ttacagccat      120
gggacaggaa caggatacac catggatact gtcaacagga cacatcagta ctcagaaaag      180
```

```
ggaagatgga caacaaacac cgaaactgga gcaccgcaac tcaacccgat tgatgggcca      240
ctgccagaag acaatgaacc aagtggttat gcccaaacag attgtgtatt ggaggcgatg      300
gctttccttg aggaatccca tcctggtatt tttgaaaact cgtgtattga aacgatggag      360
gttgttcagc aaacacgagt agacaagctg acacaaggcc gacagaccta tgactggact      420
ctaaatagaa accaacctgc tgcaacagca ttggccaaca caatagaagt gttcagatca      480
aatggcctca cggccaatga gtctggaagg ctcatagact tccttaagga tgtaatggag      540
tcaatgaaca agaagaaat ggggatcaca actcattttc agagaaagag acgggtgaga      600
gacaatatga ctaagaaaat gataacacag agaacaatgg gtaaaagaa gcagagattg      660 aacaaaagga gttatctaat tagagcattg accctgaaca caatgaccaa agatgctgag      720
agagggaagc taaaacggag agcaattgca accccaggga tgcaaataag ggggtttgta      780
tactttgttg agacactggc aaggagtata tgtgagaaac ttgaacaatc agggttgcca      840
gttggaggca atgagaagaa agcaaagttg gcaaatgttg taaggaagat gatgaccaat      900
tctcaggaca ccgaactttc tttcaccatc actggagata caccaaatg gaacgaaaat      960 cagaatcctc ggatgttttt ggccatgatc acatatatga ccagaaatca gcccgaatgg     1020
ttcagaaatg ttctaagtat tgctccaata atgttctcaa acaaaatggc gagactggga     1080
aaagggtata tgtttgagag caagagtatg aaacttagaa ctcaaatacc tgcagaaatg     1140
ctagcaagca tcgatttgaa atatttcaat gattcaacaa gaagaagat tgaaaaaatc     1200 cgaccgctct aatagaggg gactgcatca ttgagccctg aatgatgat gggcatgttc     1260 aatatgttaa gcactgtatt aggcgtctcc atcctgaatc ttggacaaaa gagatacacc     1320
aagactactt actggtggga tggtcttcaa tcctctgacg attttgctct gattgtgaat     1380
gcacccaatc atgaagggat tcaagccgga gtcgacaggt tttatcgaac ctgtaagcta     1440
cttggaatca atatgagcaa gaaaaagtct tacataaaca gaacaggtac atttgaattc     1500
acaagttttt tctatcgtta tgggtttgtt gccaatttca gcatggagct tcccagtttt     1560
ggggtgtctg ggatcaacga gtcagcggac atgagtattg gagttactgt catcaaaaac     1620
aatatgataa acaatgatct tggtccagca acagctcaaa tggcccttca gttgttcatc     1680
aaagattaca ggtacacgta ccgatgccat ataggtgaca cacaaataca aaccgaaga     1740 tcatttgaaa taagaaact gtgggagcaa acccgttcca agctggact gctggtctcc     1800 gacggaggcc caatttata caacattaga aatctccaca ttcctgaagt ctgcctaaaa     1860
tgggaattga tggatgagga ttaccagggg cgtttatgca cccactgaa cccatttgtc     1920 agccataaag aaattgaatc aatgaacaat gcagtgatga tgccagcaca tggtccagcc     1980
aaaaacatgg agtatgatgc tgttgcaaca cacactcct ggatccccaa agaaatcga     2040 tccatcttga atacaagtca agaggagta cttgaggatg aacaaatgta ccaaaggtgc     2100 tgcaattat ttgaaaaatt cttccccagc agttcataca aagaccagt cgggatatcc     2160 agtatggtgg aggctatggt ttccagagcc cgaattgatg cacggattga tttcgaatct     2220
ggaaggataa agaagaaga gttcactgag atcatgaaga tctgttccac cattgaagag     2280
ctcagacggc aaaaatagtg aatttagctt gtccttcatg aaaaaatgcc ttgtttctac     2340
t                                                                    2341
```

<210> SEQ ID NO 3
<211> LENGTH: 2341
<212> TYPE: DNA
<213> ORGANISM: Influenza virus

<400> SEQUENCE: 3

```
agcgaaagca ggtcaattat attcaatatg gaaagaataa agaactacg aaatctaatg      60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa taacaaatac agttcattat    360
ccaaaaatct acaaaactta ttttgaaaga gtcgaaaggc taaagcatgg aacctttggc    420
cctgtccatt ttagaaacca gtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg gaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcaacgatt gaatcctatg   1320
catcaacttt taagacattt tcagaaggat gcgaaagtgc ttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagaatcc gggaccaacg aggaaatgta   1560
ctactgtctc ccgaggaggt cagtgaaaca caggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac taaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca agtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg agtggagtc cgctgttctg   2100
agggattcc tcattctggg caaagaagac aagagatatg gccagcact aagcatcaat   2160
gaactgagca accttgcgaa aggagagaag gctaatgtgc taattgggca aggagacgtg   2220
gtgttggtaa tgaaacggaa acgggactct agcatactta ctgacagcca gacagcgacc   2280
```

| aaaagaattc ggatggccat caattagtgt cgaatagttt aaaaacgacc ttgtttctac | 2340 |
| t | 2341 |

<210> SEQ ID NO 4
<211> LENGTH: 1565
<212> TYPE: DNA
<213> ORGANISM: Influenza virus

<400> SEQUENCE: 4

| agcaaaagca gggtagataa tcactcactg agtgacatca aaatcatggc gtctcaaggc | 60 |
| accaaacgat cttacgaaca gatggagact gatggagaac gccagaatgc cactgaaatc | 120 |
| agagcatccg tcggaaaaat gattggtgga attggacgat tctacatcca aatgtgcacc | 180 |
| gaactcaaac tcagtgatta tgagggacgg ttgatccaaa acagcttaac aatagagaga | 240 |
| atggtgctct ctgcttttga cgaaaggaga aataaatacc ttgaagaaca tcccagtgcg | 300 |
| gggaaagatc ctaagaaaac tggaggacct atatacagga gagtaaacgg aaagtggatg | 360 |
| agagaactca tcctttatga caaagaagaa ataaggcgaa tctggcgcca agctaataat | 420 |
| ggtgacgatg caacggctgg tctgactcac atgatgatct ggcattccaa tttgaatgat | 480 |
| gcaacttatc agaggacaag agctcttgtt cgcaccggaa tggatccag gatgtgctct | 540 |
| ctgatgcaag gttcaactct ccctaggagg tctggagccg caggtgctgc agtcaaagga | 600 |
| gttgaacaa tggtgatgga attggtcaga atgatcaaac gtgggatcaa tgatcggaac | 660 |
| ttctggaggg gtgagaatgg acgaaaaaca agaattgctt atgaaagaat gtgcaacatt | 720 |
| ctcaaaggga aatttcaaac tgctgcacaa aaagcaatga tggatcaagt gagagagagc | 780 |
| cggaacccag ggaatgctga gttcgaagat ctcactttc tagcacggtc tgcactcata | 840 |
| ttgagagggt cggttgctca caagtcctgc ctgcctgcct gtgtgtatgg acctgccgta | 900 |
| gccagtgggt acgactttga agggaggga tactctctag tcggaataga cccttttcaga | 960 |
| ctgcttcaaa acagccaagt gtacagccta atcagaccaa atgagaatcc agcacacaag | 1020 |
| agtcaactgg tgtggatggc atgccattct gccgcatttg aagatctaag agtattaagc | 1080 |
| ttcatcaaag gacgaaggt gctcccaaga gggaagcttt ccactagagg agttcaaatt | 1140 |
| gcttccaatg aaaatatgga gactatggaa tcaagtacac ttgaactgag aagcaggtac | 1200 |
| tgggccataa ggaccagaag tggaggaaac accaatcaac agagggcatc tgcgggccaa | 1260 |
| atcagcatac aacctacgtt ctcagtacag agaaatctcc cttttgacag aacaaccatt | 1320 |
| atggcagcat tcaatgggaa tacagagggg agaacatctg acatgaggac cgaaatcata | 1380 |
| aggatgatgg aaagtgcaag accagaagat gtgtctttcc aggggcgggg agtcttcgag | 1440 |
| ctctcggacg aaaaggcagc gagcccgatc gtgccttcct ttgacatgag taatgaagga | 1500 |
| tcttatttct tcggagacaa tgcagaggag tacgacaatt aaagaaaaat acccttgttt | 1560 |
| ctact | 1565 |

<210> SEQ ID NO 5
<211> LENGTH: 1027
<212> TYPE: DNA
<213> ORGANISM: Influenza virus

<400> SEQUENCE: 5

| agcaaaagca ggtagatatt gaaagatgag tcttctaacc gaggtcgaaa cgtacgtact | 60 |
| ctctatcatc ccgtcaggcc ccctcaaagc cgagatcgca cagagacttg aagatgtctt | 120 |
| tgcagggaag aacaccgatc ttgaggttct catggaatgg ctaaagacaa gaccaatcct | 180 |

```
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cactattgcc gcaaatatca ttgggatctt gcacttgaca ttgtggattc    840
ttgatcgtct tttttcaaa tgcatttacc gtcgctttaa atacggactg aaaggagggc    900
cttctacgga aggagtgcca aagtctatga gggaagaata tcgaaggaa cagcagagtg    960 ctgtggatgc tgacgatggt cattttgtca gcatagagct ggagtaaaaa actaccttgt   1020
ttctact                                                            1027

<210> SEQ ID NO 6
<211> LENGTH: 890
<212> TYPE: DNA
<213> ORGANISM: Influenza virus

<400> SEQUENCE: 6
agcaaaagca gggtgacaaa aacataatgg atccaaacac tgtgtcaagc tttcaggtag     60
attgctttct ttggcatgtc cgcaaacgag ttgcagacca gaactaggc gatgccccat    120 tccttgatcg gcttcgccga gatcagaaat ccctaagagg aaggggcagt actctcggtc    180
tggacatcaa gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct ttgtatcaga atggaccagg cgatcatgga taagaacatc atactgaaag    420
cgaacttcag tgtgattttt gaccggctgg agactctaat attgctaagg ctttccaccg    480
aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga agataacaga gaatagtttt    780
gagcaaataa catttatgca agccttacat ctattgcttg aagtggagca agagataaga    840
actttctcgt ttcagcttat ttagtactaa aaaacaccct tgtttctact               890

<210> SEQ ID NO 7
<211> LENGTH: 1775
<212> TYPE: DNA
<213> ORGANISM: Influenza virus

<400> SEQUENCE: 7
agcaaaagca ggggaaaata aaaacaacca aaatgaaggc aaacctactg gtcctgttat     60
```

| | |
|---|---:|
| gtgcacttgc agctgcagat gcagacacaa tatgtatagg ctaccatgcg aacaattcaa | 120 |
| ccgacactgt tgacacagta ctcgagaaga atgtgacagt gacacactct gttaacctgc | 180 |
| tcgaagacag ccacaacgga aaactatgta gattaaaagg aatagcccca ctacaattgg | 240 |
| ggaaatgtaa catcgccgga tggctcttgg gaaacccaga atgcgaccca ctgcttccag | 300 |
| tgagatcatg gtcctacatt gtagaaacac caaactctga gaatggaata tgttatccag | 360 |
| gagatttcat cgactatgag gagctgaggg agcaattgag ctcagtgtca tcattcgaaa | 420 |
| gattcgaaat atttcccaaa gaaagctcat ggcccaacca aacacaaac ggagtaacgg | 480 |
| cagcatgctc ccatgagggg aaaagcagtt tttacagaaa tttgctatgg ctgacggaga | 540 |
| aggagggctc atacccaaag ctgaaaaatt cttatgtgaa caaaaaaggg aaagaagtcc | 600 |
| ttgtactgtg gggtattcat cacccgccta acagtaagga caacagaat ctctatcaga | 660 |
| atgaaaatgc ttatgtctct gtagtgactt caaattataa caggagattt accccggaaa | 720 |
| tagcagaaag acccaaagta agagatcaag ctgggaggat gaactattac tggaccttgc | 780 |
| taaaacccgg agacacaata tatttgagg caaatgaaa tctaatagca ccaatgtatg | 840 |
| ctttcgcact gagtagaggc tttgggtccg gcatcatcac ctcaaacgca tcaatgcatg | 900 |
| agtgtaacac gaagtgtcaa acacccctgg gagctataaa cagcagtctc ccttaccaga | 960 |
| atatacaccc agtcacaata ggagagtgcc caaaatacgt caggagtgcc aaattgagga | 1020 |
| tggttacagg actaaggaac attccgtcca ttcaatccag aggtctattt ggagccattg | 1080 |
| ccggttttat tgaaggggga tggactggaa tgatagatgg atggtatggt tatcatcatc | 1140 |
| agaatgaaca gggatcaggc tatgcagcgg atcaaaaaag cacacaaaat gccattaacg | 1200 |
| ggattacaaa caaggtgaac actgttatcg agaaaatgaa cattcaattc acagctgtgg | 1260 |
| gtaaagaatt caacaaatta gaaaaaagga tggaaatttt aaataaaaa gttgatgatg | 1320 |
| gatttctgga catttggaca tataatgcag aattgttagt tctactggaa atgaaagga | 1380 |
| ctctggattt ccatgactca aatgtgaaga atctgtatga aaagtaaaa agccaattaa | 1440 |
| agaataatgc caaagaaatc ggaaatggat gttttgagtt ctaccacaag tgtgacaatg | 1500 |
| aatgcatgga aagtgtaaga aatgggactt atgattatcc caaatattca gaagagtcaa | 1560 |
| agttgaacag ggaaaaggta gatggagtga aattggaatc aatggggatc tatcagattc | 1620 |
| tggcgatcta ctcaactgtc gccagttcac tggtgctttt ggtctccctg ggggcaatca | 1680 |
| gtttctggat gtgttctaat ggatctttgc agtgcagaat atgcatctga gattagaatt | 1740 |
| tcagagatat gaggaaaaac accttgttt ctact | 1775 |

<210> SEQ ID NO 8
<211> LENGTH: 1413
<212> TYPE: DNA
<213> ORGANISM: Influenza virus

<400> SEQUENCE: 8

| | |
|---|---:|
| agcaaaagca ggggtttaaa atgaatccaa atcagaaaat aataaccatt ggatcaatct | 60 |
| gtctggtagt cggactaatt agcctaatat tgcaatagg aatataatc tcaatatgga | 120 |
| ttagccattc aattcaaact ggaagtcaaa accatactgg aatatgcaac caaaacatca | 180 |
| ttacctataa aaatagcacc tgggtaaagg acacaacttc agtgatatta accggcaatt | 240 |
| catctctttg tcccatccgt gggtgggcta tatacagcaa agacaatagc ataagaattg | 300 |
| gttccaaagg agacgttttt gtcataagag agccctttat ttcatgttct cacttggaat | 360 |
| gcaggacctt ttttctgacc caaggtgcct tactgaatga caagcattca agtgggactg | 420 |

```
ttaaggacag aagcccttat agggccttaa tgagctgccc tgtcggtgaa gctccgtccc    480
cgtacaattc aagatttgaa tcggttgctt ggtcagcaag tgcatgtcat gatggcatgg    540
gctggctaac aatcggaatt tcaggtccag ataatggagc agtggctgta ttaaaataca    600
acggcataat aactgaaacc ataaaaagtt ggaggaagaa atatattgagg acacaagagt    660 ctgaatgtgc ctgtgtaaat ggttcatgtt ttactataat gactgatggc ccgagtgatg    720
ggctggcctc gtacaaaatt ttcaagatcg aaaaggggaa ggttactaaa tcaatagagt    780
tgaatgcacc taattctcac tatgaggaat gttcctgtta ccctgatacc ggcaaagtga    840
tgtgtgtgtg cagagacaat tggcatggtt cgaaccggcc atgggtgtct ttcgatcaaa    900
acctggatta tcaaatagga tacatctgca gtggggtttt cggtgacaac ccgcgtcccg    960
aagatggaac aggcagctgt ggtccagtgt atgttgatgg agcaaacgga gtaaagggat    1020
tttcatatag gtatggtaat ggtgtttgga taggaaggac caaaagtcac agttccagac    1080
atgggtttga gatgatttgg gatcctaatg gatggacaga gactgatagt aagttctctg    1140
tgaggcaaga tgttgtggca atgactgatt ggtcagggta tagcggaagt ttcgttcaac    1200
atcctgagct gacagggcta gactgtatga ggccgtgctt ctgggttgaa ttaatcaggg    1260
gacgacctaa agaaaaaaca atctggacta gtgcgagcag catttctttt tgtggcgtga    1320
atagtgatac tgtagattgg tcttggccag acggtgctga gttgccattc agcattgaca    1380
agtagtctgt tcaaaaaact ccttgtttct act                                  1413

<210> SEQ ID NO 9
<400> SEQUENCE: 9

000

<210> SEQ ID NO 10
<211> LENGTH: 2341
<212> TYPE: DNA
<213> ORGANISM: Influenza virus

<400> SEQUENCE: 10
agcgaaagca ggcaaaccat ttgaatggat gtcaatccga ccttactttt cttaaaagtg    60
ccagcacaaa atgctataag cacaactttc ccttataccg agacccctcc ttacagccat    120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaagcaatg    300
gctttccttg aggaatccca tcctggtatt tttgaaaact cgtgtattga acgatggag     360 gttgttcagc aaacacgagt agacaagctg acacaaggcc gacagaccta tgactggact    420
ttaaatagaa accagcctgc tgcaacagca ttggccaaca ataagaagt gttcagatca     480 aatggcctca cggccaatga tcaggaagg ctcatagact tccttaagga tgtaatggag     540
tcaatgaaaa aagaagaaat ggggatcaca actcatttc agagaaagag acgggtgaga     600
gacaatatga ctaagaaaat gataacacag aaacaatag gtaaaggaa acagagattg     660 aacaaaaggg gttatctaat tagagcattg accctgaaca caatgaccaa agatgctgag     720
agagggaagc taaacgag agcaattgca accccaggga tgcaataag ggggtttgta       780 tactttgttg agacactggc aaggagtata tgtgagaac ttgaacaatc agggttgcca     840
gttggaggca atgagaagaa agcaaagttg gcaaatgttg taaggaagat gatgaccaat     900
```

```
tctcaggaca ccgaactttc tttcaccatc actggagata acaccaaatg gaacgaaaat    960
cagaatcctc ggatgttttt ggccatgatc acatatatga ccagaaatca gcccgaatgg   1020
ttcagaaatg ttctaagtat tgctccaata atgttctcaa acaaaatggc gagactggga   1080
aaagggtata tgtttgagag caagagtatg aaacttagaa ctcaaatacc tgcagaaatg   1140
ctagcaagca ttgatttgaa atatttcaat gattcaacaa gaagaagat tgaaaaaatc    1200 cgaccgctct taatagaggg gactgcatca ttgagccctg aatgatgat gggcatgttc    1260 aatatgttaa gcactgtatt aggcgtctcc atcctgaatc ttggacaaaa gagatacacc   1320
aagactactt actggtggga tggtcttcaa tcctctgacg attttgctct gattgtgaat   1380
gcacccaatc atgaagggat tcaagccgga gtcgacaggt tttatcgaac ctgtaagcta   1440
cttggaatca atatgagcaa gaaaaagtct tacataaaca gaacaggtac atttgaattc   1500
acaagttttt tctatcgtta tgggtttgtt gccaatttca gcatggagct tcccagtttt   1560
ggggtgtctg gatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat agaggtgaca cacaaataca aacccgaaga   1740
tcatttgaaa taagaaact gtgggagcaa acccgttcca aagctggact gctggtctcc    1800
gacggaggcc caaatttata caacattaga atctccaca ttcctgaagt ctgcctaaaa    1860
tgggaattga tggatgagga ttaccagggg cgtttatgca cccactgaa cccatttgtc    1920 agccataaag aaattgaatc aatgaacaat gcagtgatga tgccagcaca tggtccagcc   1980
aaaaacatgg agtatgatgc tgttgcaaca acacactcct ggatcccaa agaaatcga    2040 tccatcttga atacaagtca agaggagta cttgaagatg aacaaatgta ccaaaggtgc   2100
tgcaatttat ttgaaaaatt cttccccagc agttcataca aagaccagt cgggatatcc   2160 agtatggtgg aggctatggt ttccagagcc cgaattgatg cacggattga tttcgaatct   2220
ggaaggataa agaaagaaga gttcactgag atcatgaaga tctgttccac cattgaagag   2280
ctcagacggc aaaaatagtg aatttagctt gtccttcatg aaaaaatgcc ttgtttctac   2340
t                                                                    2341

<210> SEQ ID NO 11
<211> LENGTH: 2341
<212> TYPE: DNA
<213> ORGANISM: Influenza virus

<400> SEQUENCE: 11
agcgaaagca ggtcaattat attcaatatg gaaagaataa agaactaag aaatctaatg     60 tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg atcagaccg agtgatggta    300 tcacctctgg ctgtgacatg gtggaatagg aatggaccaa tgacaaatac agttcattat    360
ccaaaaatct acaaaactta ttttgaaaga gtcgaaaggc taaagcatgg aaccttggc    420 cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
```

```
gaactccagg attgcaaaat ttctcctttg atggttgcat acatgttgga gagagaactg      660
gtccgcaaaa cgagattcct cccagtggct ggtggaacaa gcagtgtgta cattgaagtg      720
ttgcatttga ctcaaggaac atgctgggaa cagatgtata ctccaggagg ggaagtgaag      780
aatgatgatg ttgatcaaag cttgattatt gctgctagga acatagtgag aagagctgca      840
gtatcagcag acccactagc atctttattg agatgtgcc acagcacaca gattggtgga       900
attaggatgg tagacatcct taagcagaac ccaacagaag agcaagccgt ggatatatgc      960
aaggctgcaa tgggactgag aattagctca tccttcagtt ttggtggatt cacatttaag     1020
agaacaagcg gatcatcagt caagagagag gaagaggtgc ttacgggcaa tcttcaaaca     1080
ttgaagataa gagtgcatga gggatctgaa gagttcacaa tggttgggag aagagcaaca     1140
gccatactca gaaaagcaac caggagattg attcagctga tagtgagtgg agagacgaa      1200
cagtcgattg ccgaagcaat aattgtggcc atggtatttt cacaagagga ttgtatgata     1260
aaagcagtta gaggtgatct gaatttcgtc aataggcga atcagcgact gaatcctatg      1320
catcaacttt taagacattt tcagaaggat gcgaaagtgc tttttcaaaa ttggggagtt     1380
gaacctatcg acaatgtgat gggaatgatt gggatattgc ccgacatgac tccaagcatc     1440
gagatgtcaa tgagaggagt gagaatcagc aaaatgggtg tagatgagta ctccagcacg     1500
gagagggtag tggtgagcat tgaccggttc ttgagagtca gggaccaacg aggaaatgta     1560
ctactgtctc ccgaggaggt cagtgaaaca caggaacaga gaaactgac aataacttac       1620
tcatcgtcaa tgatgtggga gattaatggt cctgaatcag tgttggtcaa tacctatcaa      1680
tggatcatca gaaactggga aactgttaaa attcagtggt cccagaaccc tacaatgcta      1740
tacaataaaa tggaatttga accatttcag tctttagtac ctaaggccat tagaggccaa     1800
tacagtgggt ttgtaagaac tctgttccaa caaatgaggg atgtgcttgg gacatttgat     1860
accgcacaga taataaaact tcttcccttc gcagccgctc caccaaagca agtagaatg      1920
cagttctcct catttactgt gaatgtgagg ggatcaggaa tgagaatact tgtaaggggc     1980
aattctcctg tattcaacta caacaaggcc acgaagagac tcacagttct cggaaaggat     2040
gctggcactt taaccgaaga cccagatgaa ggcacagctg agtggagtc cgctgttctg      2100
aggggattcc tcattctggg caaagaagac aggagatatg ggccagcatt aagcatcaat     2160
gaactgagca accttgcgaa aggagagaag gctaatgtgc taattgggca aggagacgtg     2220
gtgttggtaa tgaaacgaaa acgggactct agcatactta ctgacagcca gacagcgacc     2280
aaaagaattc ggatggccat caattagtgt cgaatagttt aaaaacgacc ttgtttctac     2340
t                                                                    2341

<210> SEQ ID NO 12
<211> LENGTH: 2233
<212> TYPE: DNA
<213> ORGANISM: Influenza virus

<400> SEQUENCE: 12
agcgaaagca ggtactgatt caaaatggaa gattttgtgc gacaatgctt caatccgatg        60
attgtcgagc ttgcggaaaa acaatgaaa gagtatgggg aggacctgaa atcgaaaca         120
aacaaatttg cagcaatatg cactcacttg gaagtatgct tcatgtattc agatttccac       180
ttcatcaatg agcaaggcga gtcaataatc gtagaacttg gtgatccaa tgcacttttg        240
aagcacagat ttgaaataat cgagggaaga gatcgcacaa tggcctggac agtagtaaac       300
agtatttgca acactacagg ggctgagaaa ccaaagtttc taccagattt gtatgattac       360
```

```
aaggaaaata gattcatcga aattggagta acaaggagag aagttcacat atactatctg        420
gaaaaggcca ataaaattaa atctgagaaa acacacatcc acattttctc gttcactggg        480
gaagaaatgg ccacaagggc cgactacact ctcgatgaag aaagcagggc taggatcaaa        540
accaggctat tcaccataag acaagaaatg gccagcagag gcctctggga ttcctttcgt        600
cagtccgaga gaggagaaga gacaattgaa gaaaggtttg aaatcacagg aacaatgcgc        660
aagcttgccg accaaagtct cccgccgaac ttctccagcc ttgaaaattt tagagcctat        720
gtggatggat tcgaaccgaa cggctacatt gagggcaagc tgtctcaaat gtccaaagaa        780
gtaaatgcta gaattgaacc tttttgaaa acaacaccac gaccacttag acttccgaat        840
gggcctccct gttctcagcg gtccaaattc ctgctgatgg atgccttaaa attaagcatt        900
gaggacccaa gtcatgaagg agagggaata ccgctatatg atgcaatcaa atgcatgaga        960
acattctttg gatggaagga acccaatgtt gttaaaccac acgaaagggg aataaatcca       1020
aattatcttc tgtcatggaa gcaagtactg gcagaactgc aggacattga gaatgaggag       1080
aaaattccaa agactaaaaa tatgaaaaaa acaagtcagc taaagtgggc acttggtgag       1140
aacatggcac cagaaaaggt agactttgac gactgtaaag atgtaggtga tttgaagcaa       1200
tatgatagtg atgaaccaga attgaggtcg cttgcaagtt ggattcagaa tgagttcaac       1260
aaggcatgcg aactgacaga ttcaagctgg atagagcttg atgagattgg agaagatgtg       1320
gctccaattg aacacattgc aagcatgaga aggaattatt tcacatcaga ggtgtctcac       1380
tgcagagcca cagaatacat aatgaagggg gtgtacatca atactgcctt acttaatgca       1440
tcttgtgcag caatggatga tttccaatta attccaatga taagcaagtg tagaactaag       1500
gagggaaggc gaaagaccaa cttgtatggt ttcatcataa aaggaagatc ccacttaagg       1560
aatgacaccg acgtggtaaa cttgtgagc atggagtttt ctctcactga cccaagactt       1620
gaaccacaca aatgggagaa gtactgtgtt cttgagatag agatatgct tctaagaagt       1680 gccataggcc aggtttcaag gcccatgttc ttgtatgtga ggacaaatgg aacctcaaaa       1740
attaaaatga aatgggggaat ggagatgagg cgttgtctcc tccagtcact tcaacaaatt       1800
gagagtatga ttgaagctga gtcctctgtc aaagagaaag acatgaccaa agagttcttt       1860
gagaacaaat cagaaacatg gcccattgga gagtctccca aaggagtgga ggaaagttcc       1920
attgggaagg tctgcaggac tttattagca aagtcggtat taacagcttg tatgcatct         1980 ccacaactag aaggatttc agctgaatca agaaaactgc ttcttatcgt tcaggctctt       2040
agggacaatc tggaacctgg gacctttgat cttggggggc tatatgaagc aattgaggag       2100
tgcctaatta atgatccctg ggttttgctt aatgcttctt ggttcaactc cttccttaca       2160
catgcattga gttagttgtg gcagtgctac tatttgctat ccatactgtc caaaaagta       2220 ccttgtttct act                                                           2233
```

<210> SEQ ID NO 13  
<211> LENGTH: 1565  
<212> TYPE: DNA  
<213> ORGANISM: Influenza virus

<400> SEQUENCE: 13

```
agcaaaagca gggtagataa tcactcactg agtgacatca aaatcatggc gtcccaaggc          60
accaaacggt cttacgaaca gatggagact gatggagaac gccagaatgc cactgaaatc         120
agagcatccg tcggaaaaat gattggtgga attggacgat tctacatcca aatgtgcaca         180
```

```
gaacttaaac tcagtgatta tgagggacgg ttgatccaaa acagcttaac aatagagaga      240
atggtgctct ctgcttttga cgaaaggaga aataaatacc tggaagaaca tcccagtgcg      300
gggaaagatc ctaagaaaac tggaggacct atatacagaa gagtaaacgg aaagtggatg      360
agagaactca tcctttatga caagaagaa ataaggcgaa tctggcgcca agctaataat       420
ggtgacgatg caacggctgg tctgactcac atgatgatct ggcattccaa tttgaatgat      480
gcaacttatc agaggacaag ggctcttgtt cgcaccggaa tggatcccag gatgtgctct      540
ctgatgcaag gttcaactct ccctaggagg tctggagccg caggtgctgc agtcaaagga      600
gttggaacaa tggtgatgga attggtcagg atgatcaaac gtgggatcaa tgatcggaac      660
ttctggaggg gtgagaatgg acgaaaaaca agaattgctt atgaaagaat gtgcaacatt      720
ctcaaaggga aatttcaaac tgctgcacaa aaagcaatga tggatcaagt gagagagagc      780
cggaacccag ggaatgctga gttcgaagat ctcacttttc tagcacggtc tgcactcata      840
ttgagagggt cggttgctca caagtcctgc ctgcctgcct gtgtgtatgg acctgccgta      900
gccagtgggt acgactttga agagaggga tactctctag tcggaataga cccttcaga       960 ctgcttcaaa acagccaagt gtacagccta atcagaccaa atgagaatcc agcacacaag     1020
agtcaactgg tgtggatggc atgccattct gccgcatttg aagatctaag agtattgagc     1080
ttcatcaaag gacgaaggt ggtcccaaga gggaagcttt ccactagagg agttcaaatt      1140
gcttccaatg aaaatatgga gactatgaa tcaagtacac ttgaactgag aagcaggtac       1200
tgggccataa ggaccagaag tggaggaaac accaatcaac agagggcatc tgcgggccaa     1260 atcagctac aacctacgtt ctcagtacag agaaatctcc cttttgacag aacaaccgtt      1320
atggcagcat tcactgggaa tacagagggg agaacatctg acatgaggac cgaaatcata     1380
aggatgatgg aaagtgcaag accagaagat gtgtctttcc aggggcgggg agtcttcgag     1440
ctctcggacg aaaaggcagc gagcccgatc gtgccttcct ttgacatgag taatgaagga     1500
tcttatttct tcggagacaa tgcagaggag tacgacaatt aaagaaaaat accttgtttc     1560
tact                                                                   1565

<210> SEQ ID NO 14
<211> LENGTH: 1027
<212> TYPE: DNA
<213> ORGANISM: Influenza virus

<400> SEQUENCE: 14
agcaaaagca ggtagatatt gaaagatgag tcttctaacc gaggtcgaaa cgtacgttct       60
ctctatcatc ccgtcaggcc ccctcaaagc cgagatcgca cagagacttg aagatgtctt      120
tgcagggaag aacaccgatc ttgaggttct catggaatgg ctaaagacaa gaccaatcct      180
gtcacctctg actaagggga ttttaggatt tgtgttcacg ctcaccgtgc ccagtgagcg      240
aggactgcag cgtagacgct ttgtccaaaa tgcccttaat gggacggggg atccaaataa      300
catggacaaa gcagttaaac tgtataggaa gctcaagagg gagataacat tccatgggc      360 caaagaaatc tcactcagtt attctgctgg tgcacttgcc agttgtatgg gcctcatata      420
caacaggatg ggggctgtga ccactgaagt ggcatttggc ctggtatgtg caacctgtga      480
acagattgct gactcccagc atcggtctca taggcaaatg gtgacaacaa ccaacccact      540
aatcagacat gagaacagaa tggttttagc cagcactaca gctaaggcta tggagcaaat      600
ggctggatcg agtgagcaag cagcagaggc catggaggtt gctagtcagg ctaggcaaat      660
ggtgcaagcg atgagaacca ttgggactca tcctagctcc agtgctggtc tgaaaaatga      720
```

```
tcttcttgaa aatttgcagg cctatcagaa acgaatgggg gtgcagatgc aacggttcaa    780
gtgatcctct cgctattgcc gcaaatatca ttgggatctt gcacttgata ttgtggattc    840
ttgatcgtct ttttttcaaa tgcatttacc gtcgctttaa atacggactg aaaggagggc    900
cttctacgga aggagtgcca aagtctatga gggaagaata tcgaaaggaa cagcagagtg    960
ctgtggatgc tgacgatggt cattttgtca gcatagagct ggagtaaaaa actaccttgt   1020
ttctact                                                              1027
```

<210> SEQ ID NO 15
<211> LENGTH: 890
<212> TYPE: DNA
<213> ORGANISM: Influenza virus

<400> SEQUENCE: 15

```
agcaaaagca gggtgacaaa gacataatgg atccaaacac tgtgtcaagc tttcaggtag     60
attgctttct ttggcatgtc cgcaaacgag ttgcagacca agaactaggt gatgccccat    120
tccttgatcg gcttcgccga gatcagaaat ccctaagagg aaggggcagc actcttggtc    180
tggacatcga gacagccaca cgtgctggaa agcagatagt ggagcggatt ctgaaagaag    240
aatccgatga ggcacttaaa atgaccatgg cctctgtacc tgcgtcgcgt tacctaaccg    300
acatgactct tgaggaaatg tcaagggaat ggtccatgct catacccaag cagaaagtgg    360
caggccctct ttgtatcaga atggaccagg cgatcatgga taaaaacatc atactgaaag    420
cgaacttcag tgtgattttt gaccggctgg agactctaat attgctaagg ctttcaccg     480 aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcggaac aattaggtca gaagtttgaa    720
gaaataagat ggttgattga agaagtgaga cacaaactga aggtaacaga gaatagtttt    780
gagcaaataa catttatgca agccttacat ctattgcttg aagtggagca agagataaga    840
actttctcat ttcagcttat ttaataataa aaaacaccct tgtttctact                890
```

<210> SEQ ID NO 16
<211> LENGTH: 319
<212> TYPE: PRT
<213> ORGANISM: Influenza virus

<400> SEQUENCE: 16

```
Ala Thr Leu Cys Leu Gly His His Ala Val Pro Asn Gly Thr Leu Val
1               5                   10                  15

Lys Thr Ile Thr Asp Asp Gln Ile Glu Val Thr Asn Ala Thr Glu Leu
            20                  25                  30

Val Gln Ser Ser Ser Thr Gly Lys Ile Cys Asn Asn Pro His Arg Ile
        35                  40                  45

Leu Asp Gly Ile Asp Cys Thr Leu Ile Asp Ala Leu Leu Gly Asp Pro
    50                  55                  60

His Cys Asp Val Phe Gln Asn Glu Thr Trp Asp Leu Phe Val Glu Arg
65                  70                  75                  80

Ser Lys Ala Phe Ser Asn Cys Tyr Pro Tyr Asp Val Pro Asp Tyr Ala
                85                  90                  95

Ser Leu Arg Ser Leu Val Ala Ser Ser Gly Thr Leu Glu Phe Ile Thr
            100                 105                 110
```

-continued

```
Glu Gly Phe Thr Trp Thr Gly Val Thr Gln Asn Gly Gly Ser Asn Ala
        115                 120                 125

Cys Lys Arg Gly Pro Gly Ser Gly Phe Phe Ser Arg Leu Asn Trp Leu
130                 135                 140

Thr Lys Ser Gly Ser Thr Tyr Pro Val Leu Asn Val Thr Met Pro Asn
145                 150                 155                 160

Asn Asp Asn Phe Asp Lys Leu Tyr Ile Trp Gly Ile His His Pro Ser
                165                 170                 175

Thr Asn Gln Glu Gln Thr Ser Leu Tyr Val Gln Ala Ser Gly Arg Val
            180                 185                 190

Thr Val Ser Thr Arg Arg Ser Gln Gln Thr Ile Ile Pro Asn Ile Gly
        195                 200                 205

Ser Arg Pro Trp Val Arg Gly Leu Ser Ser Arg Ile Ser Ile Tyr Trp
    210                 215                 220

Thr Ile Val Lys Pro Gly Asp Val Leu Val Ile Asn Ser Asn Gly Asn
225                 230                 235                 240

Leu Ile Ala Pro Arg Gly Tyr Phe Lys Met Arg Thr Gly Lys Ser Ser
                245                 250                 255

Ile Met Arg Ser Asp Ala Pro Ile Asp Thr Cys Ile Ser Glu Cys Ile
            260                 265                 270

Thr Pro Asn Gly Ser Ile Pro Asn Asp Lys Pro Phe Gln Asn Val Asn
        275                 280                 285

Lys Ile Thr Tyr Gly Ala Cys Pro Lys Tyr Val Lys Gln Asn Thr Leu
    290                 295                 300

Lys Leu Ala Thr Gly Met Arg Asn Val Pro Glu Lys Gln Thr Arg
305                 310                 315

<210> SEQ ID NO 17
<211> LENGTH: 326
<212> TYPE: PRT
<213> ORGANISM: Influenza virus

<400> SEQUENCE: 17

Asp Gln Ile Cys Ile Gly Tyr His Ala Asn Asn Ser Thr Glu Gln Val
1               5                   10                  15

Asp Thr Ile Met Glu Lys Asn Ile Thr Val Thr His Ala Gln Asp Ile
            20                  25                  30

Leu Glu Lys Thr His Asn Gly Lys Leu Cys Asp Leu Asn Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Leu Asn Val Pro Glu Trp Ser Tyr Ile Val
65                  70                  75                  80

Glu Lys Asp Asn Pro Val Asn Gly Leu Cys Tyr Pro Glu Asn Phe Asn
                85                  90                  95

Asp Tyr Glu Glu Leu Lys His Leu Leu Ser Ser Thr Asn His Phe Glu
            100                 105                 110

Lys Ile Arg Ile Ile Pro Arg Ser Ser Trp Ser Asn His Asp Ala Ser
        115                 120                 125

Ser Gly Val Ser Ser Ala Cys Pro Tyr Asn Gly Arg Ser Ser Phe Phe
    130                 135                 140

Arg Asn Val Val Trp Leu Ile Lys Lys Asn Asn Ala Tyr Pro Thr Ile
145                 150                 155                 160

Lys Arg Ser Tyr Asn Asn Thr Asn Gln Glu Asp Leu Leu Ile Leu Trp
```

```
                165                 170                 175
Gly Ile His His Pro Asn Asp Ala Ala Glu Gln Thr Lys Leu Tyr Gln
            180                 185                 190

Asn Pro Thr Thr Tyr Val Ser Val Gly Thr Ser Thr Leu Asn Gln Arg
            195                 200                 205

Ser Ile Pro Glu Ile Ala Thr Arg Pro Lys Val Asn Gly Gln Ser Gly
            210                 215                 220

Arg Met Glu Phe Tyr Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Gly Ser Ala Ile Met Lys Ser Gly Leu Glu Tyr Gly
                260                 265                 270

Asn Cys Asn Thr Lys Cys Gln Thr Pro Met Gly Ala Ile Asn Ser Ser
            275                 280                 285

Met Pro Phe His Asn Val His Pro Leu Thr Ile Gly Glu Cys Pro Lys
            290                 295                 300

Tyr Val Lys Ser Gly Arg Leu Val Leu Ala Thr Gly Leu Arg Asn Val
305                 310                 315                 320

Pro Gln Arg Glu Thr Arg
                325

<210> SEQ ID NO 18
<211> LENGTH: 330
<212> TYPE: PRT
<213> ORGANISM: Influenza virus

<400> SEQUENCE: 18

Asp Gln Ile Cys Ile Gly Tyr His Ala Asn Asn Ser Thr Glu Gln Val
1               5                   10                  15

Asp Thr Ile Met Glu Lys Asn Ile Thr Val Thr His Ala Gln Asp Ile
            20                  25                  30

Leu Glu Arg Thr His Asn Gly Lys Leu Cys Asp Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Ser Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asn His Asp Ala Ser
        115                 120                 125

Ser Gly Val Ser Ser Ala Cys Pro Tyr Leu Gly Arg Ser Ser Phe Phe
    130                 135                 140

Arg Asn Val Val Trp Leu Ile Lys Lys Asn Ser Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Val Ser Val Gly Thr Ser Thr Leu Asn Gln Arg
            195                 200                 205
```

```
Leu Ile Pro Glu Ile Ala Thr Arg Pro Lys Val Asn Gly Gln Ser Gly
    210                 215                 220
Arg Met Glu Phe Tyr Trp Thr Ile Leu Lys Pro Asn Asp Ala Ile Asn
225                 230                 235                 240
Phe Glu Ser Asn Gly Asn Phe Ile Ala Pro Glu Tyr Ala Tyr Lys Ile
                245                 250                 255
Val Lys Lys Gly Asp Ser Thr Ile Met Lys Ser Glu Leu Glu Tyr Gly
                260                 265                 270
Asn Cys Asn Thr Lys Cys Gln Thr Pro Met Gly Ala Ile Asn Ser Ser
            275                 280                 285
Met Pro Phe His Asn Val His Pro Leu Thr Ile Gly Glu Cys Pro Lys
290                 295                 300
Tyr Val Lys Ser Asn Arg Leu Val Leu Ala Thr Gly Leu Arg Asn Thr
305                 310                 315                 320
Pro Gln Arg Glu Arg Arg Lys Lys Arg
                325                 330

<210> SEQ ID NO 19
<211> LENGTH: 325
<212> TYPE: PRT
<213> ORGANISM: Influenza virus

<400> SEQUENCE: 19

Asp Lys Ile Cys Ile Gly Tyr Gln Ser Thr Asn Ser Thr Glu Thr Val
1               5                   10                  15
Asp Thr Leu Met Glu Thr Asn Ile Pro Val Thr His Ala Lys Asp Ile
                20                  25                  30
Leu His Thr Glu His Asn Gly Met Leu Cys Ala Thr Asn Leu Gly His
            35                  40                  45
Pro Leu Ile Leu Asp Thr Cys Ser Ile Glu Gly Leu Ile Tyr Gly Asn
50                  55                  60
Pro Ser Cys Asp Leu Leu Leu Gly Gly Arg Glu Trp Ser Tyr Ile Val
65                  70                  75                  80
Glu Lys Pro Ser Pro Val Asn Gly Met Cys Tyr Pro Gly Asn Phe Glu
                85                  90                  95
Asn Leu Glu Glu Leu Lys His Leu Phe Ser Arg Ala Ser Ser Tyr Gln
                100                 105                 110
Arg Ile Gln Ile Ile Pro Asp Thr Ile Trp Asn His Ser Tyr Ser Ser
            115                 120                 125
Gly Thr Ser Arg Ala Cys Ser Asp Ser Phe Phe Arg Ser Met Arg Trp
        130                 135                 140
Leu Ile Gln Lys Asn Asn Ala Tyr Pro Thr Gln Asp Ala Gln Tyr Thr
145                 150                 155                 160
Asn Thr Arg Gly Lys Ser Ile Leu Val Met Trp Gly Ile Asn His Pro
                165                 170                 175
Pro Asp Asp Thr Val Gln Thr Asn Leu Tyr Thr Arg Thr Asp Thr Thr
                180                 185                 190
Thr Ser Val Thr Thr Glu Asp Ile Asn Arg Arg Phe Lys Pro Val Ile
            195                 200                 205
Ala Pro Arg Pro Leu Val Asn Gly Gln His Gly Arg Met Asp Tyr Tyr
        210                 215                 220
Trp Ser Ile Leu Lys Pro Asn Gln Thr Ile Arg Phe Arg Ser Asn Gly
225                 230                 235                 240
Asn Phe Ile Ala Pro Trp Tyr Ala His Ile Leu Ser Gly Glu Ser His
                245                 250                 255
```

```
Gly Arg Ile Leu Lys Thr Glu Leu Asn Ser Gly Asn Cys Asn Val Gln
            260                 265                 270

Cys Gln Thr Glu Arg Gly Gly Leu Asn Thr Thr Leu Pro Phe His Asn
        275                 280                 285

Val Ser Pro Tyr Ala Ile Gly Asn Cys Pro Lys Tyr Val Gly Val Lys
    290                 295                 300

Ser Leu Val Leu Ala Val Gly Leu Arg Asn Thr Pro Ala Arg Ser Ser
305                 310                 315                 320

Arg Arg Lys Lys Arg
                325

<210> SEQ ID NO 20
<211> LENGTH: 325
<212> TYPE: PRT
<213> ORGANISM: Influenza virus

<400> SEQUENCE: 20

Asp Lys Ile Cys Ile Gly Tyr Gln Ser Thr Asn Ser Thr Glu Thr Val
  1               5                  10                  15

Asp Thr Leu Met Glu Thr Asn Ile Pro Val Thr His Ala Lys Asp Ile
            20                  25                  30

Leu His Thr Glu His Asn Gly Met Leu Cys Ala Thr Ser Leu Gly His
        35                  40                  45

Pro Leu Ile Leu Asp Thr Cys Ser Ile Glu Gly Leu Val Tyr Gly Asn
    50                  55                  60

Pro Ser Cys Asp Leu Leu Leu Gly Gly Arg Glu Trp Ser Tyr Ile Val
65                  70                  75                  80

Glu Lys Pro Ser Pro Val Asn Gly Thr Cys Tyr Pro Gly Asn Phe Glu
                85                  90                  95

Asn Leu Glu Glu Leu Lys Thr Leu Phe Ser Arg Ala Ser Ser Tyr Gln
            100                 105                 110

Arg Ile Gln Ile Ile Pro Asp Thr Ile Trp Asn His Ser Tyr Thr Ser
        115                 120                 125

Gly Thr Ser Arg Ala Cys Ser Gly Ser Phe Phe Arg Ser Met Arg Trp
    130                 135                 140

Leu Ile Gln Lys Ser Gly Phe Tyr Pro Thr Gln Asp Ala Gln Tyr Thr
145                 150                 155                 160

Asn Thr Arg Gly Lys Ser Ile Leu Val Met Trp Gly Ile Asn His Pro
                165                 170                 175

Pro Asp Tyr Thr Val Gln Thr Asn Leu Tyr Thr Arg Asn Asp Thr Thr
            180                 185                 190

Thr Ser Val Thr Thr Glu Asp Leu Asn Arg Arg Phe Lys Pro Val Ile
        195                 200                 205

Ala Pro Arg Pro Leu Val Asn Gly Gln Gln Gly Arg Met Asp Tyr Tyr
    210                 215                 220

Trp Ser Ile Leu Lys Pro Asn Gln Thr Ile Arg Phe Arg Ser Asn Gly
225                 230                 235                 240

Asn Phe Ile Ala Pro Trp Tyr Ala His Val Leu Ser Gly Gly Ser His
                245                 250                 255

Gly Arg Ile Leu Lys Thr Glu Leu Lys Gly Gly Asn Cys Asn Val Gln
            260                 265                 270

Cys Gln Thr Glu Lys Gly Gly Leu Asn Ser Thr Leu Pro Phe His Asn
        275                 280                 285

Val Ser Pro Tyr Ala Ile Gly Thr Cys Pro Lys Tyr Val Arg Val Lys
```

```
                 290                 295                 300
Ser Leu Val Leu Ala Val Gly Leu Arg Asn Thr Pro Ala Arg Ser Ser
305                 310                 315                 320

Arg Arg Lys Lys Arg
            325

<210> SEQ ID NO 21
<211> LENGTH: 566
<212> TYPE: PRT
<213> ORGANISM: Influenza virus

<400> SEQUENCE: 21

Met Lys Ala Ile Leu Val Val Leu Leu Tyr Thr Phe Ala Thr Ala Asn
  1               5                  10                  15

Ala Asp Thr Leu Cys Ile Gly Tyr His Ala Asn Asn Ser Thr Asp Thr
                 20                  25                  30

Val Asp Thr Val Leu Glu Lys Asn Val Thr Val Thr His Ser Val Asn
             35                  40                  45

Leu Leu Glu Asp Lys His Asn Gly Lys Leu Cys Lys Leu Arg Gly Val
 50                  55                  60

Ala Pro Leu His Leu Gly Lys Cys Asn Ile Ala Gly Trp Ile Leu Gly
 65                  70                  75                  80

Asn Pro Glu Cys Glu Ser Leu Ser Thr Ala Ser Ser Trp Ser Tyr Ile
                 85                  90                  95

Val Glu Thr Pro Ser Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
        290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335
```

```
Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 22
<211> LENGTH: 231
<212> TYPE: PRT
<213> ORGANISM: Influenza virus

<400> SEQUENCE: 22

Arg Asn Ile Pro Ser Ile Gln Ser Arg Gly Leu Phe Gly Ala Ile Ala
1               5                   10                  15

Gly Phe Ile Glu Gly Gly Trp Thr Gly Met Val Asp Gly Trp Tyr Gly
            20                  25                  30

Tyr His His Gln Asn Glu Gln Gly Ser Gly Tyr Ala Ala Asp Leu Lys
        35                  40                  45

Ser Thr Gln Asn Ala Ile Asp Glu Ile Thr Asn Lys Val Asn Ser Val
    50                  55                  60

Ile Glu Lys Met Asn Thr Gln Phe Thr Ala Val Gly Lys Glu Phe Asn
65                  70                  75                  80

His Leu Glu Lys Arg Ile Glu Asn Leu Asn Lys Lys Val Asp Asp Gly
                85                  90                  95

Phe Leu Asp Ile Trp Thr Tyr Asn Ala Glu Leu Leu Val Leu Leu Glu
            100                 105                 110

Asn Glu Arg Thr Leu Asp Tyr His Asp Ser Asn Val Lys Asn Leu Tyr
        115                 120                 125

Glu Lys Val Arg Ser Gln Leu Lys Asn Asn Ala Lys Glu Ile Gly Asn
    130                 135                 140
```

```
Gly Cys Phe Glu Phe Tyr His Lys Cys Asp Asn Thr Cys Met Glu Ser
145                 150                 155                 160

Val Lys Asn Gly Thr Tyr Asp Tyr Pro Lys Tyr Ser Glu Glu Ala Lys
                165                 170                 175

Leu Asn Arg Glu Glu Ile Asp Gly Val Lys Leu Glu Ser Thr Arg Ile
            180                 185                 190

Tyr Gln Ile Leu Ala Ile Tyr Ser Thr Val Ala Ser Ser Leu Val Leu
        195                 200                 205

Val Val Ser Leu Gly Ala Ile Ser Phe Trp Met Cys Ser Asn Gly Ser
    210                 215                 220

Leu Gln Cys Arg Ile Cys Ile
225                 230

<210> SEQ ID NO 23
<211> LENGTH: 221
<212> TYPE: PRT
<213> ORGANISM: Influenza virus

<400> SEQUENCE: 23

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
                20                  25                  30

Gly Gln Ala Ala Asp Leu Lys Ser Thr Gln Ala Ala Ile Asp Gln Ile
            35                  40                  45

Asn Gly Lys Leu Asn Arg Val Ile Glu Lys Thr Asn Glu Lys Phe His
50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Glu Met Gly Asn Gly Cys Phe Lys Ile Tyr His Lys Cys
130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Arg Gly Asn Ile Arg Cys Asn Ile Cys Ile
210                 215                 220

<210> SEQ ID NO 24
<211> LENGTH: 222
<212> TYPE: PRT
<213> ORGANISM: Influenza virus

<400> SEQUENCE: 24

Gly Leu Phe Gly Ala Ile Ala Gly Phe Ile Glu Gly Gly Trp Gln Gly
1               5                   10                  15
```

```
Met Ile Asp Gly Trp Tyr Gly Phe His His Ser Asn Glu Gln Gly Ser
             20                  25                  30

Gly Tyr Ala Ala Asp Lys Glu Ser Thr Gln Lys Ala Ile Asp Gly Thr
                 35                  40                  45

Thr Asn Lys Val Asn Ser Val Ile Asp Lys Met Asn Thr Gln Phe Glu
 50                  55                  60

Ala Ile Gly Lys Glu Phe Asn Asn Leu Glu Arg Arg Ile Glu Asn Leu
 65                  70                  75                  80

Asn Lys Lys Met Glu Asp Gly Phe Leu Asp Val Trp Thr Tyr Asn Ala
                 85                  90                  95

Glu Leu Leu Val Leu Met Glu Asn Glu Arg Thr Leu Asp Phe His Asp
                100                 105                 110

Ser Asn Val Lys Asn Leu Phe Asp Lys Val Arg Leu Gln Leu Arg Asp
                115                 120                 125

Asn Ala Lys Glu Leu Gly Asn Gly Cys Phe Glu Phe Tyr His Lys Cys
130                 135                 140

Asp Asn Glu Cys Met Glu Ser Ile Lys Asn Gly Thr Tyr Asp Tyr Pro
145                 150                 155                 160

Gln Tyr Ser Glu Glu Ala Arg Leu Asn Arg Glu Glu Ile Ser Gly Val
                165                 170                 175

Lys Leu Glu Ser Met Gly Ile Tyr Gln Ile Leu Ser Ile Tyr Ser Thr
                180                 185                 190

Val Ala Ser Ser Leu Ala Leu Ala Val Met Ile Ala Gly Leu Ser Leu
                195                 200                 205

Trp Met Cys Ser Asn Gly Ser Leu Gln Cys Arg Ile Cys Ile
                210                 215                 220

<210> SEQ ID NO 25
<211> LENGTH: 222
<212> TYPE: PRT
<213> ORGANISM: Influenza virus

<400> SEQUENCE: 25

Gly Leu Phe Gly Ala Ile Ala Gly Phe Ile Glu Gly Gly Trp Gln Gly
 1               5                  10                  15

Met Ile Asp Gly Trp Tyr Gly Phe His His Ser Asn Glu Gln Gly Ser
             20                  25                  30

Gly Tyr Ala Ala Asp Lys Glu Ser Thr Gln Lys Ala Ile Asp Gly Thr
                 35                  40                  45

Thr Asn Lys Val Asn Ser Val Ile Asn Lys Met Asn Thr Gln Phe Glu
 50                  55                  60

Ala Ile Gly Arg Glu Phe Asn Asn Leu Glu Arg Arg Ile Glu Asn Leu
 65                  70                  75                  80

Asn Lys Lys Met Glu Asp Gly Phe Leu Asp Val Trp Thr Tyr Asn Ala
                 85                  90                  95

Glu Leu Leu Val Leu Met Glu Asn Glu Arg Thr Leu Asp Phe His Asp
                100                 105                 110

Ser Asn Val Lys Asn Leu Phe Asp Lys Val Arg Leu Gln Leu Arg Asp
                115                 120                 125

Asn Ala Lys Glu Leu Gly Asn Gly Cys Phe Glu Phe Tyr His Lys Cys
130                 135                 140

Asp Asn Glu Cys Met Glu Ser Ile Lys Asn Gly Thr Tyr Asp Tyr Pro
145                 150                 155                 160

Gln Tyr Ser Glu Glu Ala Arg Leu Asn Arg Glu Glu Ile Ser Gly Val
```

```
                    165                 170                 175

Lys Leu Glu Ser Met Gly Thr Tyr Gln Ile Leu Ser Ile Tyr Ser Thr
                180                 185                 190

Val Ala Ser Ser Leu Ala Leu Ala Val Met Val Ala Gly Leu Ser Leu
            195                 200                 205

Trp Met Cys Ser Asn Gly Ser Leu Gln Cys Arg Ile Cys Ile
        210                 215                 220

<210> SEQ ID NO 26
<211> LENGTH: 212
<212> TYPE: PRT
<213> ORGANISM: Influenza virus

<400> SEQUENCE: 26

Gly Leu Phe Gly Ala Ile Ala Gly Phe Ile Glu Gly Gly Trp Pro Gly
1               5                   10                  15

Leu Ile Ala Gly Trp Tyr Gly Phe Gln His Ser Asn Asp Gln Gly Val
            20                  25                  30

Gly Met Ala Ala Asp Arg Asp Ser Thr Gln Lys Ala Ile Asp Lys Thr
        35                  40                  45

Thr Ser Lys Val Asn Asn Val Ile Asp Lys Met Asn Lys Gln Phe Gly
    50                  55                  60

Ile Ile Asp His Glu Phe Asn Asn Leu Glu Thr Arg Leu Asn Met Ile
65                  70                  75                  80

Asn Asn Lys Met Asp Asp Gln Ile Gln Asp Ile Trp Thr Tyr Asn Ala
                85                  90                  95

Glu Leu Leu Val Leu Met Glu Asn Glu Lys Thr Leu Asp Glu His Asp
            100                 105                 110

Ala Asn Val Lys Asn Leu Phe Asn Lys Val Lys Leu Ala Leu Gly Ser
        115                 120                 125

Asn Ala Met Glu Asp Gly Lys Gly Cys Phe Glu Leu Tyr His Lys Cys
    130                 135                 140

Asp Asp Gln Cys Met Glu Thr Ile Lys Asn Gly Thr Tyr Asn Arg Arg
145                 150                 155                 160

Lys Tyr Lys Glu Glu Ser Lys Leu Glu Arg Gln Lys Ile Glu Gly Val
                165                 170                 175

Lys Leu Glu Ser Glu Gly Thr Tyr Lys Ile Leu Thr Ile Tyr Ser Thr
                180                 185                 190

Val Ala Ser Ser Leu Val Ile Ala Met Gly Phe Ala Ala Leu Leu Phe
            195                 200                 205

Trp Met Met Ser
        210

<210> SEQ ID NO 27
<211> LENGTH: 175
<212> TYPE: PRT
<213> ORGANISM: Influenza virus

<400> SEQUENCE: 27

Gly Leu Phe Gly Ala Ile Ala Gly Phe Ile Glu Gly Gly Trp Pro Gly
1               5                   10                  15

Leu Ile Ala Gly Trp Tyr Gly Phe Gln His Ser Asn Asp Gln Gly Val
            20                  25                  30

Gly Met Ala Ala Asp Arg Asp Ser Thr Gln Lys Ala Ile Asp Lys Thr
        35                  40                  45

Thr Ser Lys Val Asn Asn Val Ile Asp Lys Met Asn Lys Gln Phe Glu
```

```
            50                  55                  60
Ile Ile Asp His Glu Phe Asn Asn Leu Glu Thr Arg Leu Asn Met Ile
 65                  70                  75                  80

Asn Asn Lys Met Asp Asp Gln Ile Gln Asp Val Trp Ala Tyr Asn Ala
                 85                  90                  95

Glu Leu Leu Val Leu Met Glu Asn Glu Lys Thr Leu Asp Glu His Asp
                100                 105                 110

Ala Asn Val Lys Asn Leu Phe Asn Lys Val Lys Leu Ala Leu Gly Ser
            115                 120                 125

Asn Ala Met Glu Asp Gly Lys Gly Cys Phe Glu Leu Tyr His Lys Cys
130                 135                 140

Asp Asp Gln Cys Met Glu Thr Ile Lys Asn Gly Thr Tyr Asn Arg Arg
145                 150                 155                 160

Lys Tyr Lys Glu Glu Ser Arg Leu Glu Arg Gln Lys Ile Glu Gly
                165                 170                 175

<210> SEQ ID NO 28
<211> LENGTH: 222
<212> TYPE: PRT
<213> ORGANISM: Influenza virus

<400> SEQUENCE: 28

Gly Leu Phe Gly Ala Ile Ala Gly Phe Ile Glu Gly Gly Trp Thr Gly
 1                   5                  10                  15

Met Val Asp Gly Trp Tyr Gly Tyr His His Gln Asn Glu Gln Gly Ser
                 20                  25                  30

Gly Tyr Ala Ala Asp Gln Lys Ser Thr Gln Asn Ala Ile Asn Gly Ile
             35                  40                  45

Thr Asn Lys Val Asn Ser Val Ile Glu Lys Met Asn Thr Gln Phe Thr
 50                  55                  60

Ala Val Gly Lys Glu Phe Asn Lys Leu Glu Arg Arg Met Glu Asn Leu
 65                  70                  75                  80

Asn Lys Lys Val Asp Asp Gly Phe Leu Asp Ile Trp Thr Tyr Asn Ala
                 85                  90                  95

Glu Leu Leu Val Leu Leu Glu Asn Glu Arg Thr Leu Asp Phe His Asp
                100                 105                 110

Ser Asn Val Lys Asp Leu Tyr Glu Lys Val Lys Ser Gln Leu Lys Asn
            115                 120                 125

Asn Ala Lys Glu Ile Gly Asn Gly Cys Phe Glu Phe Tyr His Lys Cys
130                 135                 140

Asn Asn Glu Cys Met Glu Ser Val Lys Asn Gly Thr Tyr Asp Tyr Pro
145                 150                 155                 160

Lys Tyr Ser Glu Glu Ser Lys Leu Asn Arg Glu Lys Ile Asp Gly Val
                165                 170                 175

Lys Leu Glu Ser Met Gly Val Tyr Gln Ile Leu Ala Ile Tyr Ser Thr
            180                 185                 190

Val Ala Ser Ser Leu Val Leu Leu Val Ser Leu Gly Ala Ile Ser Phe
            195                 200                 205

Trp Met Cys Ser Asn Gly Ser Leu Gln Cys Arg Ile Cys Ile
210                 215                 220

<210> SEQ ID NO 29
<211> LENGTH: 222
<212> TYPE: PRT
<213> ORGANISM: Influenza virus
```

<400> SEQUENCE: 29

Gly Leu Phe Gly Ala Ile Ala Gly Phe Ile Glu Gly Gly Trp Thr Gly
1               5                   10                  15

Met Val Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asn Gly Ile
        35                  40                  45

Thr Asn Lys Val Asn Ser Val Ile Glu Lys Met Asn Thr Gln Phe Thr
    50                  55                  60

Ala Val Gly Lys Glu Phe Asn Lys Leu Glu Arg Arg Met Glu Asn Leu
65                  70                  75                  80

Asn Lys Lys Val Asp Asp Gly Phe Ile Asp Ile Trp Thr Tyr Asn Ala
                85                  90                  95

Glu Leu Leu Val Leu Leu Glu Asn Glu Arg Thr Leu Asp Phe His Asp
            100                 105                 110

Ser Asn Val Lys Asp Leu Tyr Glu Lys Val Lys Ser Gln Leu Lys Asn
        115                 120                 125

Asn Ala Lys Glu Ile Gly Asn Gly Cys Phe Glu Phe Tyr His Lys Cys
130                 135                 140

Asn Asp Glu Cys Met Glu Ser Val Lys Asn Gly Thr Tyr Asp Tyr Pro
145                 150                 155                 160

Lys Tyr Ser Glu Glu Ser Lys Leu Asn Arg Glu Lys Ile Asp Gly Val
                165                 170                 175

Lys Leu Glu Ser Met Gly Val Tyr Gln Ile Leu Ala Ile Tyr Ser Thr
            180                 185                 190

Val Ala Ser Ser Leu Val Leu Val Ser Leu Gly Ala Ile Ser Phe
        195                 200                 205

Trp Met Cys Ser Asn Gly Ser Leu Gln Cys Arg Ile Cys Ile
210                 215                 220

<210> SEQ ID NO 30
<211> LENGTH: 221
<212> TYPE: PRT
<213> ORGANISM: Influenza virus

<400> SEQUENCE: 30

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asn Gln Ile
        35                  40                  45

Asn Gly Lys Leu Asn Arg Leu Ile Gly Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asp Lys Leu Phe Glu Arg Thr Lys Lys Gln Leu Arg Glu
        115                 120                 125

Asn Ala Glu Asp Met Gly Asn Gly Cys Phe Lys Ile Tyr His Lys Cys
130                 135                 140

```
Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Ala Leu Leu Gly Phe Ile Met Trp
        195                 200                 205

Ala Cys Gln Lys Gly Asn Ile Arg Cys Asn Ile Cys Ile
        210                 215                 220
```

HIGH TITER RECOMBINANT INFLUENZA VIRUSES WITH ENHANCED REPLICATION IN VERO CELLS

CROSS-REFERENCE TO RELATED APPLICATIONS

This application is a continuation of U.S. patent application Ser. No. 12/912,411, filed Oct. 26, 2010, which claims the benefit of the filing date of U.S. application Ser. No. 61/254,795, filed on Oct. 26, 2009, the disclosure of which is incorporated by reference herein.

STATEMENT OF GOVERNMENT RIGHTS

This invention was made with government support Under AI069274 awarded by the National Institutes of Health. The government has certain rights in the invention.

BACKGROUND

Influenza is a major respiratory disease in some mammals including horses and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. Most commonly, whole virus vaccines are used. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains (Park et al., 2004).

There are three general types of influenza viruses, Type A, Type B and Type C, which are defined by the absence of serological crossreactivity between their internal proteins. Influenza Type A viruses are further classified into subtypes based on antigenic and genetic differences of their glycoproteins, the HA and NA proteins. All the known HA and NA subtypes (H1 to H15 and N1 to N9) have been isolated from aquatic birds, which are though to act as a natural reservoir for influenza. The H1N1 "swine flu" virus has recently been declared to be a pandemic. While this virus may be less virulent than some circulating influenza viruses in certain populations, it is ubiquitous and has become the subject of significant public health efforts. Unfortunately, this virus appears to be less amenable than other viruses to high titer productions which may lead to challenges in vacine manufacture.

SUMMARY OF THE INVENTION

The invention provides isolated recombinant, e.g., reassortant, influenza viruses with selected amino acid residues at specified positions in HA2, NA and/or PB2. In one embodiment, the recombinant reassortant influenza virus has an amino acid residue at position 117 in HA2 (position is based on H1 HA2 numbering; for example, position 117 in H1 HA2 corresponds to position 116 in H3 HA2) that results in enhanced growth in Vero cells relative to a corresponding virus with, for instance, an asparagine at position 117 in HA2, wherein the numbering for HA2 residues is that for H1 HA2. In one embodiment, the recombinant influenza virus has an amino acid residue at position 117 in HA2 that results in fusion of the virus with membranes in endosomes, e.g., late endosomes, at a higher pH relative to a corresponding virus with, for instance, an asparagine at position 117 in HA2, wherein the numbering for HA2 residues is that for H1 HA2. In one embodiment, the invention provides an isolated recombinant reassortant influenza virus having six "internal" gene segments from a vaccine influenza virus, a NA gene segment selected from a first influenza virus isolate, and a HA gene segment selected to encode an aspartic acid or glutamic acid at position 117 in HA2, wherein the numbering for HA2 residues is that for H1 HA2. For example, the NA and HA gene segments may be from a strain for a seasonal flu vaccine or from a pandemic strain, and in one embodiment, the HA2 sequence in the HA gene segment is mutated to encode an aspartic acid or glutamic acid at position 117 in HA2, wherein the numbering for HA2 residues is that for H1 HA2.

As described herein, an influenza virus isolate useful as a vaccine virus (A/Puerto Rico/8/34 (PR8) to carry heterologous gene segments for NA and/or HA was serially passaged in Vero cells to obtain virus with enhanced replication in those cells. In one embodiment, viruses obtained after serial passage which have enhanced replication, have titers that are at least 2, 3, 4 or 5 logs higher than viruses that were not serially passaged. In one embodiment, viruses obtained after serial passage had substitutions in three gene segments, NA, HA and PB2, relative to the parent virus. It was determined that the substitution in HA2 was primarily associated with the enhanced growth phenotype. PR8 virus with HA2 N117D had at least a three log enhancement in titer in Vero cells. The HA2 N117D mutant fused cells at a higher pH than did wild-type HA. Three different recombinant (6:2 mutant reassortant) influenza viruses were prepared that had the same PR8 "internal" genes (i.e., those other than the HA and NA genes), and the NA and HA from a single isolate, and where the residue at position 117 (or position 116 in the H3 reassortant) in HA2 was altered to aspartic acid. All of the 6:2 mutant reassortants showed enhanced growth in Vero cells relative to the corresponding parent 6:2 reassortant. Thus, for vaccine viruses that are to be grown or passaged in cells in culture, e.g., Vero cells, replacement of the residue at position 117 in HA2, wherein the numbering for HA2 residues is that for H1 HA2, e.g., by mutation, or selection of a HA gene segment with a residue that confers enhanced growth of the virus in cultured cells, can result in significantly higher viral titers. Thus, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are rodent or primate, e.g., human, cells. Also provided is a method to identify a HA2 that confers altered growth of a recombinant influenza virus. The method includes introducing one or more substitutions in influenza virus HA2 into a HA gene segment to yield a mutant HA gene segment; and identifying whether the mutant HA gene segment, when present in a replication competent recombinant influenza virus, results in enhanced replication of the recombinant influenza virus in a cell relative to a corresponding replication competent influenza virus without the one or more substitutions in HA2. In one embodiment, at least one substitution is at position 117 in HA2, wherein the numbering for HA2 residues is that for H HA2, e.g., the at least one substitution is to aspartic acid or glutamic acid. In one embodiment, the cells are rodent or primate cells. In one embodiment, the one or more substitutions are to an amino acid residue with an acidic side chain.

In one embodiment, the influenza virus of the invention is a recombinant influenza virus having a mutant HA2 protein with at least one substitution that replaces an amino acid residue with an aliphatic side chain, amide-containing side chain, basic side chain, or sulfur containing side chain with a residue with an aromatic side chain or acidic side chain (a nonconservative substitution), e.g., at position 117 in HA2, wherein the numbering for HA2 residues is that for H1 HA2. In one embodiment, the influenza virus is a recombinant influenza virus having a HA2 protein with a residue with an aromatic side chain or acidic side chain at position 117 in HA2, wherein the numbering for HA2 residues is that for H1 HA2. In one embodiment, the recombinant influenza virus has a mutant HA2 protein with at least one substitution that replaces a neutral or positively charged residue with a polar or negatively charged residue, e.g., at position 117 in HA2, wherein the numbering for HA2 residues is that for H1 HA2. In one embodiment, the influenza virus is a recombinant influenza virus having a HA2 protein with a residue with a polar or negatively charged residue at position 117 in HA2, wherein the numbering for HA2 residues is that for H1 HA2. The presence of the residue with the aromatic side chain or acidic side chain, or the polar or negatively charged residue, at position 117 in HA2 may alter the efficiency or rate of conformational change of HA or pH dependent membrane fusion. In one embodiment, the recombinant reassortant influenza virus comprises a HA gene segment selected to encode an aspartic acid or glutamic acid at position 117 in HA2, wherein recombinant virus has enhanced replication in Vero cells relative to a corresponding virus that does not have aspartic acid or glutamic acid at position 117 in HA2, e.g., where the corresponding virus has an alanine, asparagine, arginine or lysine at position 117 in HA2, wherein the numbering for HA2 residues is that for H1 HA2. In one embodiment, the recombinant virus has a NA gene segment with a tyrosine at position 255, wherein the numbering for NA residues is that for N1.

In one embodiment, the invention provides isolated influenza type A virus with a characteristic residue or substitution at position 117 of HA2, e.g., the residue at position 117 of HA2 is not asparagine, alanine, arginine or lysine, wherein the numbering for HA2 residues is that for H1 HA2. In one embodiment, the isolated influenza type A virus of the invention with a characteristic residue or substitution at position 117 of HA2, has an HA2 amino acid sequence with at least 80%, e.g., 90%, 92%, 95%, 97% or 99%, including any integer between 80 and 99, contiguous amino acid sequence identity to a polypeptide encoded by one of SEQ ID NOs: 16-20 or 22. In one embodiment, the isolated influenza type A virus of the invention with a characteristic residue or substitution at position 117 of HA2, has an HA1 from any one of subtypes 1-15 of HA. In one embodiment, an isolated influenza A virus of the invention has a nonconservative substitution at residue 117 of HA2, e.g., an asparagine to an asparatic acid substitution, wherein the numbering for HA2 residues is that for H1 HA2. In one embodiment, the isolated influenza virus of the invention has an aspartic acid or glutamic acid at position 117 of HA2, wherein the numbering for HA2 residues is that for H1 HA2. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

In one embodiment, a mutation is introduced into a HA gene segment of an influenza virus isolate, e.g., via recombinant DNA techniques including site-specific mutagenesis or replacing a portion of the HA coding sequence that includes residue 117 of HA2 with a portion that includes the characteristic residue(s), wherein the numbering for HA2 residues is that for H1 HA2.

In another embodiment, a HA gene segment with a residue that confers enhanced replication in Vero cells is combined with a compatible NA segment, and internal gene segments of an influenza vaccine virus. In one embodiment, the substitution(s) in the HA2 protein, or the characteristic residue in the HA2 protein, that results in the enhanced replication, is/are at or within about 1 to 10 residues, or any integer in between, for instance, at or within 1 to 5, residues, of residue 117 of the HA2 protein of influenza A virus, wherein the numbering for HA2 residues is that for H1 HA2. In one embodiment, a NA protein has at least one substitution, or has the characteristic residue discussed herein, such as one that results in enhanced replication, at or within about 1 to 10 residues, or any integer in between, e.g., at or within 1 to 5 residues of the codon for residue 255 of the NA protein of influenza A virus, wherein the numbering for NA residues is that for N1.

The invention provides a plurality of influenza virus vectors of the invention, e.g., those useful to prepare reassortant viruses including 6:1:1 reassortants, 6:2 reassortants and 7:1 reassortants. A 6:1:1 reassortant within the scope of the present invention is an influenza virus with 6 internal gene segments from a vaccine virus, a NA gene segment from a different (second) viral isolate, and a HA gene segment with a characteristic residue or substitution at position 117 of HA2 as described herein, where the HA gene segment is from a different viral source than the vaccine virus or the first viral isolate; a 6:2 reassortant within the scope of the present invention is an influenza virus with 6 internal gene segments from a vaccine virus, and a NA gene segment and a HA gene segment from a different (second) viral isolate, where the HA gene segment has the characteristic residue or a substitution at position 117 of HA2 as described herein; and a 7:1 reassortant within the scope of the present invention is an influenza virus with 6 internal gene segments and a NA gene segment from a vaccine virus, and a HA gene segment with a characteristic residue or substitution at position 117 of HA2 as described herein, where the HA gene segment is from a different viral source than the vaccine virus, or an influenza virus with 6 internal gene segments and a HA gene segment with the characteristic residue or substitution at position 117 of HA2 as described herein, and a NA gene segment is from a different viral source than the vaccine virus.

In one embodiment of the invention, the plurality includes vectors for vRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as Vero cells or PER.C6® cells and also optionally embryonated eggs, and/or from a vaccine virus, e.g., one that does not cause significant disease in humans. The DNA for vRNA production of NA may be from any NA, e.g., any of N1-N9, and the DNA for vRNA production of HA may be from any HA, e.g., H1-H16. In one embodiment, the DNAs for vRNA production may be for an influenza B or C virus. For example, the DNAs for vRNA production include influenza B virus PA, PB1, PB2, NP, NS, and M or influenza B virus PA, PB1, PB2, NP, NS, M, and NA, wherein the vRNA for HA has a HA2 with a characteristic amino acid at position 117 in HA2, wherein the numbering for HA2 residues is that for H1 HA2. The DNAs for vRNA production of NA and HA may be from different strains or isolates (6:1:1 reassortants) or from the same strain or isolate (6:2 reassortants), or the NA may be from the same strain or isolate as that for the internal genes (7:1 reassortant), where the HA2 sequence is selected to result in enhanced replication in Vero cells relative to a corresponding virus with, for example, an asparagine at position 117 in HA2, wherein the numbering for HA2 residues is that for H1 HA2. The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Viruses that may provide the internal genes for reassortants within the scope of the invention include viruses that have high titers in Vero cells, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ EID$_{50}$/mL, e.g., at least $10^8$ EID$_{50}$/mL, $10^9$ EID$_{50}$/mL or $10^{10}$ EID$_{50}$/mL; high titers in MDCK cells, e.g., titers of at least about $10^7$ PFU/mL, e.g., at least $10^8$ PFU/mL, or high titers in two of more of those host cells.

In one embodiment, the titers of the reassortant viruses of the invention in cells such as Vero cells may be over 1 log, 2 logs, 3 logs, or greater, than titers of the corresponding virus without that HA2 substitution or that lacks the selected residue at position 117 of HA2, wherein the numbering for HA2 residues is that for H1 HA2.

Other reassortants with internal genes from other PR8 isolates or vaccine viruses may be employed in recombinant reassortant viruses of the invention. In particular, 5:1:2 reassortants having PR8(UW) PB1, PB2, PA, NP, and M ("5") and PR8(Cam) NS ("1"); 6:1:1 reassortants having PR8(UW) NA, PB1, PB2, PA, NP, and M ("6") and PR8 (Cam) NS ("1"); and 7:1 reassortants having PR8(UW) PB1, PB2, PA, NP, M. NA, and NS ("7") may be employed.

In one embodiment, the DNAs for the internal genes for PB1, PB2, PA, NP, M, and NS encode proteins with substantially the same activity as a corresponding polypeptide encoded by one of SEQ ID Nos: 1-6 or 10-15. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:1-6 or 10-15. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:1-6 or 10-15 and, in one embodiment, also encodes a polypeptide having at least 80%, e.g., 90%, 92%, 95%, 97% or 99%, including any integer between 80 and 99, contiguous amino acid sequence identity to a polypeptide encoded by one of SEQ ID NOs: 1-6 or 10-15. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs: 1-6 or 10-15. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:1-6 or 10-15.

The invention thus includes the use of isolated and purified vectors or plasmids, which express or encode influenza virus proteins, or express or encode influenza vRNA, both native and recombinant vRNA. The vectors comprise influenza cDNA, e.g., influenza A (e.g., any influenza A gene including any of the 16 HA or 9 NA subtypes), B or C DNA (see Fields *Virology* (Fields et al. (eds.), Lippincott, Williams and Wickens (2006), which is specifically incorporated by reference herein). Any suitable promoter or transcription termination sequence may be employed to express a protein or peptide. e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, fro instance imay encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, the invention provides a plurality of influenza virus vectors for a reassortant, comprising a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the DNAs for PB1, PB2, PA, NP, NS, and M from one or more influenza vaccine seed viruses, wherein the DNA for NA has sequences for a heterologous NA, and wherein the DNA for HA selected to encode an aspartic acid or glutamic acid at position 117 in HA2, wherein the numbering for HA2 residues is that for H1 HA2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2. In one embodiment, at least one vector comprises sequences corresponding to those encoding PB1, PB2, PA, NP, M, or NS, or a portion thereof, having substantially the same activity as a corresponding polypeptide encoded by one of SEQ ID NOs: 1-6 or 10-15, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs: 1-6 or 10-15. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

In one embodiment, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are rodent or primate cells.

Also provided is a method to identify a HA2 that confers altered growth of a recombinant influenza virus. The method includes introducing one or more substitutions in influenza virus HA2 into a HA gene segment to yield a mutant HA gene segment; and identifying whether the mutant HA gene segment, when present in a replication competent recombinant influenza virus, results in enhanced replication of the recombinant influenza virus in a cell relative to a corresponding replication competent influenza virus without the one or more substitutions in HA2. In one embodiment, at least one substitution is at position 117 in HA2, wherein the numbering for HA2 residues is that for H1 HA2, e.g., at least one substitution is to aspartic acid or glutamic acid. In one embodiment, the cell is a rodent or primate cell. In one embodiment, the one or more substitutions are to an amino acid residue with an acidic side chain.

In one embodiment, the invention provides a method to prepare a recombinant influenza virus with a HA gene segment having a mutant HA2. The method includes altering influenza virus HA nucleic acid at position 117 in HA2 to aspartic acid or glutamic acid; and expressing the altered nucleic acid in a cell having vectors for influenza vRNA production and viral protein production in an amount effective to yield recombinant influenza virus with a HA gene segment having the aspartic acid or glutamic acid at position 117 in HA2, wherein the numbering for HA2 residues is that for H1 HA2. In one embodiment, the cell is a mammalian, e.g., a human cell, or avian cell.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., may be administered separately in conjunction with those anti-virals, for instance, administered before, during and/or after.

The invention also provides a method in which the pH of media in which cells suitable for propagating influenza virus are cultured, is altered during virus propagation to allow for enhanced influenza virus replication in those cells. Thus, for cells with late endosomes having a pH that is higher than that in MDCK cells, altering media pH to maintain a higher pH during virus replication over time, may enhance virus production in the absence of a HA2 protein with a characteristic residue, such as aspartic acid, at position 117, wherein the numbering for HA2 residues is that for H1 HA2.

BRIEF DESCRIPTION OF THE FIGURES

FIGS. 1A-C. Nucleotide sequence for PR8(Cambridge) genes (SEQ ID NOs:10-15).

FIG. 3. Comparison of amino acid sequence differences between PR8 and Vero cell-adapted PR8.

FIG. 5. Growth properties of HA2 N117D virus and wild-type PR8 in MDCK cells.

FIG. 6. Three dimensional structure of HA as a trimer (A), HA as a monomer (B) and HA2 (C).

FIG. 8. Photomicrographs of Vero cells expressing wild-type PR8 HA or HA2 N117D virus at various pH conditions.

FIGS. 9A-B. pH sensitivity of Alexa647 and Oregon Green dyes. A) The fluorescence intensity of Oregon Green dye is sensitive to variations in pH while the fluorescence intensity of Alexa647 does not vary over pH 3 to 7. B) Schematic of assay to detect endosomal pH.

FIGS. 11A-C. HA2 N117D substitution mutants have enhanced infectivity titers in Vero cells. A) Vero cells were infected with A/Kawasaki/173/2001 (H1N1) and A/Kawasaki/173/2001 HA2 N117D and the titers over time determined. B) Vero cells were infected with A/Kawasaki/UTK-4/2009 (H1N1) and A/Kawasaki/UKT-4/2009 HA2 N117D and the titers over time determined. C) Vero cells were infected with A/Yokohama/2017/2003 (H3N2) and A/Yokohama/2017/2003 HA2 N116D and the titers over time determined.

FIGS. 12A-B. A) Alignment of HA2 sequences from A/Aichi/2/68; A/Dk/Sing/97; A/HK/486/97; A/Sw/9/98; and A/HongKong/1073/99 (SEQ ID Nos. 16-20 and 23-27). B) Amino acid sequence of HA sequence from A/California/08/2009 (SEQ ID NO:21). HA2 sequences correspond to residues 336-566 (SEQ ID NO:22.

FIG. 13. HA2 sequences for A/Kawasaki/173/2001, A/Kawasaki/UKT-4/2009, and A/Yokohama/2017/2003 (SEQ ID NOs:28-30). According to the NCBI database, influenza virus HA2 sequences for H1, H2, H3, H5, H7, and H9 HAs were generally conserved at position 116 or 117 (N116 or N117) (more than 99%).

DETAILED DESCRIPTION OF THE INVENTION

Definitions

Figure 2:
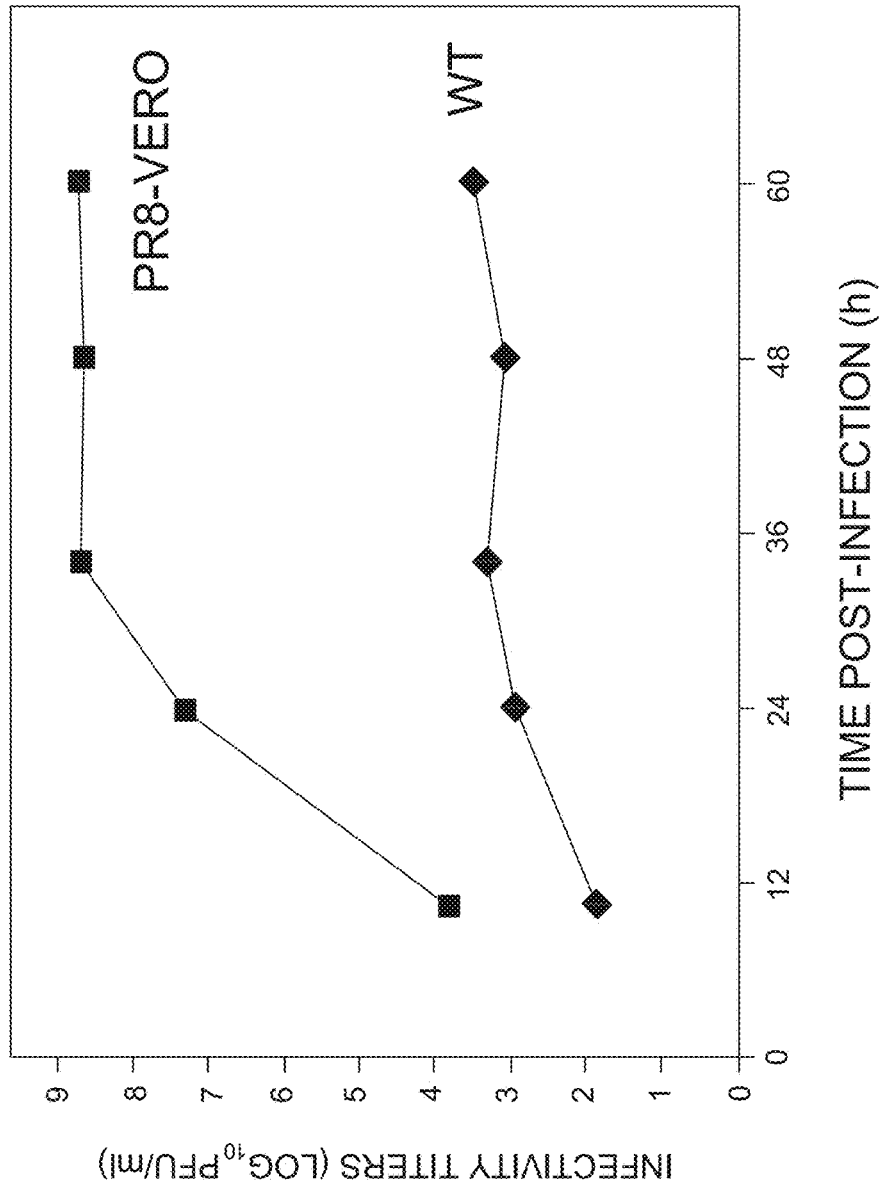
FIG. 2. Growth properties of Vero cell-adapted PR8 virus in Vero cells.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein. "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or gene segment is from an influenza virus source that is different than a majority of the other influenza viral genes or gene segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a gene segment with both NA and NB sequences. Influenza C virus has only seven gene segments.

Cell Lines that can be Used in the Present Invention

Any cell, e.g., any avian or mammalian cell, such as a human, e.g., 293T or PER.C6® cells, or canine, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines.

Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines.

Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantadine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU)/kg, or any range or value therein. The dose of inactivated vaccine may range from about 0.1 to 1000, e.g., 30 to 100 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Heath Service (PHS), which is usually 15 μg, per component for children >3 years of age, and 7.5 μg per component for children <3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

The invention will be described by the following nonlimiting examples.

EXAMPLE 1

Methods
Cells and Viruses
293T human embryonic kidney cells are maintained in Dulbecco's modified Eagle's minimal essential medium (DMEM) with 10% fetal calf serum and antibiotics. Madin-Darby canine kidney (MDCK) cells are grown in MEM with 5% newborn calf serum and antibiotics. African green monkey Vero WCB cells, which had been established after biosafety tests for use in human vaccine production (Sugawara et al., 2002), are maintained in serum-free VP-SFM medium (GIBCO-BRL) with antibiotics. Cells are maintained at 37° C. in 5% $CO_2$. A WHO-recommended vaccine seed virus is NIBRG-14.

Construction of Plasmids and Reverse Genetics
To generate reassortants of influenza A viruses, a plasmid-based reverse genetics (Neumann et al., 1999) is used. The full-length cDNAs were cloned into a plasmid under control of the human polymerase I promoter and the mouse RNA polymerase I terminator (PolI plasmids).

A previously produced series of PolI constructs, derived from A/WSN/33 (H5N1; WSN) or PR8 strains is used, for reverse genetics (Horimoto et al., 2006; Neumann et al., 1999). The World Health Organization (WHO) recommends A/Puerto Rico/8/34 (H1N1; PR8) as a donor virus, because of its safety in humans (Wood & Robertson, 2004; Webby & Webster, 2003).

Plasmids expressing WSN or PR8 NP, PA, PB1, or PB2 under control of the chicken β-actin promoter are used for all reverse genetics experiments (Horimoto et al., 2006; Neumann et al., 1999). Briefly, PolI plasmids and protein expression plasmids are mixed with a transfection reagent, Trans-IT 293T (Panvera), incubated at room temperature for 15 minutes, and then added to 293T cells. Transfected cells are incubated in Opti-MEM I (GIBCO-BRL) for 48 hours. For reverse genetics in Vero WCB cells, an electroporator (Amaxa) is used to transfect the plasmid mixtures according to the manufacturer's instructions. Sixteen hours after transfection, freshly prepared Vero WCB cells were added onto the transfected cells and TPCK-trypsin (1 μg/mL) is added to the culture 6 hours later. Transfected cells are incubated in serum-free VP-SFM for a total of 4 days. Supernatants containing infectious viruses are harvested, and may be biologically cloned by limiting dilution.

A recombinant virus having the HA and NA genes from A/Hong Kong/213/2003 (H5N1) and the remainder of the type A influenza virus genes from PR8(UW) was prepared. The titer of the recombinant virus was $10^{10.67}$ $EID_{50}$/mL, and the HA titer was 1:1600

TABLE 1

| Virus possessing PR8 genes together with the following HA and NA genes | HA titer (HAU/mL) in each dilition | | | | | | |
|---|---|---|---|---|---|---|---|
| | 10-2 | 10-3 | 10-4 | 10-5 | 10-6 | 10-7 | 10-8 |
| WSN-HA NA | 160 | 40 | 40 | 320 | 40 | 640 | <1 |
| HK-HAavir NA | 400 | 800 | 400 | 400 | 400 | 800 | <1 |

The sequences of PR8 (UW) genes are as follows:

PA (SEQ ID NO: 1)
AGCGAAAGCA GGTACTGATC CAAAATGGAA GATTTTGTGC

GACAATGCTT CAATCCGATG ATTGTCGAGC TTGCGGAAAA

AACAATGAAA GAGTATGGGG AGGACCTGAA AATCGAAACA

AACAAATTTG CAGCAATATG CACTCACTTG GAAGTATGCT

TCATGTATTC AGATTTTCAC TTCATCAATG AGCAAGGCGA

GTCAATAATC GTAGAACTTG GTGATCCAAA TGCACTTTTG

AAGCACAGAT TTGAAATAAT CGAGGGAAGA GATCGCACAA

TGGCCTGGAC AGTAGTAAAC AGTATTTGCA ACACTACAGG

GGCTGAGAAA CCAAAGTTTC TACCAGATTT GTATGATTAC

AAGGAGAATA GATTCATCGA AATTGGAGTA ACAAGGAGAG

AAGTTCACAT ATACTATCTG GAAAAGGCCA ATAAAATTAA

ATCTGAGAAA ACACACATCC ACATTTTCTC GTTCACTGGG

GAAGAAATGG CCACAAAGGC AGACTACACT CTCGATGAAG

AAAGCAGGGC TAGGATCAAA ACCAGACTAT TCACCATAAG

ACAAGAAATG GCCAGCAGAG GCCTCTGGGA TTCCTTTCGT

CAGTCCGAGA GAGGAGAAGA GACAATTGAA GAAAGGTTTG

AAATCACAGG AACAATGCGC AAGCTTGCCG ACCAAAGTCT

CCCGCCGAAC TTCTCCAGCC TTGAAAATTT TAGAGCCTAT

GTGGATGGAT TCGAACCGAA CGGCTACATT GAGGGCAAGC

TGTCTCAAAT GTCCAAAGAA GTAAATGCTA GAATTGAACC

TTTTTTGAAA ACAACACCAC GACCACTTAG ACTTCCGAAT

GGGCCTCCCT GTTCTCAGCG GTCCAAATTC CTGCTGATGG

ATGCCTTAAA ATTAAGCATT GAGGACCCAA GTCATGAAGG

AGAGGGAATA CCGCTATATG ATGCAATCAA ATGCATGAGA
ACATTCTTTG GATGGAAGGA ACCCAATGTT GTTAAACCAC
ACGAAAAGGG AATAAATCCA AATTATCTTC TGTCATGGAA
GCAAGTACTG GCAGAACTGC AGGACATTGA GAATGAGGAG
AAAATTCCAA AGACTAAAAA TATGAAGAAA ACAAGTCAGC
TAAAGTGGGC ACTTGGTGAG AACATGGCAC AGAAAAGGT
AGACTTTGAC GACTGTAAAG ATGTAGGTGA TTTGAAGCAA
TATGATAGTG ATGAACCAGA ATTGAGGTCG CTTGCAAGTT
GGATTCAGAA TGAGTTTAAC AAGGCATGCG AACTGACAGA
TTCAAGCTGG ATAGAGCTCG ATGAGATTGG AGAAGATGTG
GCTCCAATTG AACACATTGC AAGCATGAGA AGGAATTATT
TCACATCAGA GGTGTCTCAC TGCAGAGCCA CAGAATACAT
AATGAAGGGA GTGTACATCA ATACTGCCTT GCTTAATGCA
TCTTGTGCAG CAATGGATGA TTTCCAATTA ATTCCAATGA
TAAGCAAGTG TAGAACTAAG GAGGGAAGGC GAAAGACCAA
CTTGTATGGT TTCATCATAA AAGGAAGATC CCACTTAAGG
AATGACACCG ACGTGGTAAA CTTTGTGAGC ATGGAGTTTT
CTCTCACTGA CCCAAGACTT GAACCACATA AATGGGAGAA
GTACTGTGTT CTTGAGATAG GAGATATGCT TATAAGAAGT
GCCATAGGCC AGGTTTCAAG GCCCATGTTC TTGTATGTGA
GAACAAATGG AACCTCAAAA ATTAAAATGA ATGGGGAAT
GGAGATGAGG CGTTGCCTCC TCCAGTCACT TCAACAAATT
GAGAGTATGA TTGAAGCTGA GTCCTCTGTC AAAGAGAAAG
ACATGACCAA AGAGTTCTTT GAGAACAAAT CAGAAACATG
GCCCATTGGA GAGTCCCCCA AAGGAGTGGA GGAAAGTTCC
ATTGGGAAGG TCTGCAGGAC TTTATTAGCA AAGTCGGTAT
TCAACAGCTT GTATGCATCT CCACAACTAG AAGGATTTTC
AGCTGAATCA AGAAAACTGC TTCTTATCGT TCAGGCTCTT
AGGGACAACC TGGAACCTGG GACCTTTGAT CTTGGGGGGC
TATATGAAGC AATTGAGGAG TGCCTGATTA ATGATCCCTG
GGTTTTGCTT AATGCTTCTT GGTTCAACTC CTTCCTTACA
CATGCATTGA GTTAGTTGTG GCAGTGCTAC TATTTGCTAT
CCATACTGTC CAAAAAAGTA CCTTGTTTCT ACT
PB1
(SEQ ID NO: 2)
AGCGAAAGCA GGCAAACCAT TTGAATGGAT GTCAATCCGA
CCTTACTTTT CTTAAAAGTG CCAGCACAAA ATGCTATAAG
CACAACTTTC CCTTATACTG GAGACCCTCC TTACAGCCAT
GGGACAGGAA CAGGATACAC CATGGATACT GTCAACAGGA
CACATCAGTA CTCAGAAAAG GGAAGATGGA CAACAAACAC
CGAAACTGGA GCACCGCAAC TCAACCCGAT TGATGGGCCA
CTGCCAGAAG ACAATGAACC AAGTGGTTAT GCCCAAACAG

ATTGTGTATT GGAGGCGATG GCTTTCCTTG AGGAATCCCA
TCCTGGTATT TTTGAAAACT CGTGTATTGA AACGATGGAG
GTTGTTCAGC AAACACGAGT AGACAAGCTG ACACAAGGCC
GACAGACCTA TGACTGGACT CTAAATAGAA CCAACCTGC
TGCAACAGCA TTGGCCAACA CAATAGAAGT GTTCAGATCA
AATGGCCTCA CGGCCAATGA GTCTGGAAGG CTCATAGACT
TCCTTAAGGA TGTAATGGAG TCAATGAACA AGAAGAAAT
GGGGATCACA ACTCATTTTC AGAGAAAGAG ACGGGTGAGA
GACAATATGA CTAAGAAAAT GATAACACAG AGAACAATGG
GTAAAAAGAA GCAGAGATTG AACAAAAGGA GTTATCTAAT
TAGAGCATTG ACCCTGAACA CAATGACCAA AGATGCTGAG
AGAGGGAAGC TAAAACGGAG AGCAATTGCA ACCCCAGGGA
TGCAAATAAG GGGGTTTGTA TACTTTGTTG AGACACTGGC
AAGGAGTATA TGTGAGAAAC TTGAACAATC AGGGTTGCCA
GTTGGAGGCA ATGAGAAGAA AGCAAAGTTG GCAAATGTTG
TAAGGAAGAT GATGACCAAT TCTCAGGACA CCGAACTTTC
TTTCACCATC ACTGGAGATA ACACCAAATG AACGAAAAT
CAGAATCCTC GGATGTTTTT GGCCATGATC ACATATATGA
CCAGAAATCA GCCCGAATGG TTCAGAAATG TTCTAAGTAT
TGCTCCAATA ATGTTCTCAA ACAAAATGGC GAGACTGGGA
AAAGGGTATA TGTTTGAGAG CAAGAGTATG AAACTTAGAA
CTCAAATACC TGCAGAAATG CTAGCAAGCA TCGATTTGAA
ATATTTCAAT GATTCAACAA GAAAGAAGAT TGAAAAATC
CGACCGCTCT TAATAGAGGG GACTGCATCA TTGAGCCCTG
GAATGATGAT GGGCATGTTC AATATGTTAA GCACTGTATT
AGGCGTCTCC ATCCTGAATC TTGGACAAAA GAGATACACC
AAGACTACTT ACTGGTGGGA TGGTCTTCAA TCCTCTGACG
ATTTTGCTCT GATTGTGAAT GCACCCAATC ATGAAGGGAT
TCAAGCCGGA GTCGACAGGT TTTATCGAAC CTGTAAGCTA
CTTGGAATCA ATATGAGCAA GAAAAAGTCT TACATAAACA
GAACAGGTAC ATTTGAATTC ACAAGTTTTT TCTATCGTTA
TGGGTTTGTT GCCAATTTCA GCATGGAGCT TCCCAGTTTT
GGGGTGTCTG GGATCAACGA GTCAGCGGAC ATGAGTATTG
GAGTTACTGT CATCAAAAAC AATATGATAA ACAATGATCT
TGGTCCAGCA ACAGCTCAAA TGGCCCTTCA GTTGTTCATC
AAAGATTACA GGTACACGTA CCGATGCCAT ATAGGTGACA
CACAAATACA AACCCGAAGA TCATTTGAAA TAAAGAAACT
GTGGGAGCAA ACCCGTTCCA AAGCTGGACT GCTGGTCTCC
GACGGAGGCC CAAATTTATA CAACATTAGA AATCTCCACA
TTCCTGAAGT CTGCCTAAAA TGGGAATTGA TGGATGAGGA

```
TTACCAGGGG CGTTTATGCA ACCCACTGAA CCCATTTGTC
AGCCATAAAG AAATTGAATC AATGAACAAT GCAGTGATGA
TGCCAGCACA TGGTCCAGCC AAAAACATGG AGTATGATGC
TGTTGCAACA ACACACTCCT GGATCCCCAA AAGAAATCGA
TCCATCTTGA ATACAAGTCA AGAGGAGTA CTTGAGGATG
AACAAATGTA CCAAAGGTGC TGCAATTTAT TTGAAAAATT
CTTCCCCAGC AGTTCATACA GAAGACCAGT CGGGATATCC
AGTATGGTGG AGGCTATGGT TTCCAGAGCC CGAATTGATG
CACGGATTGA TTTCGAATCT GGAAGGATAA AGAAAGAAGA
GTTCACTGAG ATCATGAAGA TCTGTTCCAC CATTGAAGAG
CTCAGACGGC AAAAATAGTG AATTTAGCTT GTCCTTCATG
AAAAAATGCC TTGTTTCTAC T
```

PB2
(SEQ ID NO: 3)
```
AGCGAAAGCA GGTCAATTAT ATTCAATATG GAAAGAATAA
AAGAACTACG AAATCTAATG TCGCAGTCTC GCACCCGCGA
GATACTCACA AAAACCACCG TGGACCATAT GGCCATAATC
AAGAAGTACA CATCAGGAAG ACAGGAGAAG AACCCAGCAC
TTAGGATGAA ATGGATGATG GCAATGAAAT ATCCAATTAC
AGCAGACAAG AGGATAACGG AAATGATTCC TGAGAGAAAT
GAGCAAGGAC AAACTTTATG GAGTAAAATG AATGATGCCG
GATCAGACCA GTGATGGTA TCACCTCTGG CTGTGACATG
GTGGAATAGG AATGGACCAA TAACAAATAC AGTTCATTAT
CCAAAAATCT ACAAAACTTA TTTTGAAAGA GTCGAAAGGC
TAAAGCATGG AACCTTTGGC CCTGTCCATT TTAGAAACCA
AGTCAAAATA CGTCGGAGAG TTGACATAAA TCCTGGTCAT
GCAGATCTCA GTGCCAAGGA GGCACAGGAT GTAATCATGG
AAGTTGTTTT CCCTAACGAA GTGGGAGCCA GGATACTAAC
ATCGGAATCG CAACTAACGA TAACCAAAGA GAAGAAAGAA
GAACTCCAGG ATTGCAAAAT TTCTCCTTTG ATGGTTGCAT
ACATGTTGGA GAGAGAACTG GTCCGCAAAA CGAGATTCCT
CCCAGTGGCT GGTGGAACAA GCAGTGTGTA CATTGAAGTG
TTGCATTTGA CTCAAGGAAC ATGCTGGGAA CAGATGTATA
CTCCAGGAGG GGAAGTGAGG AATGATGATG TTGATCAAAG
CTTGATTATT GCTGCTAGGA ACATAGTGAG AAGAGCTGCA
GTATCAGCAG ATCCACTAGC ATCTTTATTG GAGATGTGCC
ACAGCACACA GATTGGTGGA ATTAGGATGG TAGACATCCT
TAGGCAGAAC CCAACAGAAG AGCAAGCCGT GGATATATGC
AAGGCTGCAA TGGGACTGAG AATTAGCTCA TCCTTCAGTT
TTGGTGGATT CACATTTAAG AGAACAAGCG GATCATCAGT
CAAGAGAGAG GAAGAGGTGC TTACGGGCAA TCTTCAAACA
TTGAAGATAA GAGTGCATGA GGGATATGAA GAGTTCACAA
```
```
TGGTTGGGAG AAGAGCAACA GCCATACTCA GAAAAGCAAC
CAGGAGATTG ATTCAGCTGA TAGTGAGTGG GAGAGACGAA
CAGTCGATTG CCGAAGCAAT AATTGTGGCC ATGGTATTTT
CACAAGAGGA TTGTATGATA AAAGCAGTCA GAGGTGATCT
GAATTTCGTC AATAGGGCGA ATCAACGATT GAATCCTATG
CATCAACTTT TAAGCATTT TCAGAAGGAT GCGAAAGTGC
TTTTTCAAAA TTGGGGAGTT GAACCTATCG ACAATGTGAT
GGGAATGATT GGGATATTGC CCGACATGAC TCCAAGCATC
GAGATGTCAA TGAGAGGAGT GAGAATCAGC AAAATGGGTG
TAGATGAGTA CTCCAGCACG GAGAGGGTAG TGGTGAGCAT
TGACCGTTTT TTGAGAATCC GGGACCAACG AGGAAATGTA
CTACTGTCTC CCGAGGAGGT CAGTGAAACA CAGGGAACAG
AGAAACTGAC AATAACTTAC TCATCGTCAA TGATGTGGGA
GATTAATGGT CCTGAATCAG TGTTGGTCAA TACCTATCAA
TGGATCATCA GAAACTGGGA AACTGTTAAA ATTCAGTGGT
CCCAGAACCC TACAATGCTA TACAATAAAA TGGAATTTGA
ACCATTTCAG TCTTTAGTAC CTAAGGCCAT TAGAGGCCAA
TACAGTGGGT TTGTAAGAAC TCTGTTCCAA CAAATGAGGG
ATGTGCTTGG GACATTTGAT ACCGCACAGA TAATAAAACT
TCTTCCCTTC GCAGCCGCTC ACCAAAGCA AAGTAGAATG
CAGTTCTCCT CATTTACTGT GAATGTGAGG GGATCAGGAA
TGAGAATACT TGTAAGGGGC AATTCTCCTG TATTCAACTA
TAACAAGGCC ACGAAGAGAC TCACAGTTCT CGGAAAGGAT
GCTGGCACTT TAACTGAAGA CCCAGATGAA GGCACAGCTG
GAGTGGAGTC CGCTGTTCTG AGGGGATTCC TCATTCTGGG
CAAAGAAGAC AAGAGATATG GCCAGCACT AAGCATCAAT
GAACTGAGCA ACCTTGCGAA AGGAGAGAAG GCTAATGTGC
TAATTGGGCA AGGAGACGTG GTGTTGGTAA TGAAACGGAA
ACGGGACTCT AGCATACTTA CTGACAGCCA GACAGCGACC
AAAAGAATTC GGATGGCCAT CAATTAGTGT CGAATAGTTT
AAAAACGACC TTGTTTCTAC T
```
NP
(SEQ ID NO: 4)
```
AGCAAAAGCA GGGTAGATAA TCACTCACTG AGTGACATCA
AAATCATGGC GTCTCAAGGC ACCAAACGAT CTTACGAACA
GATGGAGACT GATGGAGAAC GCCAGAATGC CACTGAAATC
AGAGCATCCG TCGGAAAAAT GATTGGTGGA ATTGGACGAT
TCTACATCCA AATGTGCACC GAACTCAAAC TCAGTGATTA
TGAGGGACGG TTGATCCAAA ACAGCTTAAC AATAGAGAGA
ATGGTGCTCT CTGCTTTTGA CGAAGGAGA AATAAATACC
TTGAAGAACA TCCCAGTGCG GGAAAGATC CTAAGAAAAC
```

-continued

TGGAGGACCT ATATACAGGA GAGTAAACGG AAAGTGGATG

AGAGAACTCA TCCTTTATGA CAAAGAAGAA ATAAGGCGAA

TCTGGCGCCA AGCTAATAAT GGTGACGATG CAACGGCTGG

TCTGACTCAC ATGATGATCT GGCATTCCAA TTTGAATGAT

GCAACTTATC AGAGGACAAG AGCTCTTGTT CGCACCGGAA

TGGATCCCAG GATGTGCTCT CTGATGCAAG GTTCAACTCT

CCCTAGGAGG TCTGGAGCCG CAGGTGCTGC AGTCAAAGGA

GTTGGAACAA TGGTGATGGA ATTGGTCAGA ATGATCAAAC

GTGGGATCAA TGATCGGAAC TTCTGGAGGG GTGAGAATGG

ACGAAAAACA AGAATTGCTT ATGAAAGAAT GTGCAACATT

CTCAAAGGGA AATTTCAAAC TGCTGCACAA AAAGCAATGA

TGGATCAAGT GAGAGAGAGC CGGAACCCAG GGAATGCTGA

GTTCGAAGAT CTCACTTTTC TAGCACGGTC TGCACTCATA

TTGAGAGGGT CGGTTGCTCA CAAGTCCTGC CTGCCTGCCT

GTGTGTATGG ACCTGCCGTA GCCAGTGGGT ACGACTTTGA

AAGGGAGGGA TACTCTCTAG TCGGAATAGA CCCTTTCAGA

CTGCTTCAAA CAGCCAAGT GTACAGCCTA ATCAGACCAA

ATGAGAATCC AGCACACAAG AGTCAACTGG TGTGGATGGC

ATGCCATTCT GCCGCATTTG AAGATCTAAG AGTATTAAGC

TTCATCAAAG GGACGAAGGT GCTCCCAAGA GGGAAGCTTT

CCACTAGAGG AGTTCAAATT GCTTCCAATG AAAATATGGA

GACTATGGAA TCAAGTACAC TTGAACTGAG AAGCAGGTAC

TGGGCCATAA GGACCAGAAG TGGAGGAAAC ACCAATCAAC

AGAGGGCATC TGCGGGCCAA ATCAGCATAC AACCTACGTT

CTCAGTACAG AGAAATCTCC CTTTTGACAG AACAACCATT

ATGGCAGCAT TCAATGGGAA TACAGAGGGG AGAACATCTG

ACATGAGGAC CGAAATCATA AGGATGATGG AAAGTGCAAG

ACCAGAAGAT GTGTCTTTCC AGGGGCGGGG AGTCTTCGAG

CTCTCGGACG AAAAGGCAGC GAGCCCGATC GTGCCTTCCT

TTGACATGAG TAATGAAGGA TCTTATTTCT TCGGAGACAA

TGCAGAGGAG TACGACAATT AAAGAAAAAT ACCCTTGTTT

CTACT

M                                               (SEQ ID NO: 5)

AGCAAAAGCA GGTAGATATT GAAAGATGAG TCTTCTAACC

GAGGTCGAAA CGTACGTACT CTCTATCATC CCGTCAGGCC

CCCTCAAAGC CGAGATCGCA CAGAGACTTG AAGATGTCTT

TGCAGGGAAG AACACCGATC TTGAGGTTCT CATGGAATGG

CTAAAGACAA GACCAATCCT GTCACCTCTG ACTAAGGGGA

TTTTAGGATT TGTGTTCACG CTCACCGTGC CCAGTGAGCG

AGGACTGCAG CGTAGACGCT TTGTCCAAAA TGCCCTTAAT

GGGAACGGGG ATCCAAATAA CATGGACAAA GCAGTTAAAC

-continued

TGTATAGGAA GCTCAAGAGG GAGATAACAT TCCATGGGGC

CAAAGAAATC TCACTCAGTT ATTCTGCTGG TGCACTTGCC

AGTTGTATGG GCCTCATATA CAACAGGATG GGGGCTGTGA

CCACTGAAGT GGCATTTGGC CTGGTATGTG CAACCTGTGA

ACAGATTGCT GACTCCCAGC ATCGGTCTCA TAGGCAAATG

GTGACAACAA CCAATCCACT AATCAGACAT GAGAACAGAA

TGGTTTTAGC CAGCACTACA GCTAAGGCTA TGGAGCAAAT

GGCTGGATCG AGTGAGCAAG CAGCAGAGGC ATGGAGGTT

GCTAGTCAGG CTAGACAAAT GGTGCAAGCG ATGAGAACCA

TTGGGACTCA TCCTAGCTCC AGTGCTGGTC TGAAAAATGA

TCTTCTTGAA AATTTGCAGG CCTATCAGAA ACGAATGGGG

GTGCAGATGC AACGGTTCAA GTGATCCTCT CACTATTGCC

GCAAATATCA TTGGGATCTT GCACTTGACA TTGTGGATTC

TTGATCGTCT TTTTTTCAAA TGCATTTACC GTCGCTTTAA

ATACGGACTG AAAGGAGGGC CTTCTACGGA AGGAGTGCCA

AAGTCTATGA GGGAAGAATA TCGAAAGGAA CAGCAGAGTG

CTGTGGATGC TGACGATGGT CATTTTGTCA GCATAGAGCT

GGAGTAAAAA ACTACCTTGT TTCTACT

NS                                              (SEQ ID NO: 6)

AGCAAAAGCA GGGTGACAAA AACATAATGG ATCCAAACAC

TGTGTCAAGC TTTCAGGTAG ATTGCTTTCT TTGGCATGTC

CGCAAACGAG TTGCAGACCA AGAACTAGGC GATGCCCCAT

TCCTTGATCG GCTTCGCCGA GATCAGAAAT CCCTAAGAGG

AAGGGGCAGT ACTCTCGGTC TGGACATCAA GACAGCCACA

CGTGCTGGAA AGCAGATAGT GGAGCGGATT CTGAAAGAAG

AATCCGATGA GGCACTTAAA ATGACCATGG CCTCTGTACC

TGCGTCGCGT TACCTAACTG ACATGACTCT TGAGGAAATG

TCAAGGGACT GGTCCATGCT CATACCCAAG CAGAAAGTGG

CAGGCCCTCT TTGTATCAGA ATGGACCAGG CGATCATGGA

TAAGAACATC ATACTGAAAG CGAACTTCAG TGTGATTTTT

GACCGGCTGG AGACTCTAAT ATTGCTAAGG GCTTTCACCG

AAGAGGGAGC AATTGTTGGC GAAATTTCAC CATTGCCTTC

TCTTCCAGGA CATACTGCTG AGGATGTCAA AAATGCAGTT

GGAGTCCTCA TCGGAGGACT TGAATGGAAT GATAACACAG

TTCGAGTCTC TGAAACTCTA CAGAGATTCG CTTGGAGAAG

CAGTAATGAG AATGGGAGAC CTCCACTCAC TCCAAAACAG

AAACGAGAAA TGGCGGGAAC AATTAGGTCA GAAGTTTGAA

GAAATAAGAT GGTTGATTGA AGAAGTGAGA CACAAACTGA

AGATAACAGA GAATAGTTTT GAGCAAATAA CATTTATGCA

AGCCTTACAT CTATTGCTTG AAGTGGAGCA AGAGATAAGA

-continued

```
ACTTTCTCGT TTCAGCTTAT TTAGTACTAA AAAACACCCT

TGTTTCTACT
```

HA (SEQ ID NO: 7)
```
AGCAAAAGCAGGGGAAAATAAAAACAACCAAAATGAAGGCAAACCTACTG

GTCCTGTTATGTGCACTTGCAGCTGCAGATGCAGACACAATATGTATAGG

CTACCATGCGAACAATTCAACCGACACTGTTGACACAGTACTCGAGAAGA

ATGTGACAGTGACACACTCTGTTAACCTGCTCGAAGACAGCCACAACGGA

AAACTATGTAGATTAAAAGGAATAGCCCCACTACAATTGGGGAAATGTAA

CATCGCCGGATGGCTCTTGGGAAACCCAGAATGCGACCCACTGCTTCCAG

TGAGATCATGGTCCTACATTGTAGAAACACCCAAACTCTGAGAATGGAATA

TGTTATCCAGGAGATTTCATCGACTATGAGGAGCTGAGGGAGCAATTGAG

CTCAGTGTCATCATTCGAAAGATTCGAAATATTTCCCAAAGAAAGCTCAT

GGCCCAACCACAACACAAACGGAGTAACGGCAGCATGCTCCCATGAGGGG

AAAAGCAGTTTTTACAGAAATTTGCTATGGCTGACGGAGAAGGAGGGCTC

ATACCCAAAGCTGAAAAATTCTTATGTGAACAAAAAAGGGAAAGAAGTCC

TTGTACTGTGGGGTATTCATCACCCGCCTAACAGTAAGGAACAACAGAAT

CTCTATCAGAATGAAAATGCTTATGTCTCTGTAGTGACTTCAAATTATAA

CAGGAGATTTACCCCGGAAATAGCAGAAAGACCCAAAGTAAGAGATCAAG

CTGGGAGGATGAACTATTACTGGACCTTGCTAAAACCCGGAGACACAATA

ATATTTGAGGCAAATGGAAATCTAATAGCACCAATGTATGCTTTCGCACT

GAGTAGAGGCTTTGGGTCCGGCATCATCACCTCAAACGCATCAATGCATG

AGTGTAACACGAAGTGTCAAACACCCCTGGGAGCTATAAACAGCAGTCTC

CCTTACCAGAATATACACCCAGTCACAATAGGAGAGTGCCCAAAATACGT

CAGGAGTGCCAAATTGAGGATGGTTACAGGACTAAGGAACATTCCGTCCA

TTCAATCCAGAGGTCTATTTGGAGCCATTGCCGGTTTTATTGAAGGGGGA

TGGACTGGAATGATAGATGGATGGTATGGTTATCATCATCAGAATGAACA

GGGATCAGGCTATGCAGCGGATCAAAAAAGCACACAAAATGCCATTAACG

GGATTACAAACAAGGTGAACACTGTTATCGAGAAAATGAACATTCAATTC

ACAGCTGTGGGTAAAGAATTCAACAAATTAGAAAAAAGGATGGAAAATTT

AAATAAAAAAGTTGATGATGGATTTCTGGACATTTGGACATATAATGCAG

AATTGTTAGTTCTACTGGAAAATGAAAGGACTCTGGATTTCCATGACTCA

AATGTGAAGAATCTGTATGAGAAAGTAAAAAGCCAATTAAAGAATAATGC

CAAAGAAATCGGAAATGGATGTTTTGAGTTCTACCACAAGTGTGACAATG

AATGCATGGAAAGTGTAAGAAATGGGACTTATGATTATCCCAAATATTCA

GAAGAGTCAAAGTTGAACAGGGAAAAGGTAGATGGAGTGAAATTGGAATC

AATGGGGATCTATCAGATTCTGGCGATCTACTCAACTGTCGCCAGTTCAC

TGGTGCTTTTGGTCTCCCTGGGGGCAATCAGTTTCTGGATGTGTTCTAAT

GGATCTTTGCAGTGCAGAATATGCATCTGAGATTAGAATTTCAGAGATAT

GAGGAAAAACACCCTTGTTTCTACT
```

NA (SEQ ID NO: 8)
```
AGCAAAAGCAGGGGTTTAAAATGAATCCAAATCAGAAAATAATAACCATT

GGATCAATCTGTCTGGTAGTCGGACTAATTAGCCTAATATTGCAAATAGG

GAATATAATCTCAATATGGATTAGCCATTCAATTCAAACTGGAAGTCAAA

ACCATACTGGAATATGCAACCAAAACATCATTACCTATAAAAATAGCACC

TGGGTAAAGGACACAACTTCAGTGATATTAACCGGCAATTCATCTCTTTG

TCCCATCCGTGGGTGGCTATATACAGCAAAGACAATAGCATAAGAATTG

GTTCCAAAGGAGACGTTTTTGTCATAAGAGAGCCCTTTATTTCATGTTCT

CACTTGGAATGCAGGACCTTTTTTCTGACCCAAGGTGCCTTACTGAATGA

CAAGCATTCAAGTGGGACTGTTAAGGACAGAAGCCCTTATAGGGCCTTAA

TGAGCTGCCCTGTCGGTGAAGCTCCGTCCCCGTACAATTCAAGATTTGAA

TCGGTTGCTTGGTCAGCAAGTGCATGTCATGATGGCATGGGCTGGCTAAC

AATCGGAATTTCAGGTCCAGATAATGGAGCAGTGGCTGTATTAAAATACA

ACGGCATAATAACTGAAACCATAAAAAGTTGGAGGAAGAAAATATTGAGG

ACACAAGAGTCTGAATGTGCCTGTGTAAATGGTTCATGTTTTACTATAAT

GACTGATGGCCCGAGTGATGGGCTGGCCTCGTACAAAATTTTCAAGATCG

AAAAGGGGAAGGTTACTAAATCAATAGAGTTGAATGCACCTAATTCTCAC

TATGAGGAATGTTCCTGTTACCCTGATACCGGCAAAGTGATGTGTGTGTG

CAGAGACAATTGGCATGGTTCGAACCGGCCATGGGTGTCTTTCGATCAAA

ACCTGGATTATCAAATAGGATACATCTGCAGTGGGGTTTTCGGTGACAAC

CCGCGTCCCGAAGATGGAACAGGCAGCTGTGGTCCAGTGTATGTTGATGG

AGCAAACGGAGTAAAGGGATTTTCATATAGGTATGGTAATGGTGTTTGGA

TAGGAAGGACCAAAAGTCACAGTTCCAGACATGGGTTTGAGATGATTTGG

GATCCTAATGGATGGACAGAGACTGATAGTAAGTTCTCTGTGAGGCAAGA

TGTTGTGGCAATGACTGATTGGTCAGGGTATAGCGGAAGTTTCGTTCAAC

ATCCTGAGCTGACAGGGCTAGACTGTATGAGGCCGTGCTTCTGGGTTGAA

TTAATCAGGGGACGACCTAAAGAAAAAACAATCTGGACTAGTGCGAGCAG

CATTTCTTTTTGTGGCGTGAATAGTGATACTGTAGATTGGTCTTGGCCAG

ACGGTGCTGAGTTGCCATTCAGCATTGACAAGTAGTCTGTTCAAAAAACT

CCTTGTTTCTACT
```

High-titer A/PR/8/34 (H1N1, PR8(UW)) virus grows 10 times better than other A/PR/8/34 PR8 strains in eggs ($10^{10}$ $EID_{50}$/mL; HA titer:1:8,000). Thus, replacement of the HA and NA genes of PR8(UW) with those of a currently circulating strain of influenza virus results in a vaccine strain that can be safely produced, and validates the use of PR8 (UW) as a master vaccine strain.

Genes that contribute to different growth properties between PR8(UW) and PR8 (Cambridge), which provides the non-HA and -NA genes of the NIBRG-14 vaccine strain (Figures IA-C), were determined. Higher titers in eggs were obtained when the majority of internal genes were from PR8(UW). Highest titers were with the M gene segment of PR8(UW) and the NS gene of PR8 (Cambridge). The NS gene in PR8(UW) has a K (lysine) at residue 55 while the NS gene in PR8(Cam) has a E (glutamic acid). The polymerase subunit (PA, PB1, and PB2) and NP genes of PR8(UW) enhanced the growth of an H5N1 vaccine seed virus in chicken embryonated eggs, and the NS gene of PR8(Cambridge) enhanced the growth of an H5N1 vaccine seed virus in chicken embryonated eggs. A tyrosine (Y) at position 360 in PB2 of PR8(UW) likely contributes to the high growth rate of that virus in MDCK cells.

EXAMPLE 2

To establish robust systems for influenza vaccine production, egg-free, cell culture-based systems are needed. Vero cells are approved for human use and so are candidate hosts for influenza virus vaccine production. To elucidate the molecular basis for efficient growth of influenza vaccine seed virus in Vero cells, A/Puerto Rico/8/34 (PR8) virus was passaged through Vero cells 12 times and the infectivity titer of the resulting virus was determined. Vero cell-adapted PR8 had over a 4 log increase in infectivity titers relative to non Vero cell-adapted PR8 (FIG. 2).

Figure 4:
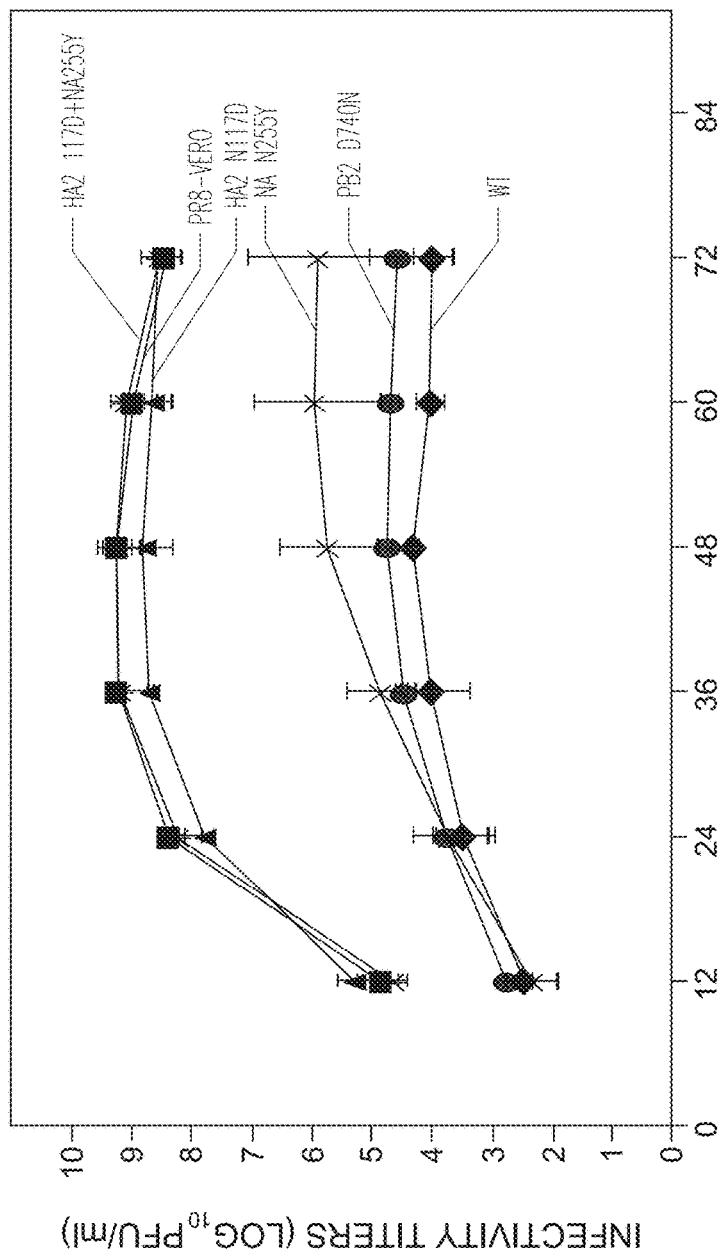
FIG. 4. Growth properties of Vero cell-adapted PR8, non Vero cell-adapted "wild-type" PR8, and recombinant viruses with one or two substitutions relative to wild-type virus in Vero cells.

To determine the molecular basis for that growth difference, the genomes of both isolates were sequenced. Three amino acid differences were found: one in HA2, one in NA and one in PB2 (FIG. 3). To identify the contribution of each individual substitution, and of a combination of two of the substitutions, recombinant viruses with the individual substitution(s) were prepared and the growth of those recombinant viruses was compared to Vero cell-adapted PR8 and non Vero cell-adapted PR8 (FIG. 4). The results indicated that the substitution in HA2 was primarily responsible for the enhanced growth in Vero cells. The substitution in HA2 (N117D) did not enhance growth in MDCK cells (FIG. 5).

Figure 7:
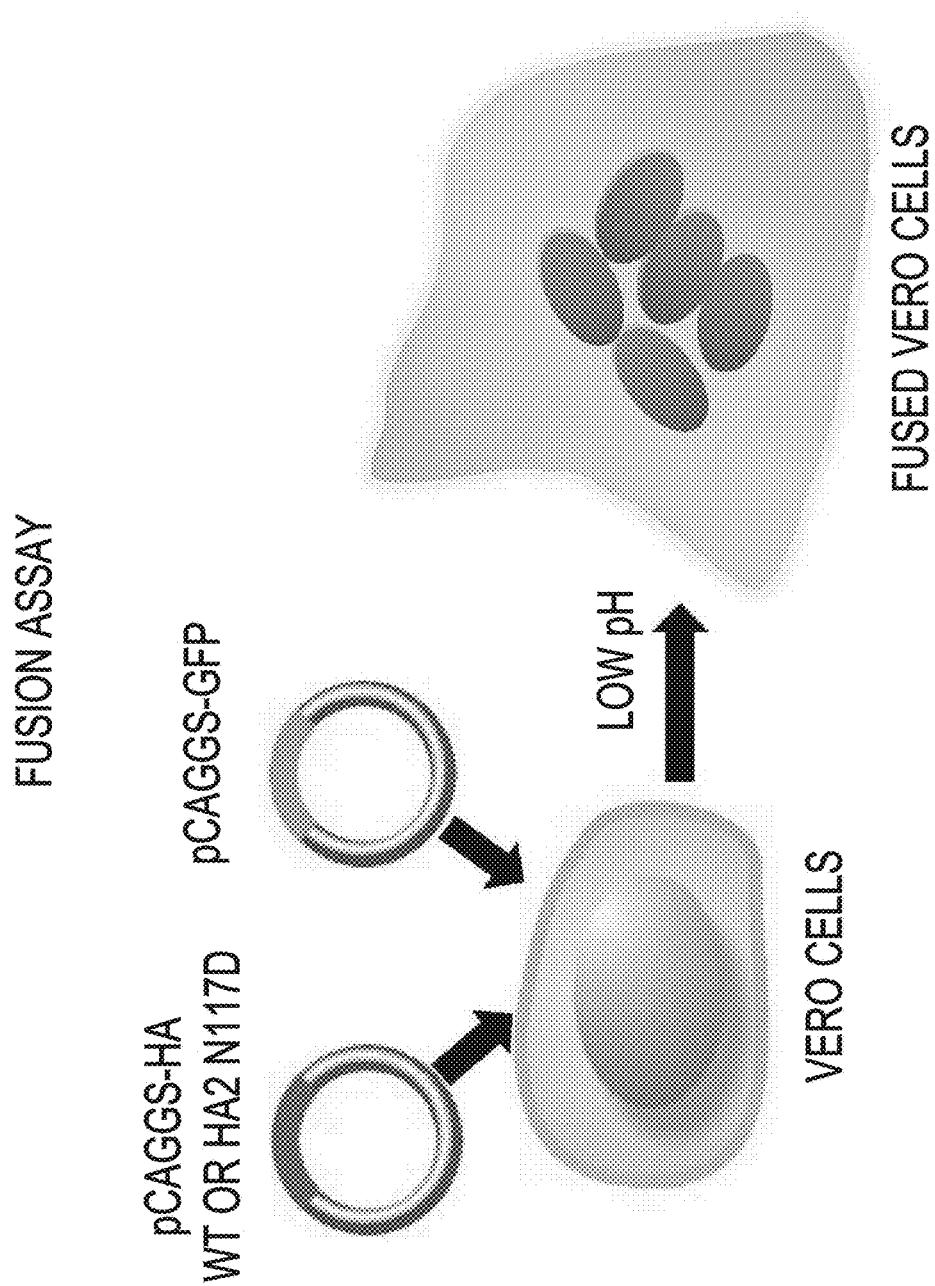
FIG. 7. Schematic of fusion assay which expresses full length HA.
Figure 9A:
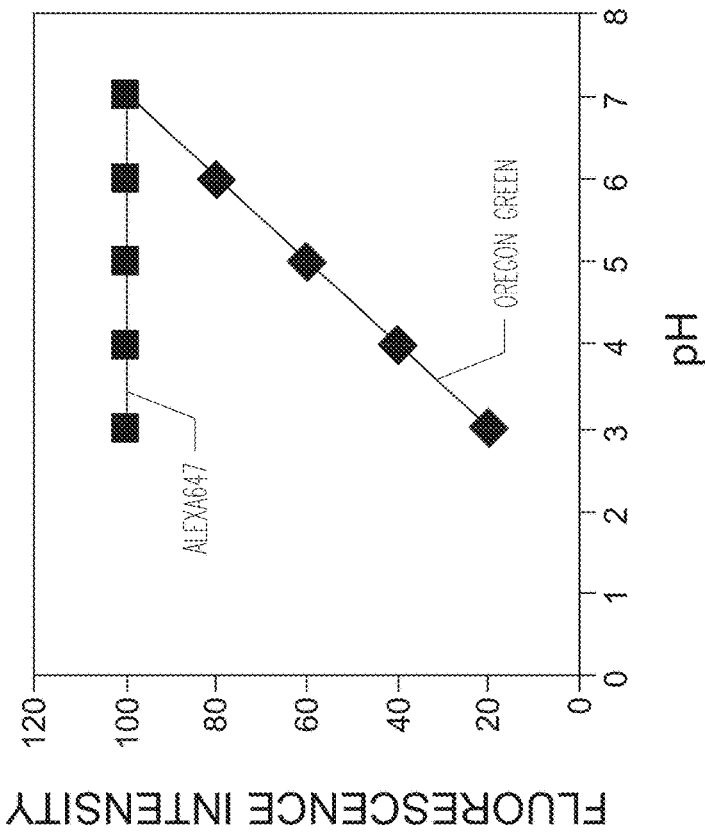
Figure 10:
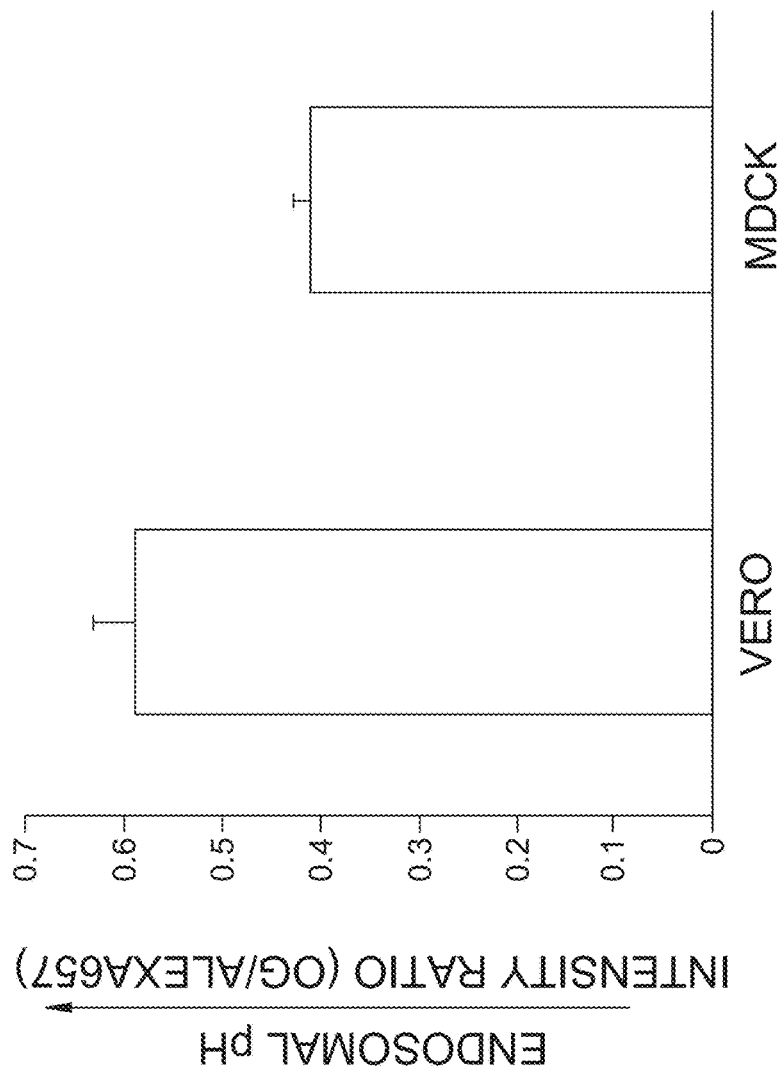
FIG. 10. Comparison of endosomal pH in MDCK cells and Vero cells.
Figure 11A:
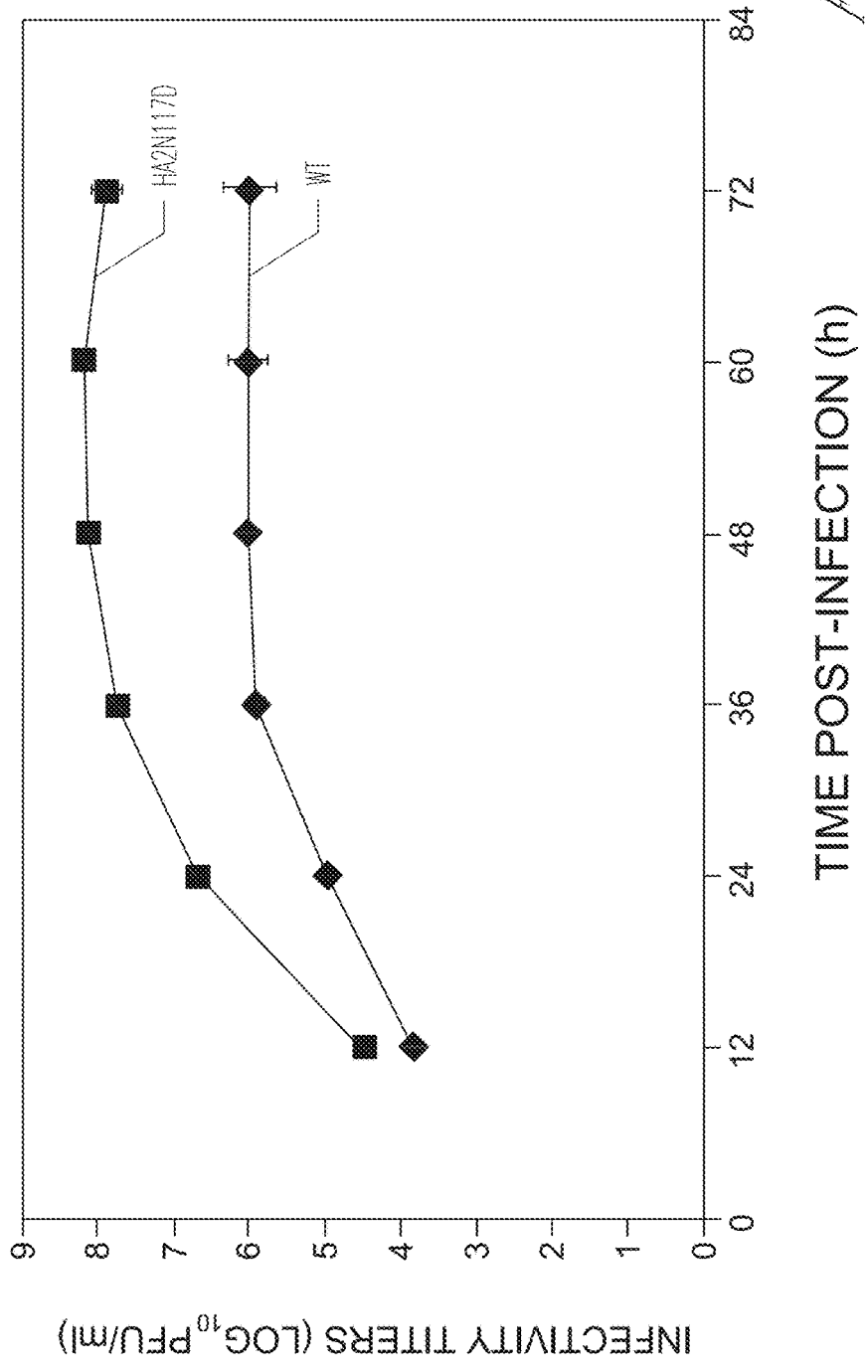

Because HA2 has a fusion domain that is exposed after infection, a fusion assay was employed to compare the properties of wild-type PR8 HA2 and HA2 N17D (FIGS. 7-8). The HA2 N117D mutant fused Vero cells at a higher pH than wild-type PR8. The endosomal pH in Vero cells and MDCK cells was determined using pH sensitive and insensitive dyes (FIGS. 9-10). The endosomes of Vero cells likely have a higher pH than those from MDCK cells. Thus, the HA2 N117D mutation may elevate the optimal pH for membrane fusion mediated by HA2, thereby enhancing virus replication efficiency in Vero cells.

To determine if the HA2 N117D mutation alone could enhance virus replication efficiency in different viruses in Vero cells, that substitution was introduced into two different H1N1 viruses (a AAT to GAT mutation) and one H3N2 virus (a AAC to GAC mutation) in a PR8 background (six gene segments were from Vero cell-adapted PR8; PA, PB1, PB2, M, NS and NP) (FIG. 1). The HA2 N117D mutation enhanced the replication efficiency of all three tested viruses in Vero cells. Such a strategy may be employed to prepare vaccine viruses with enhanced replication in Vero cells.

REFERENCES

*Avery's Drug Treatment: Principles and Practice of Clinical Pharmacology and Theraputics,* 3rd edition, ADIS Press, Ltd., Williams and Wilkins, Baltimore, Md. (1987).
Aymard-Henry et al., *Virology: A Practical Approach*, Oxford IRL Press, Oxford, 119-150 (1985).
Bachmeyer, *Intervirology,* 5:260 (1975).
Berkow et al., eds., *The Merck Manual,* 16th edition, Merck & Co., Rahway, N.J. (1992).
Hatta et al., *Science,* 293:1840 (2001).
Horimoto et al., *J. Virol.,* 68:3120 (1994).
Horimoto et al., *Vaccine,* 24:3669 (2006).
Keitel et al., in Textbook of Influenza, eds. Nickolson, K. G., Webster, R. G., and Hay, A. (Blackwell, Oxford), pp. 373-390 (1998).
Laver & Webster, *Virology,* 69:511 (1976).
Neumann et al., *Adv. Virus Res.,* 53:265 (1999).
Neumann et al., *J. Gen. Virol.,* 83:2635 (2002).
Neumann et al., *J. Virol.,* 71:9690 (1997).
Neumann et al., *Proc. Natl. Acad. Sci. USA,* 96:9345 (1999).
Neumann et al., *Virology,* 287:243 (2001).
Osol (ed.), *Remington's Pharmaceutical Sciences*, Mack Publishing Co., Easton, Pa. 1324-1341 (1980).
Sugawara et al., *Biologicals,* 30:303 (2002).
Webby & Webster et al., *Science,* 302:1519 (2003).
Wood & Robertson, *Nat. Rev. Microbiol.,* 2:842 (2004).
World Health Organization TSR No. 673 (1982).
World Health Organization. Confirmed human cases of avian influenza A (H5N1), http://www.who.int/csr/disease.avian_influenza/country/en/index.html All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to prepare an influenza virus with enhanced replication in Vero cells, comprising:

providing a vector comprising a recombinant nucleic acid molecule comprising sequences for an influenza virus HA segment from a first influenza virus isolate, which segment encodes an HA with an amino acid other than aspartic acid or glutamic acid at position 117 in HA2, wherein the numbering for HA2 residues is that for H1 HA2;

modifying the HA segment to encode an aspartic acid or glutamic acid at position 117 in HA2, thereby yielding a modified HA segment; and contacting a cell with a vector comprising promoter that yields full length, genomic influenza virus RNA or its complement operably linked to an influenza virus PA segment DNA linked to a transcription termination sequence, a vector comprising a promoter that yields full length, genomic influenza virus RNA or its complement operably linked to an influenza virus PB1 segment DNA linked to a transcription termination sequence, a vector comprising a promoter that yields full length, genomic influenza virus RNA or its complement operably linked to an influenza virus PB2 segment DNA linked to a transcription termination sequence, a vector comprising a promoter that yields full length, genomic influenza virus RNA or its complement operably linked to the modified HA segment linked to a transcription termination sequence, a vector comprising a promoter that yields full length, genomic influenza virus RNA or its complement operably linked to an influenza virus NP segment DNA linked to a transcription termination sequence, a vector comprising a promoter that yields full length, genomic influenza virus RNA or its complement operably linked to an influenza virus NA segment DNA linked to a transcription termination sequence, a vector comprising a promoter that yields full length, genomic influenza virus RNA or its complement operably linked to an influenza virus M segment DNA linked to a transcription termination sequence, and a vector comprising a promoter that yields full length, genomic influenza virus RNA or its complement operably linked to an influenza virus NS segment DNA linked to a transcription termination sequence; and a vector comprising a promoter that yields mRNA operably linked to a DNA segment encoding influenza virus PA, a vector comprising a promoter that yields mRNA operably linked to a DNA segment encoding influenza virus PB1, a vector comprising a promoter that yields mRNA operably linked to a DNA segment encoding influenza virus PB2, and a vector comprising a promoter that yields mRNA operably linked to a DNA segment encoding influenza virus NP, and optionally a vector comprising a promoter that yields mRNA operably linked to a DNA segment encoding influenza virus HA, a vector comprising a promoter that yields mRNA operably linked to a DNA segment encoding influenza virus NA, a vector comprising a promoter that yields mRNA operably linked to a DNA segment encoding influenza virus M1, a vector comprising a promoter that yields mRNA operably linked to a DNA segment encoding influenza virus M2, or a vector comprising a promoter that yields mRNA operably linked to a DNA segment encoding influenza virus NS1 or a vector comprising a promoter that yields mRNA operably linked to a DNA segment encoding influenza virus NS2;

in an amount effective to yield infectious influenza virus.

2. The method of claim 1, wherein the PA, PB1, PB2, NP, NS, and M segments are from an influenza vaccine virus isolate.

3. The method of claim 1, wherein the NA segment and the HA segment are from a different isolate than the PA, PB1, PB2, NP, NS, and M segments.

4. The method of claim 1, wherein the NA gene segment and the HA gene segment are from the same influenza virus isolate as the PA, PB1, PB2, NP, NS, and M segments.

5. The method of claim 1, wherein the PA, PB1, PB2, NP, NS, and M segments comprise sequences for at least one of the following: a PB1 having the amino acid sequence encoded by SEQ ID NO:2 or PB1 with at least 90% amino acid sequence identity to the PB1 encoded by SEQ ID NO:2; a PB2 having the amino acid sequence encoded by SEQ ID NO:3 or PB2 with at least 90% amino acid sequence identity to the PB2 encoded by SEQ ID NO:3; a PA having the amino acid sequence encoded by SEQ ID NO:1 or PA with at least 90% amino acid sequence identity to the PA encoded by SEQ ID NO: 1; a NP having the amino acid sequence encoded by SEQ ID NO:4 or NP with at least 90% amino acid sequence identity to the NP encoded by SEQ ID NO:4; a M1 and M2 having the amino acid sequence encoded by SEQ ID NO:5 or M1 and M2 with at least 90% amino acid sequence identity to the M1 and M2 encoded by SEQ ID NO:5; or a NS1 and NS2 having the amino acid sequence encoded by SEQ ID NO:6 or NS1 and NS2 with at least 90% amino acid sequence identity to the NS1 And NS2 encoded by SEQ ID NO:6.

6. The method of claim 1, wherein the PA, PB1, PB2, NP, NS, and M segments comprise sequences for at least one of the following: a PB1 having the amino acid sequence encoded by SEQ ID NO:10 or PB1 with at least 90% amino acid sequence identity to the PB1 encoded by SEQ ID NO:10; a PB2 having the amino acid sequence encoded by SEQ ID NO:11 or PB2 with at least 90% amino acid sequence identity to the PB2 encoded by SEQ ID NO: 11; a PA having the amino acid sequence encoded by SEQ ID NO:12 or PA with at least 90% amino acid sequence identity to the PA encoded by SEQ ID NO: 12; a NP having the amino acid sequence encoded by SEQ ID NO:13 or NP with at least 90% amino acid sequence identity to the NP encoded by SEQ ID NO:13; a M1 and M2 having the amino acid sequence encoded by SEQ ID NO:14 or M1 and M2 with at least 90% amino acid sequence identity to the M1 and M2 encoded by SEQ ID NO:14; or a NS1 and NS2 having the amino acid sequence encoded by SEQ ID NO:15 or NS1 and NS2 with at least 90% amino acid sequence identity to the NS1 and NS2 encoded by SEQ ID NO:15.

7. The method of claim 1, wherein the cell is an isolated mammalian cell.

8. The method of claim 7, wherein the isolated mammalian cell is a Vero cell, an isolated human cell or an isolated hamster cell.

9. The method of claim 1, wherein the HA gene segment is a H1, H2, H3, H5, H7, or H9 segment.

10. The method of claim 1, wherein the HA2 that has an aspartic acid or glutamic acid at position 117 in HA2 has at least 80% amino acid sequence identity to one of SEQ ID Nos. 22-27.

11. A method to prepare an influenza virus with enhanced replication in Vero cells, comprising:
providing a vector comprising a recombinant nucleic acid molecule comprising sequences for an influenza virus HA segment from a first influenza virus isolate, which segment is modified to encode an HA with aspartic acid or glutamic acid at position 117 in HA2, wherein the numbering for HA2 residues is that for H1 HA2; and
contacting a cell with a vector comprising a promoter that yields full length, genomic influenza virus RNA or its complement operably linked to an influenza virus PA segment DNA linked to a transcription termination sequence, a vector comprising a promoter that yields full length, genomic influenza virus RNA or its complement operably linked to an influenza virus PB1 segment DNA linked to a transcription termination sequence, a vector for comprising a promoter that yields full length, genomic influenza virus RNA or its complement operably linked to an influenza virus PB2 segment DNA linked to a transcription termination sequence, a vector comprising a promoter that yields full length, genomic influenza virus RNA or its complement operably linked to the modified HA segment linked to a transcription termination sequence, a vector comprising a promoter that yields full length, genomic influenza virus RNA or its complement operably linked to an influenza virus NP segment DNA linked to a transcription termination sequence, a vector comprising a promoter that yields full length, genomic influenza virus RNA or its complement operably linked to an influenza virus NA segment DNA linked to a transcription termination sequence, a vector comprising a promoter that yields full length, genomic influenza virus RNA or its complement operably linked to an influenza virus M segment DNA linked to a transcription termination sequence, and a vector comprising a promoter that yields full length, genomic influenza virus RNA or its complement operably linked to an influenza virus NS segment DNA linked to a transcription termination sequence; and
a vector comprising a promoter that yields mRNA operably linked to a DNA segment encoding influenza virus PA, a vector comprising a promoter that yields mRNA operably linked to a DNA segment encoding influenza virus PB1, a vector comprising a promoter that yields mRNA operably linked to a DNA segment encoding influenza virus PB2, and a vector comprising a promoter that yields mRNA operably linked to a DNA segment encoding influenza virus NP, and optionally a vector comprising a promoter that yields mRNA operably linked to a DNA segment encoding influenza virus HA, a vector comprising a promoter that yields mRNA operably linked to a DNA segment encoding influenza virus NA, a vector comprising a promoter that yields mRNA operably linked to a DNA segment encoding influenza virus M1, a vector comprising a promoter that yields mRNA operably linked to a DNA segment encoding influenza virus M2, a vector comprising a promoter that yields mRNA operably linked to a DNA segment encoding influenza virus NS1 or a vector comprising a promoter that yields mRNA operably linked to a DNA segment encoding influenza virus NS2,
in an amount effective to yield infectious influenza virus.

12. The method of claim 11, wherein the PB1, PB2, PA, NP, NS, and M segments in the vectors that yield full length, genomic influenza virus RNA or its complement are from the same influenza vaccine virus isolate.

13. The method of claim 11, wherein the NA segment and the HA segment are from a different isolate than the PA, PB1, PB2, NP, NS, and M segments.

14. The method of claim 11, wherein the cell is a Vero cell, an isolated human cell or an isolated hamster cell.

15. The method of claim 11, wherein the HA segment is a H1, H2, H3, H5, H7, or H9 gene segment.

16. A method to prepare an influenza virus with enhanced replication in Vero cells, comprising:
providing an isolated influenza virus having a PA segment, a PB1 segment, a PB2 segment, a NP segment, a NS segment, a M segment, a NA segment, and a HA segment; and
modifying the HA segment to encode an aspartic acid or glutamic acid at position 117 in HA2, wherein the numbering for HA2 residues is that for H1 HA2, thereby yielding a modified influenza virus.

17. The method of claim 16, further comprising introducing the modified virus into a cell.

18. The method of claim 16, wherein the modified virus has enhanced replication in Vero cells relative to the isolated virus.

19. The method of claim 16, wherein the modified virus has a titer at least one log greater in Vero cells than the isolated virus.

20. The method of claim 19 wherein the isolated virus has an alanine, asparagine, arginine or lysine at position 117 in HA2.

* * * * *